(12) United States Patent
Collins et al.

(10) Patent No.: US 6,989,392 B2
(45) Date of Patent: Jan. 24, 2006

(54) 2-AMINOQUINOLINES AS MELANIN CONCENTRATING HORMONE RECEPTOR ANTAGONISTS

(75) Inventors: Christine A. Collins, Skokie, IL (US); Ju Gao, Gurnee, IL (US); Philip R. Kym, Grayslake, IL (US); Jared C. Lewis, Oakland, CA (US); Andrew J. Souers, Evanston, IL (US); Anil Vasudevan, Gurnee, IL (US); Dariusz Wodka, Waukegan, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/460,139

(22) Filed: Jun. 12, 2003

(65) Prior Publication Data

US 2004/0063756 A1    Apr. 1, 2004

Related U.S. Application Data

(60) Provisional application No. 60/389,558, filed on Jun. 18, 2002.

(51) Int. Cl.
*A61K 31/47*    (2006.01)
*C07D 215/38*   (2006.01)
*C07D 215/44*   (2006.01)

(52) U.S. Cl. .................... 514/312; 546/159; 546/161; 546/162

(58) Field of Classification Search ............... 514/312; 546/159, 161, 162
See application file for complete search history.

(56) References Cited

U.S. PATENT DOCUMENTS

| 4,075,343 | A | 2/1978 | Kadin |
| 4,886,805 | A | 12/1989 | Bru-Magniez et al. |
| 6,297,021 | B1 | 10/2001 | Nienaber et al. |
| 6,465,467 | B1 * | 10/2002 | Nilsson et al. .......... 514/252.11 |
| 6,593,330 | B2 * | 7/2003 | Nilsson ................ 514/252.11 |

FOREIGN PATENT DOCUMENTS

| BE | 858605 | 3/1978 |
| DE | 2513930 | 10/1975 |
| EP | 0 254 623 | 1/1988 |
| JP | 55130961 | 10/1980 |
| WO | 0042026 | 7/2000 |
| WO | 00 76984 | 12/2000 |
| WO | 0116108 | 3/2001 |
| WO | 01 40217 | 6/2001 |
| WO | 02 40456 | 5/2002 |
| WO | 03/045313 A2 | 6/2003 |
| WO | 03045313 | 6/2003 |
| WO | 03045920 | 6/2003 |

OTHER PUBLICATIONS

Cricchio, CA 83:206044, abstract only, 1975.*
Savini, Farmaco, 56(12), 939-945, 2001.*
Lee, Chemical Abstracts 134:71484, abstract of Archives of Pharmacal Research, 23(5), pp 450-454, 2000.*
Alonso, Chemical Abstracts 120:297779, abstract of Tetrahedron, 49(47), pp 10997-11008, 1993.*
Thakore, Chemical Abstracts 93:95109, abstract of Journal of the Indian Chemical Aocxiety, 56(12), pp 1239-1242, 1979.*
Kamel, Chemical Abstracts 130:66375, abstract of Egyptian Journal of Pharmaceutical Sciences, vol. 38(1-3), pp 79-86, 1997.*
Desai, Chemical Abstracts 129:51958, abstract of Asian Journal Of Chemicstry, 10(3), pp 615-617, 1998.*
Litvinov, Chemical Abstracts 91:39288, abstract of Voprosy khimii i Khimicheskoi Technologii, vol. 52, pp 34-37, 1978.*
Soulen, Journal of Organic Chemistry, 32(9), pp 2661-2663, 1967.*
Althuis, J Med Chem, 23, pp 262-269, 1980.
Clements-Jewery, J Med Chem, 31, pp 1220-1226, 1988.
Albrecht, Tetrahedron, 58(3), 561-567, 2002.
Peterson, Proceed. of Nat. Acad. of Sc. of the USA, 97 (24), 12965-12969, 2000.
Glennon, Richard, A., et al, J. of Med. Chem. 29 (11), pp 2375-80 (1986).
Sampei, N., et al., Sankyo Kenkyusho Nempo, vol. 16, 42-8 (1964).

* cited by examiner

Primary Examiner—D. Margaret Seaman
(74) Attorney, Agent, or Firm—Johanna M. Corbin

(57) ABSTRACT

The present invention is related to compounds of formula (I),

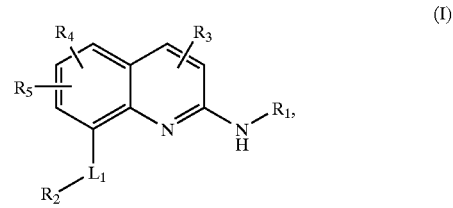

(I)

or a therapeutically suitable salt or prodrug thereof, which antagonize the effects of melanin-concentrating hormone (MCH) through the melanin concentrating hormone receptor and are useful for the prevention or treatment of eating disorders, weight gain and obesity.

14 Claims, No Drawings

2-AMINOQUINOLINES AS MELANIN CONCENTRATING HORMONE RECEPTOR ANTAGONISTS

This application claims priority to the U.S. Provisional Application Ser. No. 60/389,558 filed on Jun. 18, 2002, incorporated herein by reference.

FIELD OF THE INVENTION

The present invention relates to the antagonism of the effects of melanin-concentrating hormone (MCH) through the melanin concentrating hormone receptor which is useful for the prevention or treatment of eating disorders, weight gain, obesity, abnormalities in reproduction and sexual behavior, thyroid hormone secretion, diuresis and water/electrolyte homeostasis, sensory processing, memory, sleeping, arousal, anxiety, depression, seizures, neurodegeneration and psychiatric disorders.

BACKGROUND OF THE INVENTION

Obesity is a major cause and contributor to health problems such as type II diabetes, coronary heart disease, increased incidence of certain forms of cancer, and respiratory complications. It is a disease that is increasing at an alarming rate due to increased availability of high-fat diets, genetic susceptibility, and a more sedentary way of life in modern society. Obesity can be defined as weight gain resulting from a mismatch of energy intake and energy expenditure. Food intake and energy metabolism are regulated, in part, by the interaction of neuropeptides and their receptors. Recently, the role that the hormone leptin plays in controlling appetite has been elucidated.

Leptin is a peptide hormone produced by fat cells, regulating both food intake and and metabolism by acting on leptin receptors in the hypothalamus. Increased fat stores leads to increased secretion of leptin, resulting in a signal to the hypothalamus to decrease food intake, whereas decreases in adiposity result in lower leptin levels and a stimulation of food intake. Melanin-concentrating hormone (MCH) has been identified as an orexigenic peptide that counterbalances the activity of leptin.

MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. Mice lacking MCH are hypophagic and lean with increased metabolic rate, whereas animals over-expressing MCH gain excess weight on both standard and high fat diets. An orphan G-protein coupled receptor (GPCR) was recently identified as a receptor for MCH.

Although there exists current pharmacologic therapies used to treat obesity, none of the current therapies achieve the U.S. Food and Drug Administration criteria for benefit measured by a 5% difference in mean weight loss, as weight loss efficacy is diminished by reduction of patient adherence to pharmacological therapy due to side effects of the drugs. Some of the side effects associated with current therapies include increased heart rate and blood pressure, and uncontrolled excretion of fat in stools. Thus, there exists a medical need for agents capable of preventing or treating eating disorders, weight gain and obesity, that at the same time, have improved efficacy and safety.

SUMMARY OF THE INVENTION

The present invention is directed to compound of formula (I),

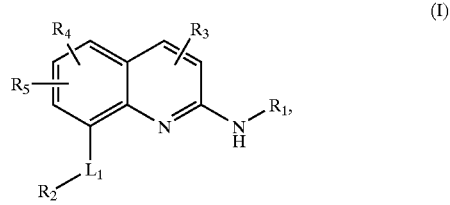

or a therapeutically suitable salt or prodrug thereof, wherein $L_1$ is a bond or is a member selected from the group consisting of —C(O)—, —O—, —S—, —S(O)—, and —S(O)$_2$—; $R_1$ is a member selected from the group consisting of hydrogen, alkyl, alkoxy, aryl, arylalkyl, arylalkoxy, arylcarbonyl, heterocycle, heterocyclealkyl, $R_AR_BN$—, and $R_AR_B$Ncarbonyl; $R_2$ is a member selected from the group consisting of alkyl, alkoxy, alkenyl, alkoxyalkyl, aryl, arylalkyl, aryloxyalkyl, cycloalkyl, cycloalkylalkyl, haloalkyl, heterocycle, heterocyclealkyl, heterocycleoxyalkyl, heterocycleoxyalkoxyalkyl, $R_7L_2R_6$—, $R_A$Salkyl, and $R_AR_B$Nalkyl; $R_3$ is a member selected from the group consisting of hydrogen, alkyl, hydroxy, cyano, halo, haloalkoxy, $R_AR_BN$—, and alkylcarbonylNH—; $R_4$, and $R_5$ are each independently a member selected from the group consisting of hydrogen, alkyl, alkoxy, hydroxy, cyano, halo, haloalkoxy, $R_AR_BN$—, and alkylcarbonylNH—; $R_6$ and $R_7$ are each independently a member selected from the group consisting of aryl, cycloalkyl, and heterocycle; $R_A$ and $R_B$ are each independently a member selected from the group consisting of hydrogen, alkyl, aryl and heterocycle; $L_2$ is —(CH$_2$)$_m$X(CH$_2$)$_n$—; X is a member selected from the group consisting of —C(O)—, —O—, —S—, —S(O)—, —S(O)$_2$— or is a covalent bond; m is 0, 1, 2, 3, or 4; n is 0, 1, 2, 3, or 4; provided that if i) any of $R_3$, $R_4$, or $R_5$ is alkyl or alkoxy, or if ii) L is a bond and $R_2$ is either alkyl or alkoxy; then $R_1$ must be other than hydrogen.

According to one embodiment of the present invention, there is provided a method of treating disorders mediated by MCH through the MCH receptor comprising administering a therapeutically effective amount of a compound of formula (I). According to another embodiment of the present invention, there is provided a method for treating treating eating disorders, weight gain and obesity comprising administering a therapeutically effective amount of a compound of formula (I). According to another embodiment of the present invention, there is provided a method for treating treating abnormalities in reproduction and sexual behavior, thyroid hormone secretion, diuresis and water/electrolyte homeostasis, sensory processing, memory, sleeping, arousal, anxiety, depression, seizures, neurodegeneration and psychiatric disorders comprising administering a therapeutically effective amount of a compound of formula (I).

According to still another embodiment, the present invention is directed to a pharmaceutical composition comprising a therapeutically effective amount of a compound of formula (I) in combination with a pharmaceutically suitable carrier.

DETAILED DESCRIPTION OF THE INVENTION

DEFINITIONS

As used throughout this specification and the appended claims, the following terms have the following meanings:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl," as used herein, refers to an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy," as used herein, refers to an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio," as used herein, refers to an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of this invention can be substituted with 1, 2, or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, halogen, haloalkyl, heterocycle, heterocyclealkyl, hydroxy, hydroxyalkyl, mercapto, nitro, phenyl and —$NR_CR_D$ wherein $R_C$ and $R_D$ are each independently selected from the group consisting of hydrogen, alkyl, alkylcarbonyl.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "carbonyl," as used herein, refers to a —C(O)— group.

The term "carboxy," as used herein, refers to a —$CO_2H$ group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0³,⁷]nonane and tricyclo[3.3.1.1³,⁷]decane (adamantane).

The term "formyl," as used herein, refers to a —C(O)H group.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido[1,2-α]pyrimidin-4-one, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo[b,d]furanyl, dibenzo[b,d]thienyl, naphtho[2,3-b]furan, naphtho[2,3-b]thienyl, phenazinyl, phenothiazinyl, phenoxazinyl, thianthrenyl, thioxanthenyl and xanthenyl.

According to the present invention, heterocycles of this invention can be substituted with 1, 2, or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, carboxy, carboxyalkyl, cyano, cyanoalkyl, formyl, halogen, haloalkyl, hydroxy, hydroxyalkyl, mercapto, nitro, phenyl, and $R_CR_BN$—, $R_CR_BN$carbonyl, $R_CR_BN$alkyl, wherein $R_C$ and $R_D$ are defined herein.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl and the like.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, 2-hydroxyethyl, 2-hydroxypropyl, 3-hydroxybutyl and the like.

The term "mercapto," as used herein, refers to a —SH group.

The term "$R_AR_BN$—," as used herein, refers to both $R_A$ and $R_B$ appended to the parent molecular moiety through a —N— group.

The term "nitro," as used herein, refers to a —NO₂ group.

The term "$R_AR_B$Nalkyl," as used herein, refers to a $R_AR_BN$ group, as defined herein, appended to the parent molecular moiety through an alkyl group, as defined herein.

The term "$R_AR_B$Ncarbonyl," as used herein, refers to a $R_AR_BN$ group, as defined herein, appended to the parent molecular moiety through a carbonyl group, as defined herein.

The term "$R_AS$," as used herein, refers to a $R_A$ group, as defined herein, appended to the parent molecular moiety through a —S— group, as defined herein.

The term "$R_AS$alkyl," as used herein, refers to a $R_AS$ group, as defined herein, appended to the parent molecular moiety through an alkyl group, as defined herein.

The present invention is directed to compounds of formula (I), wherein $R_1$, $R_2$, $R_3$, $R_4$, $R_5$, $R_A$, $R_B$, and L are defined herein. The compounds of the present invention are useful for treating disorders mediated by MCH through the MCH receptor.

According to one embodiment of the present invention there is provided a method of treating or preventing disorders mediated by MCH through the MCH receptor comprising administrering a therapeutically effective amount of a compound of formula (I).

According to the principle embodiment of the present invention there is provided a compound of formula (I),

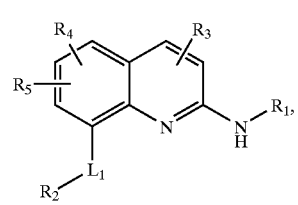

or a therapeutically suitable salt or prodrug thereof, wherein $L_1$ is a bond or is a member selected from the group consisting of —C(O)—, —O—, —S—, —S(O)—, and —S(O)₂—; $R_1$ is a member selected from the group consisting of hydrogen, alkyl, alkoxy, aryl, arylalkyl, arylalkoxy, arylcarbonyl, heterocycle, heterocyclealkyl, $R_AR_BN$—, and $R_AR_B$Ncarbonyl; $R_2$ is a member selected from the group consisting of alkyl, alkoxy, alkenyl, alkoxyalkyl, aryl, arylalkyl, aryloxyalkyl, cycloalkyl, cycloalkylalkyl, haloalkyl, heterocycle, heterocyclealkyl, heterocycleoxyalkyl, heterocycleoxyalkoxyalkyl, $R_7L_2R_6$—, $R_AS$alkyl, and $R_AR_B$Nalkyl; $R_3$ is a member selected from the group consisting of hydrogen, alkyl, hydroxy, cyano, halo, haloalkoxy, $R_AR_BN$—, and alkylcarbonylNH—; $R_4$, and $R_5$ are each independently a member selected from the group consisting of hydrogen, alkyl, alkoxy, hydroxy, cyano, halo, haloalkoxy, $R_AR_BN$—, and alkylcarbonylNH—; $R_6$ and $R_7$ are each independently a member selected from the group consisting of aryl, cycloalkyl, and heterocycle; $R_A$ and $R_B$ are each independently a member selected from the group consisting of hydrogen, alkyl, aryl and heterocycle; $L_2$ is —(CH$_2$)$_m$X(CH$_2$)$_n$—; X is a member selected from the group consisting of —C(O)—, —O—, —S—, —S(O)—, —S(O)$_2$— or is a covalent bond; m is 0, 1, 2, 3, or 4; n is 0, 1, 2, 3, or 4; provided that if i) any of $R_3$, $R_4$, or $R_5$ is alkyl or alkoxy, or if ii) L is a bond and $R_2$ is either alkyl or alkoxy; then $R_1$ must be other than hydrogen.

According to another embodiment of the present invention there is provided a compound according to formula (Ia),

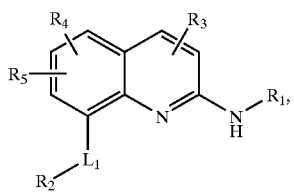

(Ia)

or a therapeutically suitable salt or prodrug thereof, wherein $L_1$ is —O—; $R_1$ is a member selected from the group consisting of hydrogen, alkyl, alkoxy, aryl, arylalkyl, arylalkoxy, arylcarbonyl, heterocycle, heterocyclealkyl, $R_AR_BN$—, and $R_AR_B$Ncarbonyl; $R_2$ is a member selected from the group consisting of alkyl, alkenyl; $R_3$ is a member selected from the group consisting of hydrogen, alkyl, hydroxy, cyano, halo, haloalkoxy, $R_AR_BN$—, and alkylcarbonylNH—; $R_4$, and $R_5$ are each independently a member selected from the group consisting of hydrogen, alkyl, alkoxy, hydroxy, cyano, halo, haloalkoxy, $R_AR_BN$—, and alkylcarbonylNH—; $R_A$ and $R_B$ are each independently a member selected from the group consisting of hydrogen, alkyl, aryl and heterocycle; with the following provisions that if any of $R_3$, $R_4$, or $R_5$ is alkyl or alkoxy, or if $R_2$ is alkyl, wherein alkyl is $C_5$ or smaller; then $R_1$ must be other then hydrogen.

According to another embodiment of the present invention there is provided a compound according to formula (Ia), or a therapeutically suitable salt or prodrug thereof, wherein $L_1$ is —O—; $R_1$ is a member selected from the group consisting of alkyl, alkoxy, aryl, arylalkyl, arylalkoxy, arylcarbonyl, heterocycle, heterocyclealkyl, $R_AR_BN$— and $R_AR_B$Ncarbonyl; $R_2$ is a member selected from the group consisting of alkyl, alkenyl; $R_3$ is a member selected from the group consisting of hydrogen, alkyl, hydroxy, cyano, halo, haloalkoxy, $R_AR_BN$—, and alkylcarbonylNH—; $R_4$, and $R_5$ are each independently a member selected from the group consisting of hydrogen, alkyl, alkoxy, hydroxy, cyano, halo, haloalkoxy, $R_AR_BN$—, and alkylcarbonylNH—; $R_A$ and $R_B$ are each independently a member selected from the group consisting of hydrogen, alkyl, aryl and heterocycle.

According to another embodiment of the present invention there is provided a compound according to formula (Ib),

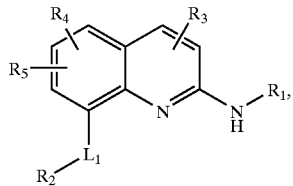

(Ib)

or a therapeutically suitable salt or prodrug thereof, wherein $L_1$ is —O—; $R_1$ is a member selected from the group consisting of hydrogen, alkyl, alkoxy, aryl, arylalkyl, arylalkoxy, arylcarbonyl, heterocycle, heterocyclealkyl, $R_AR_BN$—, and $R_AR_B$Ncarbonyl; $R_2$ is alkyl, wherein alkyl is $C_6$ or larger; $R_3$ is a member selected from the group consisting of hydrogen, alkyl, hydroxy, cyano, halo, haloalkoxy, $R_AR_BN$—, and alkylcarbonylNH—; $R_4$, and $R_5$ are each independently a member selected from the group consisting of hydrogen, alkyl, alkoxy, hydroxy, cyano, halo, haloalkoxy, $R_AR_BN$—, and alkylcarbonylNH—; and $R_A$ and $R_B$ are each independently a member selected from the group consisting of hydrogen, alkyl, aryl and heterocycle.

According to another embodiment of the present invention there is provided a compound according to formula (Ic),

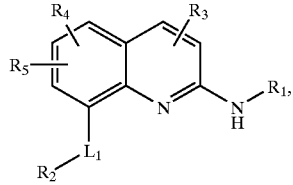

(Ic)

or a therapeutically suitable salt or prodrug thereof, wherein $L_1$ is —O—; $R_1$ is a member selected from the group consisting of hydrogen, alkyl, alkoxy, aryl, arylalkyl, arylalkoxy, arylcarbonyl, heterocycle, heterocyclealkyl, $R_AR_BN$—, and $R_AR_B$Ncarbonyl; $R_2$ is a member selected from the group consisting of alkoxyalkyl, haloalkyl, $R_A$S-alkyl, and $R_AR_B$Nalkyl; $R_3$ is a member selected from the group consisting of hydrogen, alkyl, hydroxy, cyano, halo, haloalkoxy, $R_AR_BN$—, and alkylcarbonylNH—; $R_4$, and $R_5$ are each independently a member selected from the group consisting of hydrogen, alkyl, alkoxy, hydroxy, cyano, halo, haloalkoxy, $R_AR_BN$—, and alkylcarbonylNH—; $R_A$ and $R_B$ are each independently a member selected from the group consisting of hydrogen, alkyl, aryl and heterocycle.

According to another embodiment of the present invention there is provided a compound according to formula (Id),

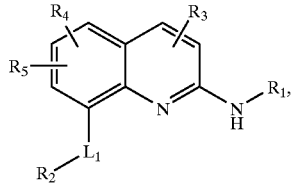

(Id)

or a therapeutically suitable salt or prodrug thereof, wherein L₁ is —O—; R₁ is a member selected from the group consisting of hydrogen, alkyl, alkoxy, aryl, arylalkyl, arylalkoxy, arylcarbonyl, heterocycle, heterocyclealkyl, R$_A$R$_B$N—, and R$_A$R$_B$Ncarbonyl; R₂ is a member selected from the group consisting of aryl, cycloalkyl and heterocycle; R₃ is a member selected from the group consisting of hydrogen, alkyl, hydroxy, cyano, halo, haloalkoxy, R$_A$R$_B$N—, and alkylcarbonylNH—; R₄, and R₅ are each independently a member selected from the group consisting of hydrogen, alkyl, alkoxy, hydroxy, cyano, halo, haloalkoxy, R$_A$R$_B$N—, and alkylcarbonylNH—; R$_A$ and R$_B$ are each independently a member selected from the group consisting of hydrogen, alkyl, aryl and heterocycle.

According to another embodiment of the present invention there is provided a compound according to formula (Ie),

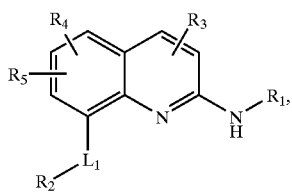

(Ie)

or a therapeutically suitable salt or prodrug thereof, wherein L₁ is —O—; R₁ is a member selected from the group consisting of hydrogen, alkyl, alkoxy, aryl, arylalkyl, arylalkoxy, arylcarbonyl, heterocycle, heterocyclealkyl, R$_A$R$_B$N—, and R$_A$R$_B$Ncarbonyl; R₂ is a member selected from the group consisting of arylalkyl, aryloxyalkyl, cycloalkylalkyl, heterocyclealkyl, heterocycleoxyalkyl, heterocycleoxyalkoxyalkyl, R₇L₂R₆—; R₃ is a member selected from the group consisting of hydrogen, alkyl, hydroxy, cyano, halo, haloalkoxy, R$_A$R$_B$N—, and alkylcarbonylNH—; R₄, and R₅ are each independently a member selected from the group consisting of hydrogen, alkyl, alkoxy, hydroxy, cyano, halo, haloalkoxy, R$_A$R$_B$N—, and alkylcarbonylNH—; R$_A$ and R$_B$ are each independently a member selected from the group consisting of hydrogen, alkyl, aryl and heterocycle.

According to another embodiment of the present invention there is provided a method of treating disorders mediated by MCH through the MCH receptor comprising administering a therapeutically effective amount of a compound of formula (I).

According to another embodiment of the present invention there is provided a method for treating eating disorders, weight gain and obesity comprising administering a therapeutically effective amount of a compound of formula (I).

According to another embodiment of the present invention there is provided a method for treating abnormalities in reproduction and sexual behavior, thyroid hormone secretion, diuresis and water/electrolyte homeostasis, sensory processing, memory, sleeping, arousal, anxiety, depression, seizures, neurodegeneration and psychiatric disorders comprising administering a therapeutically effective amount of a compound of formula (I).

According to another embodiment of the present invention there is provided a pharmaceutical composition comprising a therapeutically effective amount of a compound of formula (I) in combination with a pharmaceutically suitable carrier. Specific compounds of formula (I) include, but are not limited to:

8-isopropoxyquinolin-2-amine;
8-(cyclobutyloxy)quinolin-2-amine;
8-sec-butoxyquinolin-2-amine;
8-(cyclopentyloxy)quinolin-2-amine;
8-(1-methylbutoxy)quinolin-2-amine;
8-(1,2-dimethylpropoxy)quinolin-2-amine;
8-(1-ethylpropoxy)quinolin-2-amine;
8-(2-methoxy-1-methylethoxy)quinolin-2-amine;
8-(cyclohexyloxy)quinolin-2-amine;
8-((3-methylcyclopentyl)oxy)quinolin-2-amine;
8-((2-methylcyclohexyl)oxy)quinolin-2-amine;
8-(2-ethoxy-1-methylethoxy)quinolin-2-amine;
8-((3-methylcyclohexyl)oxy)quinolin-2-amine;
8-((4-methylcyclohexyl)oxy)quinolin-2-amine;
8-(cycloheptyloxy)quinolin-2-amine;
8-(1,3,3-trimethylbutoxy)quinolin-2-amine;
8-(2-ethyl-1-methylbutoxy)quinolin-2-amine;
8-ethoxyquinolin-2-amine;
8-propoxyquinolin-2-amine;
8-butoxyquinolin-2-amine;
8-isobutoxyquinolin-2-amine;
8-(cyclobutylmethoxy)quinolin-2-amine;
8-(2-cyclopropylethoxy)quinolin-2-amine;
8-(pentyloxy)quinolin-2-amine;
8-(2-methylbutoxy)quinolin-2-amine;
8-(3-methylbutoxy)quinolin-2-amine;
8-(2-(methylthio)ethoxy)quinolin-2-amine;
8-(cyclopentylmethoxy)quinolin-2-amine;
8-(tetrahydrofuran-3-ylmethoxy)quinolin-2-amine;
8-(hexyloxy)quinolin-2-amine;
8-(3,3-dimethylbutoxy)quinolin-2-amine;
8-(3,3,3-trifluoropropoxy)quinolin-2-amine;
8-(cyclohexylmethoxy)quinolin-2-amine;
8-(3-methoxy-3-methylbutoxy)quinolin-2-amine;
8-(2-cyclohexylethoxy)quinolin-2-amine;
8-((1S,4R)-bicyclo[2.2.1]hept-2-ylmethoxy)quinolin-2-amine;
8-((1-ethylpentyl)oxy)quinolin-2-amine;
8-(((1R)-1-methylpropyl)oxy)quinolin-2-amine;
8-(1-cyclohexylpropoxy)quinolin-2-amine;
8-(1-ethyl-2-methylpropoxy)quinolin-2-amine;
8-(((1R,2S)-2-methylcyclohexyl)oxy)quinolin-2-amine;
8-(((1S)-1,2-dimethylpropyl)oxy)quinolin-2-amine;
8-(1-(methoxymethyl)propoxy)quinolin-2-amine;
8-(3-ethoxy-1-ethylpropoxy)quinolin-2-amine;
8-(((1R)-1,2-dimethylpropyl)oxy)quinolin-2-amine;
8-(((1S)-2-methyl-1-phenylpropyl)oxy)quinolin-2-amine;
8-(((1R,2S)-2-methylcyclopentyl)oxy)quinolin-2-amine;
8-(1,2-diethylbutoxy)quinolin-2-amine;
8-((1,4-diethylhexyl)oxy)quinolin-2-amine;
8-(1,3-dimethylbutoxy)quinolin-2-amine;
8-(((1R,2R)-2-methylcyclohexyl)oxy)quinolin-2-amine;
8-((1-isopropylbut-3-enyl)oxy)quinolin-2-amine;
8-((1-isopropylpentyl)oxy)quinolin-2-amine;
8-(1-benzylpropoxy)quinolin-2-amine;
8-(1-(4-fluorophenyl)ethoxy)quinolin-2-amine;
8-(1-cyclohexylethoxy)quinolin-2-amine;
8-(1-methyl-2-phenylethoxy)quinolin-2-amine;
8-(((1S)-1-methylpropyl)oxy)quinolin-2-amine;
8-(2,3-dihydro-1H-inden-2-yloxy)quinolin-2-amine;
8-(3-methoxybutoxy)quinolin-2-amine;
8-(2-(1-naphthyl)ethoxy)quinolin-2-amine;
8-((1-ethyl-4-methylpentyl)oxy)quinolin-2-amine;
8-(((1S,5S)-3,3,5-trimethylcyclohexyl)oxy)quinolin-2-amine;

8-(((1R,5S)-3,3,5-trimethylcyclohexyl)oxy)quinolin-2-amine;
8-(benzyloxy)quinolin-2-amine;
8-((3-(trifluoromethyl)benzyl)oxy)quinolin-2-amine;
8-((2,4-dimethylbenzyl)oxy)quinolin-2-amine;
8-(((3S)-1-benzylpyrrolidin-3-yl)oxy)quinolin-2-amine;
8-(((3R)-1-benzylpyrrolidin-3-yl)oxy)quinolin-2-amine;
8-((1-benzylpiperidin-4-yl)oxy)quinolin-2-amine;
8-((1,5-dimethylhex-4-enyl)oxy)quinolin-2-amine;
8-(((1R)-1-phenylethyl)oxy)quinolin-2-amine;
8-(1-(4-(trifluoromethyl)phenyl)ethoxy)quinolin-2-amine;
8-(2-(1-methylpyrrolidin-2-yl)ethoxy)quinolin-2-amine;
8-(2-(2-((2-aminoquinolin-8-yl)oxy)ethoxy)ethoxy)-quinolin-2-amine;
8-((4-(((2-aminoquinolin-8-yl)oxy)methyl)benzyl)oxy)-quinolin-2-amine;
3-((2-aminoquinolin-8-yl)oxy)propan-1-ol;
8-(3-((2-methylquinolin-8-yl)oxy)propoxy)quinolin-2-amine;
8-(3-(quinolin-8-yloxy)propoxy)quinolin-2-amine;
8-(3-((2-aminoquinolin-8-yl)oxy)propoxy)quinolin-2-ol;
6-(3-((2-aminoquinolin-8-yl)oxy)propoxy)quinolin-2-ol;
4-(3-((2-aminoquinolin-8-yl)oxy)propoxy)quinolin-2-amine;
8-(3-phenoxypropoxy)quinolin-2-amine;
8-(3-(3,5-dichlorophenoxy)propoxy)quinolin-2-amine;
4-((2-aminoquinolin-8-yl)oxy)pentan-1-ol;
8-(1-methyl-4-((2-methylquinolin-8-yl)oxy)butoxy)quinolin-2-amine;
8-(4-((2-aminoquinolin-8-yl)oxy)-1-methylbutoxy)quinolin-2-amine;
8-(4-(3,5-dichlorophenoxy)-1-methylbutoxy)quinolin-2-amine;
8-(4-(2-methoxyphenoxy)-1-methylbutoxy)quinolin-2-amine;
8-(1-methyl-4-(quinolin-7-yloxy)butoxy)quinolin-2-amine;
N-(4-((4-((2-aminoquinolin-8-yl)oxy)pentyl)oxy)phenyl)acetamide;
methyl 3-((4-((2-aminoquinolin-8-yl)oxy)pentyl)oxy)benzoate;
8-(1-methyl-4-(3,4,5-trimethylphenoxy)butoxy)quinolin-2-amine;
methyl O-(4-((2-aminoquinolin-8-yl)oxy)pentyl)-L-tyrosinate;
8-(1-methyl-4-(2-naphthyloxy)butoxy)quinolin-2-amine;
1-(4-((4-((2-aminoquinolin-8-yl)oxy)pentyl)oxy)-3-methylphenyl)ethanone;
8-(1-methyl-4-(4-propylphenoxy)butoxy)quinolin-2-amine;
8-(4-(3-isopropylphenoxy)-1-methylbutoxy)quinolin-2-amine;
8-(4-(4-chloro-3-fluorophenoxy)-1-methylbutoxy)quinolin-2-amine;
2-((4-((2-aminoquinolin-8-yl)oxy)pentyl)oxy)benzonitrile;
2-((4-((2-aminoquinolin-8-yl)oxy)pentyl)oxy)benzamide;
8-(1-methyl-4-(2-methyl-5-nitrophenoxy)butoxy)quinolin-2-amine;
8-(4-((5-amino-1-naphthyl)oxy)-1-methylbutoxy)quinolin-2-amine;
8-(4-(3-anilinophenoxy)-1-methylbutoxy)quinolin-2-amine;
8-(4-(2-chloro-4-methoxyphenoxy)-1-methylbutoxy)quinolin-2-amine;
8-(4-((4-methoxy-1-naphthyl)oxy)-1-methylbutoxy)quinolin-2-amine;
methyl (4-((4-((2-aminoquinolin-8-yl)oxy)pentyl)oxy)phenyl)acetate;
ethyl 2-((4-((2-aminoquinolin-8-yl)oxy)pentyl)oxy)-5-methylbenzoate;
8-(4-(4-bromo-2-fluorophenoxy)-1-methylbutoxy)quinolin-2-amine;
N-(3-((4-((2-aminoquinolin-8-yl)oxy)pentyl)oxy)phenyl)urea;
4-(4-((4-((2-aminoquinolin-8-yl)oxy)pentyl)oxy)phenyl)butan-2-one;
ethyl 2-((4-((2-aminoquinolin-8-yl)oxy)pentyl)oxy)benzoate;
methyl 2-((4-((2-aminoquinolin-8-yl)oxy)pentyl)oxy)-5-methoxybenzoate;
8-(4-(4-amino-2-chlorophenoxy)-1-methylbutoxy)quinolin-2-amine;
1-(4-((4-((2-aminoquinolin-8-yl)oxy)pentyl)oxy)phenyl)propan-1-one;
8-(4-(3-(diethylamino)phenoxy)-1-methylbutoxy)quinolin-2-amine;
8-(4-(isoquinolin-5-yloxy)-1-methylbutoxy)quinolin-2-amine;
8-(4-(1,1'-biphenyl-3-yloxy)-1-methylbutoxy)quinolin-2-amine;
8-(4-(2-fluoro-5-methylphenoxy)-1-methylbutoxy)quinolin-2-amine;
8-(4-(2-ethoxy-5-((1E)-prop-1-enyl)phenoxy)-1-methylbutoxy)quinolin-2-amine;
methyl 2-((4-((2-aminoquinolin-8-yl)oxy)pentyl)oxy)-4-methoxybenzoate;
8-(4-(2-benzylphenoxy)-1-methylbutoxy)quinolin-2-amine;
8-(4-(2-fluoro-4-nitrophenoxy)-1-methylbutoxy)quinolin-2-amine;
5-acetyl-2-((4-((2-aminoquinolin-8-yl)oxy)pentyl)oxy)benzamide;
8-(4-(2,3-dihydro-1H-inden-5-yloxy)-1-methylbutoxy)quinolin-2-amine;
8-(4-(4-(1H-imidazol-1-yl)phenoxy)-1-methylbutoxy)quinolin-2-amine;
8-(4-(dibenzo[b,d]furan-2-yloxy)-1-methylbutoxy)quinolin-2-amine;
8-(4-((2,2-dimethyl-2,3-dihydro-1-benzofuran-7-yl)oxy)-1-methylbutoxy)quinolin-2-amine;
8-(4-(2-isoxazol-5-ylphenoxy)-1-methylbutoxy)quinolin-2-amine;
6-((4-((2-aminoquinolin-8-yl)oxy)pentyl)oxy)-1,3-benzoxathiol-2-one;
8-(4-(2-methoxy-4-propylphenoxy)-1-methylbutoxy)quinolin-2-amine;
8-(4-(2-chloro-3-(trifluoromethyl)phenoxy)-1-methylbutoxy)quinolin-2-amine;
8-(1-methyl-4-(2-methylphenoxy)butoxy)quinolin-2-amine;
8-(1-methyl-4-(3-methylphenoxy)butoxy)quinolin-2-amine;
8-(1-methyl-4-(4-methylphenoxy)butoxy)quinolin-2-amine;
8-(4-(2-chloro-5-methylphenoxy)-1-methylbutoxy)quinolin-2-amine;
4-((4-((2-aminoquinolin-8-yl)oxy)pentyl)oxy)phenol;
8-(4-(3-methoxyphenoxy)-1-methylbutoxy)quinolin-2-amine;
8-(4-(4-methoxyphenoxy)-1-methylbutoxy)quinolin-2-amine;

8-(4-(2-fluorophenoxy)-1-methylbutoxy)quinolin-2-amine;
8-(4-(3-fluorophenoxy)-1-methylbutoxy)quinolin-2-amine;
8-(4-(4-fluorophenoxy)-1-methylbutoxy)quinolin-2-amine;
8-(4-(2-chlorophenoxy)-1-methylbutoxy)quinolin-2-amine;
8-(4-(3-chlorophenoxy)-1-methylbutoxy)quinolin-2-amine;
8-(4-(4-chlorophenoxy)-1-methylbutoxy)quinolin-2-amine;
8-(4-(2-bromophenoxy)-1-methylbutoxy)quinolin-2-amine;
8-(4-(3-bromophenoxy)-1-methylbutoxy)quinolin-2-amine;
8-(4-(4-bromophenoxy)-1-methylbutoxy)quinolin-2-amine;
3-((4-((2-aminoquinolin-8-yl)oxy)pentyl)oxy)benzonitrile;
4-((4-((2-aminoquinolin-8-yl)oxy)pentyl)oxy)benzonitrile;
8-(1-methyl-4-(3-(trifluoromethyl)phenoxy)butoxy)quinolin-2-amine;
8-(1-methyl-4-(4-(trifluoromethyl)phenoxy)butoxy)quinolin-2-amine;
8-(1-methyl-4-(3-(trifluoromethoxy)phenoxy)butoxy)quinolin-2-amine;
8-(4-(2,3-dimethylphenoxy)-1-methylbutoxy)quinolin-2-amine;
8-(4-(2,4-dimethylphenoxy)-1-methylbutoxy)quinolin-2-amine;
8-(4-(2,5-dimethylphenoxy)-1-methylbutoxy)quinolin-2-amine;
8-(4-(3,4-dimethylphenoxy)-1-methylbutoxy)quinolin-2-amine;
8-(4-(3,5-dimethylphenoxy)-1-methylbutoxy)quinolin-2-amine;
8-(4-(1,3-benzodioxol-5-yloxy)-1-methylbutoxy)quinolin-2-amine;
8-(4-(2,3-dichlorophenoxy)-1-methylbutoxy)quinolin-2-amine;
8-(4-(2,4-dichlorophenoxy)-1-methylbutoxy)quinolin-2-amine;
8-(4-(2,5-dichlorophenoxy)-1-methylbutoxy)quinolin-2-amine;
8-(4-(3-isopropyl-5-methylphenoxy)-1-methylbutoxy)quinolin-2-amine;
8-(4-(3,4-dichlorophenoxy)-1-methylbutoxy)quinolin-2-amine;
N-methyl-8-(1,3,3-trimethylbutoxy)quinolin-2-amine;
N-propyl-8-(1,3,3-trimethylbutoxy)quinolin-2-amine;
8-(((1R)-1,3,3-trimethylbutyl)oxy)quinolin-2-amine;
8-(((1S)-1,3,3-trimethylbutyl)oxy)quinolin-2-amine;
N-((5-(2-(trifluoromethyl)phenyl)-2-furyl)methyl)-8-(1,3,3-trimethylbutoxy)quinolin-2-amine;
N-((5-(2-nitrophenyl)-2-furyl)methyl)-8-(1,3,3-trimethylbutoxy)quinolin-2-amine;
N-((5-(2-chlorophenyl)-2-furyl)methyl)-8-(1,3,3-trimethylbutoxy)quinolin-2-amine;
8-hexylquinolin-2-amine;
8-(1-methylpentyl)quinolin-2-amine;
8-(1-ethylbutyl)quinolin-2-amine;
8-(1-ethylpentyl)quinolin-2-amine;
8-cyclohexylquinolin-2-amine;
8-((5-((2-aminoquinolin-8-yl)oxy)pentyl)oxy)-quinolin-2-amine;
8-(3-((2-aminoquinolin-8-yl)oxy)butoxy)quinolin-2-amine;
8-(3-((2-aminoquinolin-8-yl)oxy)propoxy)-N-methylquinolin-2-amine;
8-((2E)-but-2-enyloxy)quinolin-2-amine;
3-methyl-8-(1,3,3-trimethylbutoxy)quinolin-2-amine;
2-(((8-(1,3,3-trimethylbutoxy)quinolin-2-yl)amino)carbonyl)benzyl benzoate;
N-(3-((2-aminoquinolin-8-yl)oxy)propyl)-8-(1,3,3-trimethylbutoxy)quinolin-2-amine;
8-(4-(2-chloro-4-methylphenoxy)-1-methylbutoxy)quinolin-2-amine;
8-(4-(2-(benzyloxy)phenoxy)-1-methylbutoxy)quinolin-2-amine;
8-(((3S)-1-(1,3-benzodioxol-5-ylmethyl)pyrrolidin-3-yl)oxy)quinolin-2-amine;
8-(((3S)-1-(2-fluorobenzyl)pyrrolidin-3-yl)oxy)quinolin-2-amine;
8-(((3S)-1-(1,1'-biphenyl-4-ylmethyl)pyrrolidin-3-yl)oxy)quinolin-2-amine;
8-(((3S)-1-((3-methyl-1-benzothien-2-yl)methyl)pyrrolidin-3-yl)oxy)quinolin-2-amine;
8-(((3S)-1-((2,2-dimethyl-3,4-dihydro-2H-chromen-6-yl)methyl)pyrrolidin-3-yl)oxy)quinolin-2-amine;
tert-butyl (3S)-3-((2-aminoquinolin-8-yl)oxy)pyrrolidine-1-carboxylate;
8-((3S)-pyrrolidin-3-yloxy)quinolin-2-amine;
8-(((3S)-1-(4-tert-butylbenzyl)pyrrolidin-3-yl)oxy)quinolin-2-amine;
8-(((3S)-1-(2,3-dihydro-1,4-benzodioxin-6-ylmethyl)pyrrolidin-3-yl)oxy)quinolin-2-amine;
8-(((3S)-1-(2,3-difluorobenzyl)pyrrolidin-3-yl)oxy)quinolin-2-amine;
8-(((3S)-1-(3-(trifluoromethyl)benzyl)pyrrolidin-3-yl)oxy)quinolin-2-amine;
8-(((3S)-1-((2,2-difluoro-1,3-benzodioxol-5-yl)methyl)pyrrolidin-3-yl)oxy)quinolin-2-amine;
8-(((3S)-1-(2,4-dimethylbenzyl)pyrrolidin-3-yl)oxy)quinolin-2-amine;
N-(2,3-dihydro-1,4-benzodioxin-6-ylmethyl)-8-(((3S)-1-(2,3-dihydro-1,4-benzodioxin-6-ylmethyl)pyrrolidin-3-yl)oxy)quinolin-2-amine;
4-((3-((2-aminoquinolin-8-yl)oxy)propyl)amino)-6-methyl-2H-chromen-2-one; and
4-((3-((2-aminoquinolin-8-yl)oxy)propyl)amino)-6-chloro-2H-chromen-2-one.

The present compounds can exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like. The present invention contemplates pharmaceutically suitable salts formed at the nitrogen attached to 2-amino group of formula (I), when $R_1$ is selected from hydrogen, alkyl, alkoxy, aryl, arylalkyl, heterocycle, heterocyclealkyl, $R_A R_B N$.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds can also exist as therapeutically suitable prodrugs. The term "therapeutically suitable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to the parent compounds of formula (I) for example, by hydrolysis in blood.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well-known in the art.

Geometric isomers can exist in the present compounds The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents. Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents which dissolve or disperse in the injectable media.

Antagonism of the effects of MCH through the MCH receptor by the compounds of the present invention can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders caused or exacerbated by MCH are treated or prevented in a patient by administering to the patient, a therapeutically effective amount of compound of the present invention in such an amount and for such time as is necessary to achieve the desired result. The term "therapeutically effective amount," refers to a sufficient amount of a compound to effectively emeliorate disorders mediated by MCH, by antagonizing the effect of MCH through the MCH receptor at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the present compounds in single or divided doses can be in amounts, for example, from 0.01 to 50 mg/kg body weight or more usually from 0.1 to 25 mg/kg body weight. In general, treatment regimens comprise administration to a patient in need of such treatment from about 10 mg to about 1000 mg of the compounds per day in single or multiple doses.

Determination of Biological Activity

Assay for Release of Intracellular Calcium:

Activation of the melanin concentrating hormone receptor (MCHR) by MCH induces the release of $Ca^{++}$ from intracellular stores. This intracellular calcium release is measured using a fluorometric imaging plate reader (FLIPR™, Molecular Devices Corp.) in conjunction with the $Ca^{++}$-sensitive dye Fluo-4. Release of $Ca^{++}$ from intracellular stores causes an increase in fluorescence of the dye that is proportional to $Ca^{++}$ concentration. Briefly, the assays are performed as follows. HEK293 cells expressing the murine MCHR are plated overnight at 50,000 cells/well in 96-well plates. The following day, culture medium is removed and replaced with 100 $\mu$l/well of D-PBS (+glucose and sodium pyruvate) containing 2.5 $\mu$M Fluo-4AM (Molecular Probes), 0.01% Pluronic F-127 and 2.5 mM probenecid. Cells are loaded with the Fluo-4 dye for at least one hour at room temp. After loading, the cells are washed gently to remove extracellular dye and 100 $\mu$l of D-PBS (+glucose and sodium pyruvate) is added to each well. Test compounds are prepared at 40 $\mu$M in 4% DMSO. The cell plate is placed in the FLIPR™ and 50 $\mu$l/well of test compound is delivered. The calcium signal is followed for 3 minutes to assay for potential agonist activity by the test compounds. Then 50 $\mu$l/well of 12 nM human MCH (in D-PBS containing 0.1% BSA) is added and the ligand-induced calcium signal is followed for an additional 3 minutes. Antagonist activity as determined by the test compounds ability to inhibit MHC induced $Ca^{++}$ flux is calculated as % inhibition as described by the following formula:

% inhibition=[1−((fTC−fB)÷(fMCH−fB))]×100.

fTC=MCH-induced fluorescence in the presence of test compound;
fMCH=MCH-induced fluorescence in the absence of test compound;
fB=Baseline fluorescence.
MCH (3 nM) usually elicits a response of 30,000–40,000 relative fluorescence units (RFU) with a baseline of ~1000 RFU. Fluo-4 fluorescence is measured at 488 nm, with an exposure of 0.40 sec. and F-stop=2.0 and the laser set at 0.40–0.60 W constant light output.

The compounds of the present invention inhibit MCH induced fluorescence at a dose of 10 $\mu$M. Preferably compounds of the present invention inhibit MCH induced fluorescence in a range of about 75 to about 100% inhibition of MCH at a dose of 10 $\mu$M. More preferably compounds of the present invention inhibit MCH induced fluorescence in a range of about 90 to about 100% inhibition of MCH at a dose of 10 $\mu$M.

As antagonists of MCH action upon the MCH receptor, therefore, the compounds of the present invention are useful in treating disorders that are mediated by MCH through the MCH receptor, such as obesity.

Synthetic Methods

Abbreviations which have been used in the descriptions of the scheme and the examples that follow are: m-CPBA for meta-chloroperoxy-benzoic acid; DMF for N,N-dimethylformamide; DMSO for dimethylsulfoxide; EDAC for 1-(3-dimethylaminopropyl)-3-ethylcarbodiimide hydrochloride; HOBT for 1-hydroxybenzotriazole hydrate; NMP for N-methylpyrrolidinone; THF for tetrahydrofuran; TFA for trifluoroacetic acid; and Pd(dppf)Cl$_2$ for (diphenylphospino)ferrocenyl palladium chloride.

The compounds and processes of the present invention will be better understood in connection with the following synthetic schemes which together illustrate the methods by which the compounds of the invention may be prepared. The synthesis of compounds of formula (I) wherein the groups $R_1$, $R_2$, $R_3$, $R_4$, $R_5$, and L are as defined above unless otherwise noted below, are exemplified below.

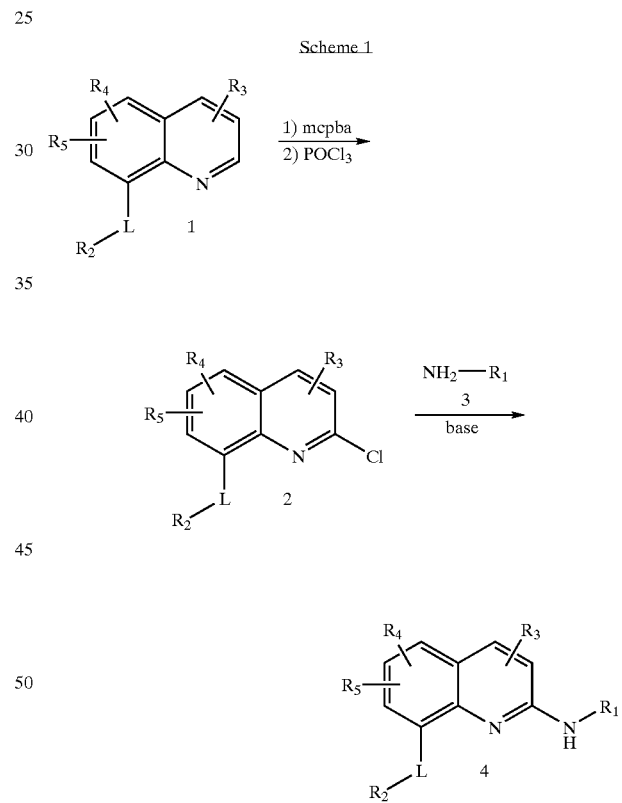

As shown in Scheme 1, compounds of formula 1 can be reacted with m-CPBA followed by a reaction with phosphorous oxychloride to provide compounds of formula 2. The reaction of compound of formula 1 with m-CPBA are generally carried out in solvents such as but not limited to chloroform, dichloromethane, benzene and the like and are generally done at 25° C. for 20 minutes. The further reaction with phosphorous oxychloride are generally carried out in solvents such as but not limited to chloroform, dichloromethane, benzene and the like and are generally done at 100° C. for 15 minutes. Compounds of formula 2 can then be reacted with amines of formula 3 in the presence of a base to provide compounds of formula 4. Typical bases used in the reaction include but are not limited to triethylamine, diisopropylethylamine and typical solvents include but not limited to tetrahydrofuran, acetonitrile and the like. Alternatively, bases such as sodium hydride in solvents such as but not limited to DMF may be utilized in the transformation.

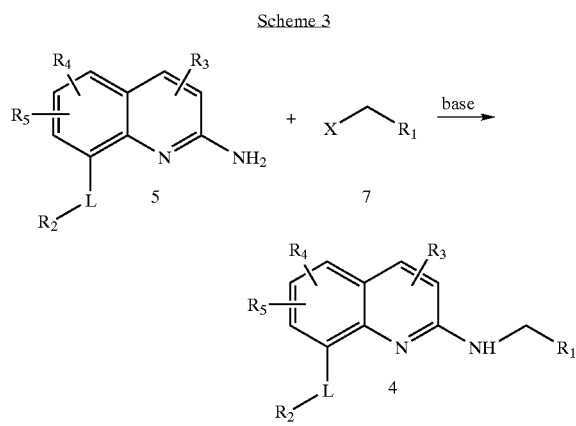

As shown in Scheme 2, compounds of general formula 5 can be reacted with aldehydes of general formula 6 in the presence of a reducing agent such as but not limited to sodium cyanoborohydride, sodium borohydride and sodium triacetoxyborohydride in solvents such as but not limited to THF and the like to provide compounds of formula 4. Reactions are performed at temperatures ranging from 25 to 80° C. and are generally complete between 5 and 96 hours.

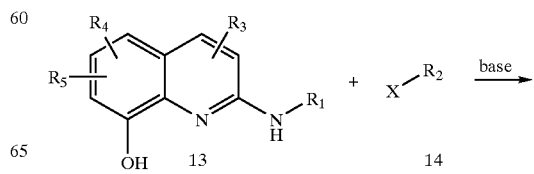

As shown in Scheme 3, compounds of general formula 5 can be reacted with compounds of formula 7 (wherein X is halogen) in the presence of a base to provide compounds of formula 4. The reactions are typically carried out at 60° C. in solvents including but not limited to acetonitrile, DMF, THF and the like, and reactions are generally complete within 6–18 hours.

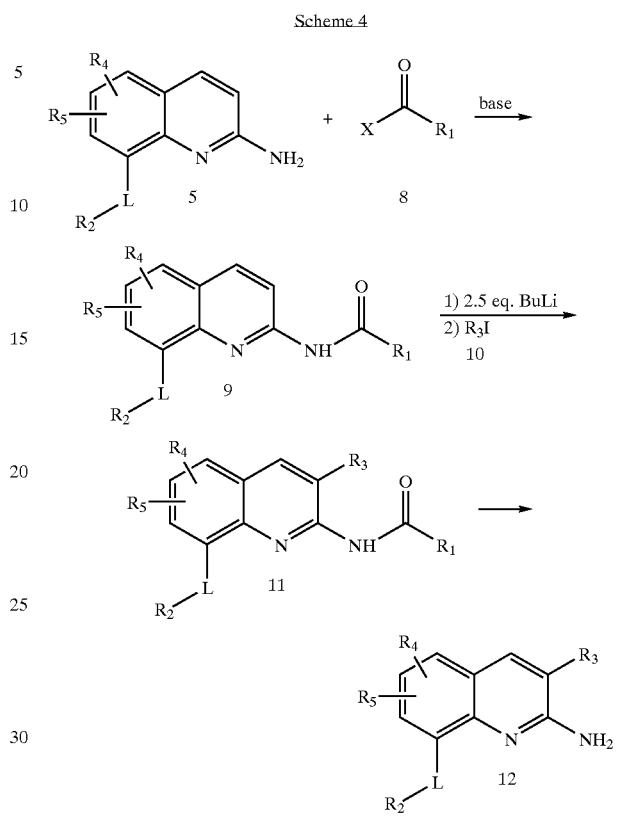

As shown in Scheme 4, compounds of formula 5 wherein L is selected from the group consisting of —O—, —S—, or a covalent bond, can be reacted with compounds of formula 8 wherein $R_1$ is alkyl, aryl, arylalkyl, heterocycle and heterocyclealkyl in the presence of a base to provide compounds of formula 9. Typical bases include but are not limited to triethylamine, diisopropylethylamine and the like. Reactions are typically carried out at 25° C. for 1–10 hours. Compounds of formula 9 can be reacted with an excess of butyl lithium at −78° C. for 4 hours in solvents including but not limited to THF followed by the reaction with compounds of formula 10, wherein $R_3$ is alkyl, to provide compounds of formula 11. Compounds of formula 11 can be reacted with reagents commonly known to those skilled in the art which are useful for the hydrolysis of amides to provide compounds of formula 12. Such reagents and conditions useful for the hydrolysis of amides include but are not limited to sodium or potassium hydroxide in aqueous solvent mixtures such as but not limited to aqueous isopropanol and aqueous tetrahydrofuran and the like. Reactions may or may not need to be heated to 50–70° C. for 1–10 hours.

-continued

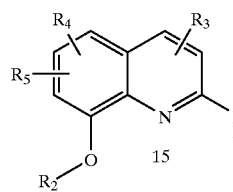

As shown in Scheme 5, compounds of formula 13 can be reacted with compounds of formula 14 in the presence of a base such as but not limited to triethylamine, diisopropylethylamine and the like to provide compounds of formula 15. Typical reaction conditions may involve heating to 50° C. in such solvents that include but are not limited to acetonitrile, THF and DMF. Alternatively, sodium hydride in DMF may be utilized for this transformation.

Scheme 6

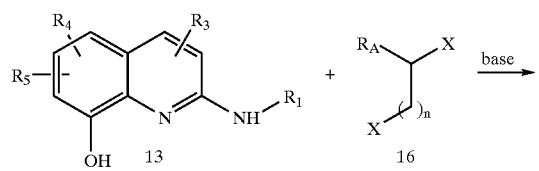

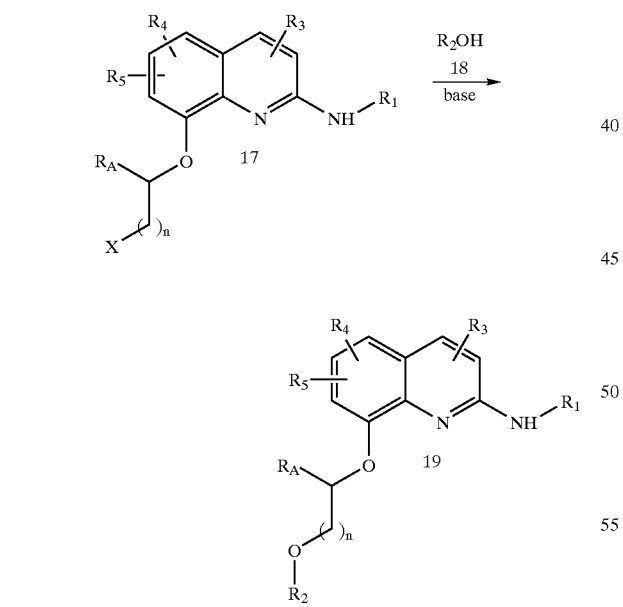

As shown in Scheme 6, compounds of formula 13 can be reacted under the same conditions as described in Scheme 5 with compounds of formula 16 (wherein n is between 0 and 3) to provide compounds of formula 17. Compounds of formula 17 can be further reacted under the same conditions with compounds of formula 18 to provide compounds of formula 19.

Scheme 7

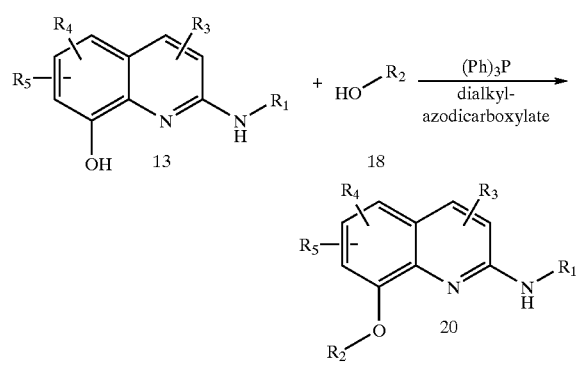

As shown in Scheme 7, compounds of formula 13 can be reacted with compounds of formula 18 in the presence of triphenylphosphine and a dialkyl azodicarboxylate such as but not limited to dimethyl azodicarboxylate, diethyl azodicarboxylate, diisopropyl azodicarboxylate and dicyclohexyl azodicarboxylate at 0° C. in solvents such as but not limited to THF, diethyl ether and the like to provide compounds of formula 20.

Scheme 8

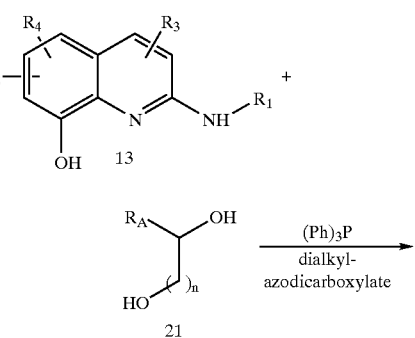

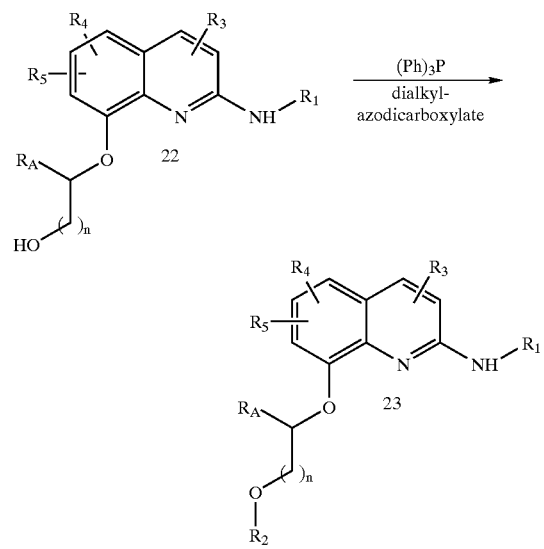

As shown in Scheme 8, compounds of formula can be reacted under the same conditions as described in Scheme 7 with compounds of formula 21 to provide compounds of formula 22. Compounds of formula 22 can be further reacted under the same conditions with compounds of formula 13 or with compounds of formula 18 to provide compounds of formula 23.

Scheme 9

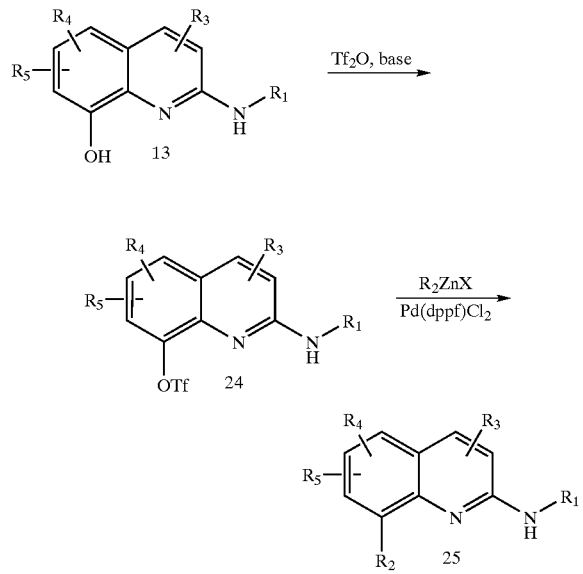

As shown in Scheme 9, compounds of formula 13 can be reacted with trifluoromethanesulfonic anhydride and a base to provide compounds of formula 24. Typical reactions utilize bases such as but not limited to triethylamine, diisopropylethylamine and the like and are carried out in solvents including but not limited to THF and dichloromethane and are generally done at 0° C. Compounds of formula 24 can be reacted with organozinc reagents represented by the formula $R_2ZnX$ (wherein $R_2$ is alkyl, alkenyl, alkoxyalkyl, aryl, arylalkyl, aryloxyalkyl, cycloalkyl, cycloalkylalkyl, heterocycle, heterocyclealkyl, heterocycleoxyalkyl, and X represents a halogen) in the presence of $Pd(dppf)Cl_2$ to provide compounds of formula 25.

Scheme 10

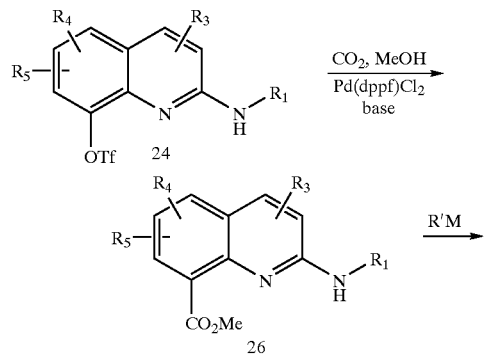

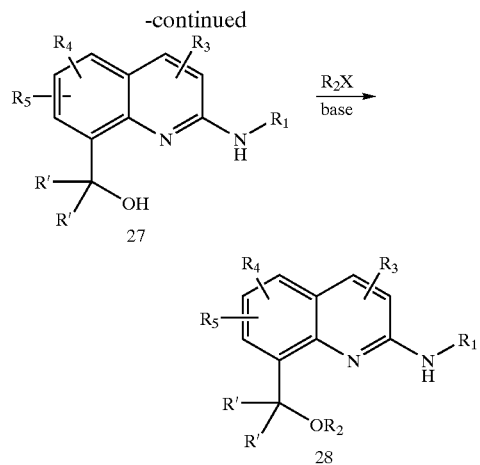

As shown in Scheme 10, compounds of formula 24 can be reacted with carbon dioxide in the presence of $Pd(dppf)Cl_2$ and a base in methanol to provide compounds of formula 26. Compounds of formula 26 can be reacted with compounds of formula R'M (wherein R' is alkyl, alkoxy, aryl, cycloalkyl; and M is lithium or magnesium bromide) to provide compounds of formula 27. Compounds of formula 27 can be reacted with compounds of formula $R_2X$, (wherein $R_2$ is previously described in formula (I), but is not hydrogen; and X is halogen) and a base to provide compounds of formula 28. Typical bases utilized in the transformation of compounds of formula 27 to compounds of formula 28 include but are not limited to sodium hydride in DMF and potassium hydroxide in dimethyl sulfoxide.

Scheme 11

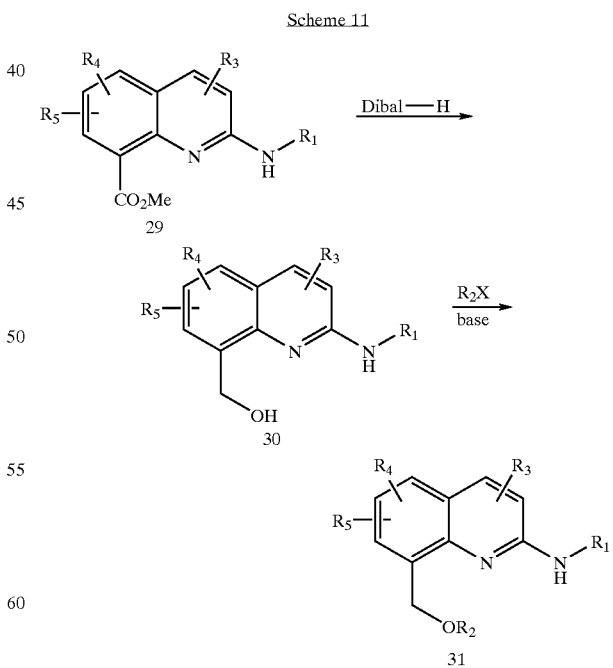

As shown in Scheme 11, compounds of formula 29 can be reacted with Dibal-H in THF at 0° C. to provide compounds of formula 30. Compounds of formula 30 can be reacted with compounds of formula R₂X using conditions described in Scheme 10 to provide compounds of formula 31.

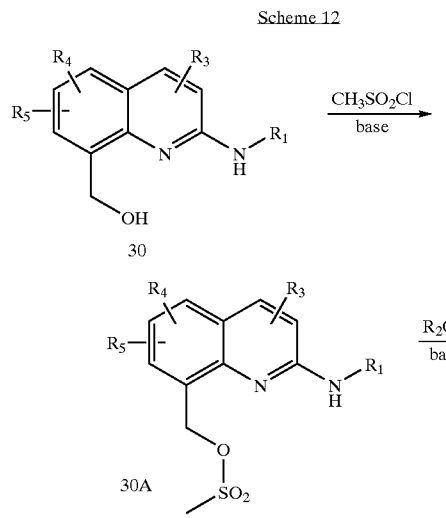

Alternatively, compounds of formula 30 can be reacted with methanesulfonyl chloride in the presence of a base such as but not limited to triethylamine, diisopropylethylamine, N-methylmorpholine and the like in solvents such as but not limited to dichloromethane and THF to provide compounds of general formula 30 A. Compounds of formula 30 A can be reacted with alcohols of formula 18 in the presence of a base such as but not limited to triethylamine, diisopropylethylamine and the like in solvents such as but not limited to THF, acetonitrile and the like to provide compounds of general formula 31.

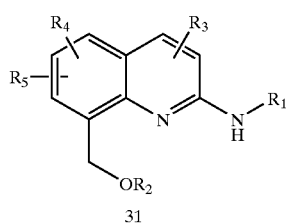
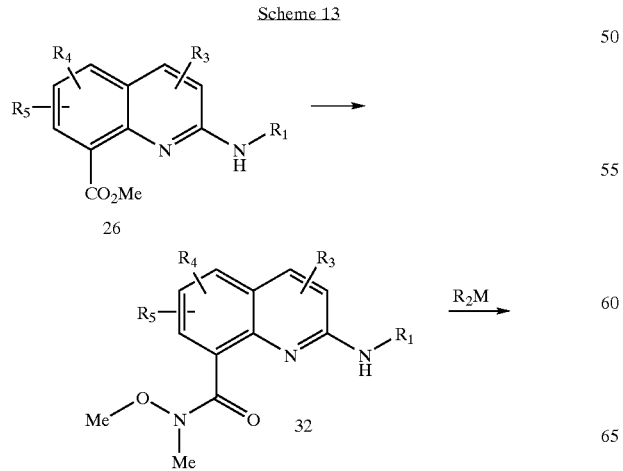

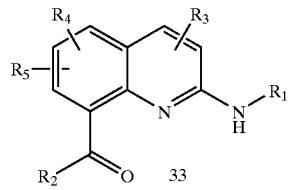

As shown in scheme 13, compounds of formula 26 can also be converted to compounds of formula 32 through hydrolysis of the ester functionality to provide the carboxylic acid which can be converted to the amide 32 through methods commonly known to those skilled in the art. The conversion of the amide 32 to compounds of formula 33 by the addition of organometallic reagents wherein R₂ is alkyl, alkenyl, alkoxyalkyl, aryl, arylalkyl, aryloxyalkyl, cycloalkyl, cycloalkylalkyl, heterocycle, heterocyclealkyl, heterocycleoxyalkyl, and M is magnesium bromide is well known to those skilled in the art.

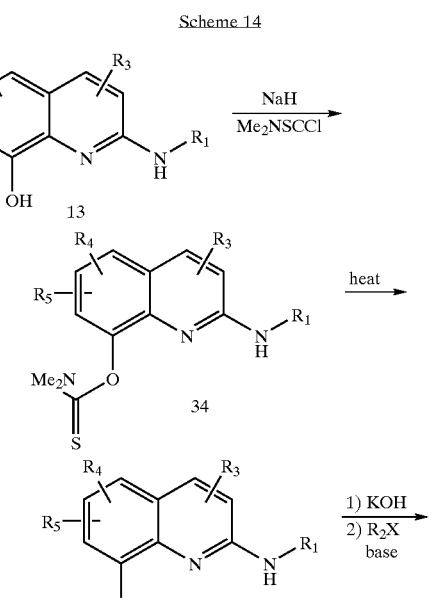
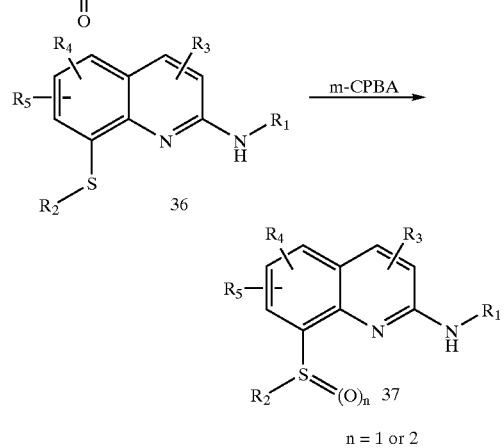

n = 1 or 2

As shown in scheme 14, compounds of formula 13 can be reacted with sodium hydride in solvents such as but not limited to THF and DMF followed be a reaction with dimethylthiocarbamoyl chloride to provide compounds of formula 34. Compounds of formula 32 can then be heated to provide compounds of formula 35. Compounds of formula 35 can be reacted with potassium hydroxide to hydrolyze the carbamoyl functionality followed by a reaction with $R_2X$ with a base to provide compounds of formula 36. Compounds of formula 36 can be reacted with meta-chloroperoxybenzoic acid to provide either the compounds of formula 37, wherein n is either 1 or 2. The product of the oxidation with m-CPBA to provide sulfone or the sulfoxide has been established in the literature and is known to those skilled in the art.

As shown in Scheme 15, compounds of general formula 13 can be reacted with heterocycles of general formula 38 using the same conditions described in Scheme 7 to provide compounds of general formula 39, wherein P is a nitrogen protecting group such as but not limited to acetyl, benzyl, tert-butoxycarbamate, benzylcarbamate and allylcarbamate. Compounds of general formula 39 can be reacted under conditions known to those skilled in the art to remove nitrogen protecting groups to provide compounds of general formula 40. The nitrogen protecting groups used in the compounds described within are specific to the protecting group used for each example and can be found in the description in Greenes "Protecting groups in Organic Chemistry" $3^{rd}$ ed. 1999, Wiley & Sons, Inc. A typical protecting group used in these examples described within is tert-butoxycarbonyl which can be removed by the reaction with either 4N HCl in dioxane or trifluoroacetic acid in dichloromethane. Compounds of general formula 40 can be reacted with compounds of general formula 41, wherein $R_7$, $L_2$ are defined in formula (I), r is 1, 2, or 3 and X is halogen with a base such as but not limited to triethylamine, diisopropylethylamine and the like in solvents such as but not limited to THF, acetonitrile and the like to provide compounds of general formula 42.

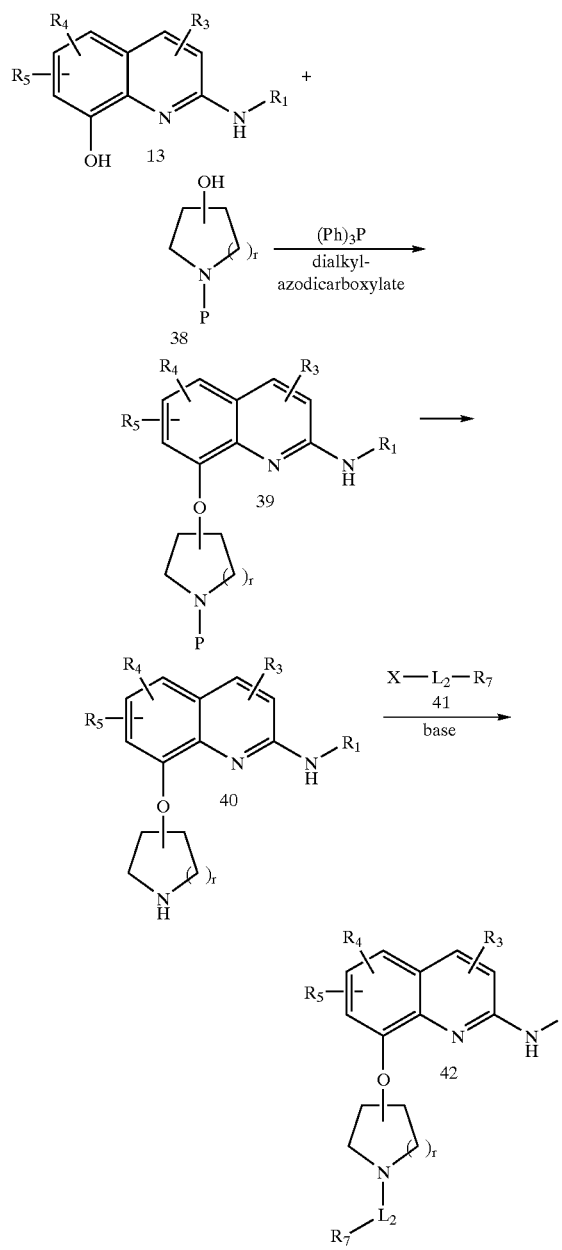

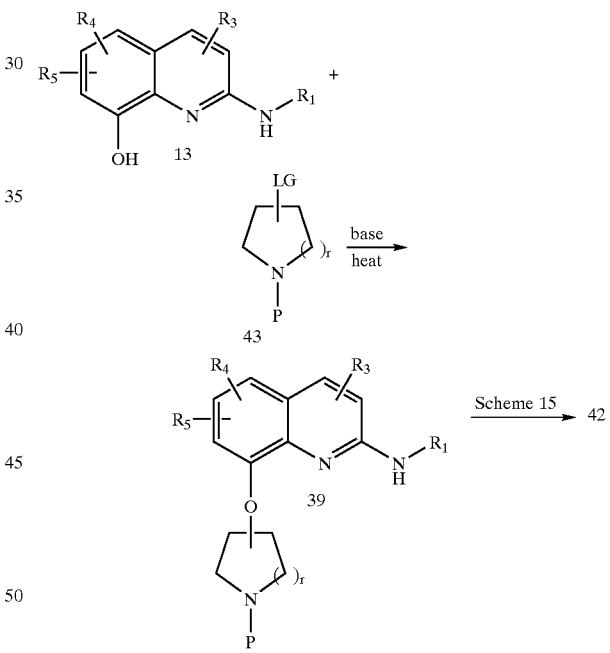

Alternatively, compounds of general formula 13 can be reacted with compounds of general formula 43 wherein LG is a leaving group such as but not limited to mesyl, triflic, or halogen, in the presence of a base such as but not limited to triethylamine, diisopropylethylamine and the like under heating conditions to provide compounds of general formula 39. Typical conditions for this reaction include heating the reaction mixture to 65° C. in solvents such as but not limited to THF or acetonitrile for 12 to 24 hours. Compounds of general formula 39 can then be reacted under conditions described in Scheme 15 to provide compounds of general formula 42.

The present invention will now be described in connection with certain embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments.

Compounds of the invention were named by ACD/ChemSketch version 5.01 (developed by Advanced Chemistry Development, Inc., Toronto, ON, Canada) or were given names which appeared to be consistent with ACD nomenclature.

EXPERIMENTALS

Example 1

8-isopropoxyquinolin-2-amine

A reaction vessel of the PE Biosystems Solaris 530™ Organic Synthesizer was charged with PS-PPh$_3$ resin (Aldrich Chemical Co., Inc, 176 mg, 4.2 equiv for reactions involving a secondary alcohol; 88 mg, 2.1 equiv for reactions involving a primary alcohol), and purged by passing a stream of N$_2$ for 45 seconds. A solution of 2-amino-8-hydroxyquinoline (1.50 mL; 13.3 mg/mL) in anhydr. THF was added to the vessel and the resultant suspension was shaken for 15 min. Then, a solution of DBAD (0.50 mL; 46 mg/mL; 1.6 equiv) in anhydr. THF was added and the contents of the flask were shaken for 10 min. A solution of isopropylalcohol (0.105 mL, 0.300 mM; 1.25 equiv) in anhydr. THF was then added and the resulting suspension was shaken at room temperature for 4 h. After this time for reactions involving secondary alcohols, the addition of DBAD and the alcohol was repeated and the agitation of all reactions was maintained for an additional 6 h. The resultant suspension was filtered, and the resin washed with THF (2.5, 3.5 and 3.0 mL). The filtrate and washings were combined and evaporated in vacuo. The resulting crude product was then treated with 4.0 mL of 4 M HCl in dioxane at room temperature for 4 h. The resulting solution was evaporated in vacuo. The residue was dissolved in 1.5 mL of a 1:1 mixture of DMSO/MeOH and purified by preparative reverse-phase HPLC. $^1$H NMR (500 MHz, CDCl$_3$) δ ppm 7.96 (d, 1H), 7.30 (m, 1H), 7.20 (m, 1H), 7.12 (m, 1H), 7.08 (d, 1H), 4.78 (m, 1H), 1.49 (d, 6H); MS (DCI/NH$_3$) m/z 203 [M+H]$^+$.

Example 2

8-(cyclobutyloxy)quinolin-2-amine

The title compound was prepared according to the procedure described in Example 1 substituting cyclobutanol for isopropylalcohol. $^1$H NMR (500 MHz, CDCl$_3$) δ ppm 7.94 (d, 1H), 7.94 (d, 1H), 7.27 (m, 1H), 7.19 (m, 1H), 7.08 (m, 1H), 4.82 (m, 1H), 2.48 (m, 4H), 1.95 (m, 1H), 1.73 (m, 1H); MS (DCI/NH$_3$) m/z 215 [M+H]$^+$.

Example 3

8-sec-butoxyguinolin-2-amine

The title compound was prepared according to the procedure described in Example 1 substituting 2-butanol 1 for isopropylalcohol. $^1$H NMR (500 MHz, CDCl$_3$) δ ppm 7.94 (d, 1H), 7.29 (m, 1H), 7.19 (m, 1H), 7.11 (m, 1H), 7.07 (d, 1H), 4.38–4.58 (m, 1H), 2.00 (m, 1H), 1.73 (m, 1H), 1.43 (d, 3H), 1.01 (t, 3H); MS (DCI/NH$_3$) m/z 217 [M+H]$^+$.

Example 4

8-(cyclopentyloxy)quinolin-2-amine

The title compound was prepared according to the procedure described in Example 1 substituting cyclopentanol for isopropylalcohol. $^1$H NMR (500 MHz, CDCl$_3$) δ ppm 7.96 (d, 1H), 7.30 (m, 1H), 7.19 (m, 1H), 7.09 (m, 1H), 7.04 (d, 1H), 4.94 (m, 1H), 2.13 (m, 2H), 1.97 (m, 4H), 1.64 (m, 2H); MS (DCI/NH$_3$) m/z 229 [M+H]$^+$.

Example 5

8-(1-methylbutoxy)quinolin-2-amine

The title compound was prepared according to the procedure described in Example 1 substituting 2-pentanol 1 for isopropylalcohol. $^1$H NMR (500 MHz, CDCl$_3$) δ ppm 7.96 (d, 1H), 7.30 (t, 1H), 7.19 (d, 1H), 7.11 (d, 1H), 7.08 (d, 1H), 4.60 (m, 1H), 2.01 (m, 1H), 1.69 (m, 1H), 1.51 (m, 1H), 1.42 (d, 3H), 1.41 (m, 1H), 0.94 (t, 3H); MS (DCI/NH$_3$) m/z 231 [M+H]$^+$.

Example 6

8-(1,2-dimethylpropoxy)quinolin-2-amine

The title compound was prepared according to the procedure described in Example 1 substituting 3-methyl-2-butanol for isopropylalcohol. $^1$H NMR (500 MHz, CDCl$_3$) δ ppm 7.94 (d, 1H), 7.29 (t, 1H), 7.18 (d, 1H), 7.11 (m, 2H), 4.34 (m, 1H), 2.21 (m, 1H), 1.38 (d, 3H), 1.05 (d, 3H), 1.01 (d, 3H); MS (DCI/NH$_3$) m/z 231 [M+H]$^+$.

Example 7

8-(1-ethylpropoxy)quinolin-2-amine

The title compound was prepared according to the procedure described in Example 1 substituting 3-pentanol for isopropylalcohol. $^1$H NMR (500 MHz, CDCl$_3$) δ ppm 7.95 (d, 1H), 7.29 (t, 1H), 7.19 (m, 1H), 7.10 (m, 2H), 4.34 (m, 1H), 1.93 (m, 2H), 1.79 (m, 2H), 0.99 (t, 6H); MS (DCI/NH$_3$) m/z 231 [M+H]$^+$.

Example 8

8-(2-methoxy-1-methylethoxy)quinolin-2-amine

The title compound was prepared according to the procedure described in Example 1 substituting 1-methoxy-2-propanol for isopropylalcohol. $^1$H NMR (500 MHz, CDCl$_3$) δ ppm 7.95 (d, 1H), 7.30 (m, 1H), 7.21 (m, 2H), 7.05 (d, 1H), 4.76 (m, 1H), 3.93 (dd, 1H), 3.60 (dd, 1H), 3.41 (s, 3H), 1.42 (d, 3H); MS (DCI/NH$_3$) m/z 233 [M+H]$^+$.

Example 9

8-(cyclohexyloxy)quinolin-2-amine

The title compound was prepared according to the procedure described in Example 1 substituting cyclohexanol for isopropylalcohol. $^1$H NMR (500 MHz, CDCl$_3$) δ ppm 7.94 (d, 1H), 7.28 (t, 1H), 7.18 (d, 1H), 7.13 (d, 1H), 7.09 (d, 1H), 4.42 (m, 1H), 2.10 (m, 2H), 1.90 (m, 2H), 1.76 (m, 2H), 1.62 (m, 1H), 1.26–1.47 (m, 3H); MS (DCI/NH$_3$) m/z 243 [M+H]$^+$.

Example 10

8-((3-methylcyclopentyl)oxy)quinolin-2-amine

The title compound was prepared according to the procedure described in Example 1 substituting 3-methylcyclopentanol for isopropylalcohol. $^1$H NMR (500 MHz, CDCl$_3$) δ ppm 7.96 (d, 1H), 7.28 (t, 1H), 7.19 (m, 1H), 7.05 (m, 2H), 4.97 (m, 0.6H), 4.90 (m, 0.4H), 2.40 (m, 1H), 2.26 (m, 1.6H), 1.93–2.16 (m, 1.8H), 1.81 (m, 0.4H), 1.70 (m, 0.4H), 1.57 (m, 0.4H), 1.46 (m, 0.8H), 1.17 (m, 0.6H), 1.10 (d, 1.2H), 1.03 (d, 1.8H); MS (DCI/NH$_3$) m/z 243 [M+H]$^+$.

Example 11

8-((2-methylcyclohexyl)oxy)quinolin-2-amine

The title compound was prepared according to the procedure described in Example 1 substituting 2-methylcyclohexanol for isopropylalcohol. $^1$H NMR (500 MHz, CDCl$_3$) δ ppm 7.92 (d, 1H), 7.28 (d, 1H), 7.13 (m, 3H), 4.60 (m, 0.25H), 3.99 (td, 0.75H), 1.91–2.18 (m, 2.25H), 1.85 (m, 1.5H), 1.49–1.77 (m, 2.25H), 1.24–1.47 (m, 2.5H), 1.13 (m, 0.75H), 1.04 (d, 2.25H); MS (DCI/NH$_3$) m/z 257 [M+H]$^+$.

Example 12

8-(2-ethoxy-1-methylethoxy)quinolin-2-amine

The title compound was prepared according to the procedure described in Example 1 substituting 1-ethoxy-2-propanol for isopropylalcohol. $^1$H NMR (500 MHz, CDCl$_3$) δ ppm 7.95 (d, 1H), 7.30 (t, 1H), 7.23 (d, 1H), 7.21 (d, 1H), 7.06 (d, 1H), 4.76 (m, 1H), 3.92 (dd, 1H), 3.64 (dd, 1H), 3.57 (m, 2H), 1.43 (d, 3H), 1.15 (t, 3H); MS (DCI/NH$_3$) m/z 247 [M+H]$^+$.

Example 13

8-((3-methylcyclohexyl)oxy)quinolin-2-amine

The title compound was prepared according to the procedure described in Example 1 substituting 3-methylcyclohexanol for isopropylalcohol. Mixture of isomers. $^1$H NMR (500 MHz, CDCl$_3$) δ ppm 7.95 (m, 1H), 7.30 (m, 1H), 7.12 (m, 3H), 4.79 (m, 0.45H), 4.41 (m, 0.55H), 2.11 (m, 2.45H), 1.90 (m, 1H), 1.75 (m, 0.45H), 1.28–1.70 (m, 4.1H), 1.06 (m, 0.55H), 0.97 (d, 1.65H), 0.96 (m, 0.45H), 0.92 (d, 1.35H); MS (DCI/NH$_3$) m/z 257 [M+H]$^+$.

Example 14

8-((4-methylcyclohexyl)oxy)quinolin-2-amine

The title compound was prepared according to the procedure described in Example 1 substituting 4-methylcyclohexanol for isopropylalcohol. $^1$H NMR (500 MHz, CDCl$_3$) δ ppm 7.95 (m, 1H), 7.29 (m, 1H), 7.19 (m, 1H), 7.10 (m, 2H), 4.62 (m, 0.6H), 4.37 (m, 0.4H), 2.16 (m, 2H), 1.67–1.88 (m, 2.6H), 1.45–1.66 (m, 3.4H), 1.06 (m, 0.6H), 0.99 (m, 0.4H), 0.98 (d, 1.8H), 0.93 (m, 1.2H); MS (DCI/NH$_3$) m/z 257 [M+H]$^+$.

Example 15

8-(cycloheptyloxy)quinolin-2-amine

The title compound was prepared according to the procedure described in Example 1 substituting cycloheptanol for isopropylalcohol. $^1$H NMR (500 MHz, CDCl$_3$) δ ppm 7.94 (d, 1H), 7.29 (t, 1H), 7.17 (d, 1H), 7.07 (m, 2H), 4.60 (m, 1H), 2.08 (m, 4H), 1.82 (m, 2H), 1.63 (m, 4H), 1.46 (m, 2H); MS (DCI/NH$_3$) m/z 257 [M+H]$^+$.

Example 16

8-(1,3,3-trimethylbutoxy)quinolin-2-amine

The title compound was prepared according to the procedure described in Example 1 substituting 4,4-dimethyl-2-pentanol for isopropylalcohol. $^1$H NMR (500 MHz, CDCl$_3$) δ ppm 7.95 (d, 1H), 7.31 (t, 1H), 7.19 (d, 1H), 7.15 (d, 1H), 7.09 (d, 1H), 4.73 (m, 1H), 2.30 (dd, 1H), 1.49 (dd, 1H), 1.39 (d, 3H), 0.96 (s, 9H); MS (DCI/NH$_3$) m/z 259 [M+H]$^+$.

Example 17

8-(2-ethyl-1-methylbutoxy)quinolin-2-amine

The title compound was prepared according to the procedure described in Example 1 substituting 3-ethyl-2-pentanol for isopropylalcohol. $^1$H NMR (500 MHz, CDCl$_3$) δ ppm 7.95 (d, 1H), 7.29 (t, 1H), 7.18 (d, 1H), 7.11 (d, 1H), 7.09 (d, 1H), 4.61 (m, 1H), 1.82 (m, 1H), 1.66 (m, 1H), 1.54 (m, 2H), 1.39 (d, 3H), 1.32 (m, 1H), 0.94 (t, 3H), 0.89 (t, 3H); MS (DCI/NH$_3$) m/z 259 [M+H]$^+$.

Example 18

8-ethoxyquinolin-2-amine

The title compound was prepared according to the procedure described in Example 1 ethanol for isopropylalcohol. $^1$H NMR (500 MHz, CDCl$_3$) δ ppm 7.96 (d, 1H), 7.30 (t, 1H), 7.21 (m, 1H), 7.09 (m, 2H), 4.25 (q, 2H), 1.58 (t, 3H); MS (DCI/NH$_3$) m/z 189 [M+H]$^+$.

Example 19

8-propoxyquinolin-2-amine

The title compound was prepared according to the procedure described in Example 1 substituting 1-propanol for isopropylalcohol. $^1$H NMR (500 MHz, CDCl$_3$) δ ppm 7.96 (d, 1H), 7.30 (t, 1H), 7.21 (m, 1H), 7.08 (m, 2H), 4.13 (t, 2H), 2.01 (m, 2H), 1.09 (t, 3H); MS (DCI/NH$_3$) m/z 203 [M+H]$^+$.

Example 20

8-butoxyquinolin-2-amine

The title compound was prepared according to the procedure described in Example 1 substituting 1-butanol for isopropylalcohol. $^1$H NMR (500 MHz, CDCl$_3$) δ ppm 7.96 (d, 1H), 7.30 (t, 1H), 7.21 (d, 1H), 7.09 (d, 1H), 7.09 (d, 1H), 4.17 (t, 2H), 1.97 (m, 2H), 1.53 (m, 2H), 0.99 (t, 3H); MS (DCI/NH$_3$) m/z 217 [M+H]$^+$.

Example 21

8-isobutoxyquinolin-2-amine

The title compound was prepared according to the procedure described in Example 1 substituting isobutyl alcohol for isopropylalcohol. $^1$H NMR (500 MHz, CDCl$_3$) δ ppm 7.95 (d, 1H), 7.30 (t, 1H), 7.20 (m, 1H), 7.09 (m, 2H), 3.92 (d, 2H), 2.37 (m, 1H), 1.09 (d, 6H); MS (DCI/NH$_3$) m/z 217 [M+H]$^+$.

Example 22

8-(cyclobutylmethoxy)quinolin-2-amine

The title compound was prepared according to the procedure described in Example 1 substituting cyclobutylmethanol for isopropylalcohol. $^1$H NMR (500 MHz, CDCl$_3$) δ ppm 7.95 (d, 1H), 7.30 (t, 1H), 7.20 (m, 1H), 7.07 (m, 2H), 4.16 (d, 2H), 3.05 (m, 1H), 2.25 (m, 2H), 1.78–2.07 (m, 4H); MS (DCI/NH$_3$) m/z 229 [M+H]$^+$.

Example 23

8-(2-cyclopropylethoxy)quinolin-2-amine

The title compound was prepared according to the procedure described in Example 1 substituting 2-cyclopropylethanol for isopropylalcohol. $^1$H NMR (500 MHz, CDCl$_3$) δ ppm 7.98 (d, 1H), 7.32 (t, 1H), 7.22 (d, 1H), 7.13 (d, 1H), 7.06 (d, 1H), 4.25 (t, 2H), 1.88 (m, 2H), 0.93 (m, 1H), 0.48 (m, 2H), 0.15 (m, 2H); MS (DCI/NH$_3$) m/z 229 [M+H]$^+$.

Example 24

8-(pentyloxy)quinolin-2-amine

The title compound was prepared according to the procedure described in Example 1 substituting 1-pentanol for isopropylalcohol. $^1$H NMR (500 MHz, CDCl$_3$) δ ppm 7.97 (d, 1H), 7.30 (t, 1H), 7.21 (d, 1H), 7.10 (d, 1H), 7.07 (d, 1H), 4.16 (t, 2H), 2.00 (m, 2H), 1.43 (m, 4H), 0.93 (t, 3H); MS (DCI/NH$_3$) m/z 231 [M+H]$^+$.

Example 25

8-(2-methylbutoxy)quinolin-2-amine

The title compound was prepared according to the procedure described in Example 1 substituting 2-methyl-1-butanol for isopropylalcohol. $^1$H NMR (500 MHz, CDCl$_3$) δ ppm 7.96 (d, 1H), 7.30 (t, 1H), 7.21 (d, 1H), 7.08 (m, 2H), 4.05 (m, 1H), 3.91 (m, 1H), 2.18 (m, 1H), 1.61 (m, 1H), 1.34 (m, 1H), 1.09 (d, 3H), 0.97 (t, 3H); MS (DCI/NH$_3$) m/z 231 [M+H]$^+$.

Example 26

8-(3-methylbutoxy)quinolin-2-amine

The title compound was prepared according to the procedure described in Example 1 substituting isoamylalcohol for isopropylalcohol. $^1$H NMR (500 MHz, CDCl$_3$) δ ppm 7.96 (d, 1H), 7.30 (t, 1H), 7.21 (d, 1H), 7.07 (d, 1H), 4.20 (t, 2H), 1.88 (m, 3H), 0.98 (d, 6H); MS (DCI/NH$_3$) m/z 231 [M+H]$^+$.

Example 27

8-(2-(methylthio)ethoxy)quinolin-2-amine

The title compound was prepared according to the procedure described in Example 1 substituting 2-(methylthio)ethanol for isopropylalcohol. $^1$H NMR (500 MHz, CDCl$_3$) δ ppm 7.98 (d, 1H), 7.32 (t, 1H), 7.26 (m, 1H), 7.14 (d, 1H), 7.06 (d, 1H), 4.34 (t, 2H), 3.13 (t, 2H), 2.22 (s, 3H); MS (DCI/NH$_3$) m/z 235 [M+H]$^+$.

Example 28

8-(cyclopentylmethoxy)quinolin-2-amine

The title compound was prepared according to the procedure described in Example 1 substituting cyclopentylmethanol for isopropylalcohol. $^1$H NMR (500 MHz, CDCl$_3$) δ ppm 7.95 (d, 1H), 7.29 (t, 1H), 7.20 (d, 1H), 7.10 (d, 1H), 7.07 (d, 1H), 4.04 (d, 2H), 2.65 (m, 1H), 1.97 (m, 2H), 1.64 (m, 4H), 1.30 (m, 2H); MS (DCI/NH$_3$) m/z 243 [M+H]$^+$.

Example 29

8-(tetrahydrofuran-3-ylmethoxy)quinolin-2-amine

The title compound was prepared according to the procedure described in Example 1 substituting tetrahydro-3-furanmethanol for isopropylalcohol. $^1$H NMR (500 MHz, CDCl$_3$) δ ppm 7.99 (d, 1H), 7.31 (t, 1H), 7.25 (d, 1H), 7.11 (d, 1H), 7.05 (d, 1H), 4.09 (m, 2H), 3.96 (m, 2H), 3.78 (m, 2H), 3.11 (m, 1H), 2.28 (m, 1H), 1.73 (m, 1H); MS (DCI/NH$_3$) m/z 245 [M+H]$^+$.

Example 30

8-(hexyloxy)quinolin-2-amine

The title compound was prepared according to the procedure described in Example 1 substituting 1-hexanol for isopropylalcohol. $^1$H NMR (500 MHz, CDCl$_3$) δ ppm 7.96 (d, 1H), 7.30 (t, 1H), 7.21 (d, 1H), 7.09 (m, 2H), 4.16 (t, 2H), 2.00 (m, 2H), 1.49 (m, 2H), 1.35 (m, 4H), 0.91 (m, 3H); MS (DCI/NH$_3$) m/z 245 [M+H]$^+$.

Example 31

8-(3,3-dimethylbutoxy)quinolin-2-amine

The title compound was prepared according to the procedure described in Example 1 substituting 3,3-dimethylbutanol for isopropylalcohol. $^1$H NMR (500 MHz, CDCl$_3$) δ ppm 7.96 (d, 1H), 7.30 (t, 1H), 7.21 (m, 1H), 7.10 (m, 2H), 4.23 (t, 2H), 1.99 (t, 2H), 1.01 (s, 9H); MS (DCI/NH$_3$) m/z 245 [M+H]$^+$.

Example 32

8-(3,3,3-trifluoropropoxy)quinolin-2-amine

The title compound was prepared according to the procedure described in Example 1 substituting 3,3,3-trifluoropropan-1-ol for isopropylalcohol. $^1$H NMR (500 MHz, CDCl$_3$) δ ppm 8.03 (d, 1H), 7.36 (t, 1H), 7.31 (m, 1H), 7.15 (m, 1H), 7.01 (d, 1H), 4.39 (t, 2H), 3.05 (m, 2H); MS (DCI/NH$_3$) m/z 257 [M+H]$^+$.

Example 33

8-(cyclohexylmethoxy)quinolin-2-amine

The title compound was prepared according to the procedure described in Example 1 substituting cyclohexylmethanol for isopropylalcohol. $^1$H NMR (500 MHz, CDCl$_3$) δ ppm 7.99 (d, 1H), 7.31 (t, 1H), 7.22 (m, 1H), 7.11 (d, 1H), 7.04 (d, 1H), 3.96 (d, 2H), 2.14 (m, 1H), 2.00 (m, 2H), 1.73 (m, 3H), 1.37 (m, 2H), 1.22 (m, 1H), 1.05 (m, 2H); MS (DCI/NH$_3$) m/z 257 [M+H]$^+$.

Example 34

8-(3-methoxy-3-methylbutoxy)quinolin-2-amine

The title compound was prepared according to the procedure described in Example 1 substituting 3-methoxy-3-methyl-1-butanol for isopropylalcohol. $^1$H NMR (500 MHz, CDCl$_3$) δ ppm 7.98 (d, 1H), 7.31 (t, 1H), 7.22 (m, 1H), 7.16 (m, 1H), 7.05 (d, 1H), 4.28 (t, 2H), 3.23 (s, 3H), 2.30 (t, 2H), 1.27 (s, 6H); MS (DCI/NH$_3$) m/z 261 [M+H]$^+$.

Example 35

8-(2-cyclohexylethoxy)quinolin-2-amine

The title compound was prepared according to the procedure described in Example 1 substituting 2-cyclohexylethanol for isopropylalcohol. $^1$H NMR (500 MHz, CDCl$_3$) δ ppm 7.96 (d, 1H), 7.29 (t, 1H), 7.20 (d, 1H), 7.09 (m, 2H), 4.21 (t, 2H), 1.94 (m, 2H), 1.78 (m, 2H), 1.71 (m, 2H), 1.65 (m, 1H), 1.51 (m, 1H), 1.12–1.34 (m, 3H), 1.02 (m, 2H); MS (DCI/NH$_3$) m/z 271 [M+H]$^+$.

Example 36

8-((1S,4R)-bicyclo[2.2.1]hept-2-ylmethoxy)quinolin-2-amine

The title compound was prepared according to the procedure described in Example 1 substituting 2-norbomanemethanol for isopropylalcohol. $^1$H NMR (500 MHz, CDCl$_3$) δ ppm 7.94 (m, 1H), 7.28 (m, 1H), 7.19 (m, 1H), 7.10 (m, 2H), 4.10 (m, 1.3H), 3.98 (t, 0.35H), 3.83 (m, 0.35H), 2.64 (m, 0.7H), 2.57 (m, 0.7H), 2.31 (m, 0.35H), 2.24 (m, 1.3H), 1.92 (m, 0.70H), 1.28–1.64 (m, 4.9H), 1.17 (m, 1.65H), 0.76 (m, 0.7H); MS (DCI/NH$_3$) m/z 269 [M+H]$^+$.

Example 37

8-((1-ethylpentyl)oxy)quinolin-2-amine

A reaction vessel of the PE Biosystems Solaris 530™ Organic Synthesizer was charged with 230 mg PS-PPh$_3$ resin (Aldrich Chemical Co., Inc, 5.50 equiv), and purged by passing a stream of N$_2$ for 45 seconds. A solution of 2-amino-8-hydroxyquinoline (1.200 mL; 16.6 mg/mL; 0.125 mmol) in anhydr. THF was added to the vessel and the resultant suspension was shaken for 15 min. Then, a solution of DBAD (0.50 mL; 46 mg/mL; 1.6 equiv) in anhydr. THF was added and the contents of the flask were shaken for 10 min. A solution of heptan-3-ol (0.400 mL, 0.400 mM; 1.25 equiv) in anhydr. THF was then added and the resulting suspension was shaken at room temperature for 2 h. Then a solution of DBAD (0.38 mL; 46 mg/mL; 1.6 equiv) in anhydr. THF was added. After 10 minutes of shaking a solution of heptan-3-ol (0.400 mL, 0.400 mM; 1.25 equiv) in anhydr. THF was added and the reaction mixture was shaken for 2 h. The last addition of DBAD was then repeated and the reaction mixture was shaken for an additional 4 h. The resultant suspension was filtered, and the resin washed with THF (2.5, 3.5 and 3.0 mL). The filtrate and washings were combined and evaporated in vacuo. The resulting crude product was then treated with 6.0 mL of 4 M HCl in dioxane at room temperature for 4 h. The resulting solution was evaporated in vacuo. The residue was dissolved in 1.5 mL of a 1:1 mixture of DMSO/MeOH and purified by preparative reverse-phase HPLC. $^1$H NMR (500 MHz, CDCl$_3$) δ ppm 7.97 (d, 1H), 7.30 (t, 1H), 7.19 (m, 1H), 7.11 (m, 1H), 7.06 (d, 1H), 4.38 (m, 1H), 1.92 (m, 2H), 1.76 (m, 2H), 1.45 (m, 1H), 1.34 (m, 3H), 0.98 (t, 3H), 0.88 (t, 3H); MS (DCI/NH$_3$) m/z 259 [M+H]$^+$.

Example 38

8-(((1R)-1-methylpropyl)oxy)quinolin-2-amine

The title compound was prepared according to the procedure described in Example 37 substituting (2S)-butan-2-ol for heptan-3-ol. $^1$H NMR (500 MHz, CDCl$_3$) δ ppm 7.94 (d, 1H), 7.29 (t, 1H), 7.19 (m, 1H), 7.10 (d, 1H), 7.07 (d, 1H), 4.38–4.58 (m, 1H), 2.00 (m, 1H), 1.73 (m, 1H), 1.43 (d, 3H), 1.01 (t, 3H); MS (DCI/NH$_3$) m/z 217 [M+H]$^+$.

Example 39

8-(1-cyclohexylpropoxy)quinolin-2-amine

The title compound was prepared according to the procedure described in Example 37 substituting 1-cyclohexylpropan-1-ol for heptan-3-ol. $^1$H NMR (500 MHz, CDCl$_3$) δ ppm 7.94 (d, 1H), 7.27 (t, 1H), 7.16 (m, 1H), 7.09 (m, 2H), 4.23 (m, 1H), 1.91 (m, 3H), 1.58–1.84 (m, 5H), 1.03–1.34 (m, 5H), 0.94 (t, 3H); MS (DCI/NH$_3$) m/z 285 [M+H]$^+$.

Example 40

8-(1-ethyl-2-methylpropoxy)quinolin-2-amine

The title compound was prepared according to the procedure described in Example 37 substituting 2-methylpentan-3-ol for heptan-3-ol. $^1$H NMR (500 MHz, CDCl$_3$) δ ppm 7.93 (d, 1H), 7.29 (m, 1H), 7.16 (m, 1H), 7.10 (m, 2H), 4.23 (m, 1H), 2.21 (m, 1H), 1.96 (m, 1H), 1.63–1.84 (m, 1H), 0.80–1.12 (m, 9H); MS (DCI/NH$_3$) m/z 245 [M+H]$^+$.

Example 41

8-(((1R,2S)-2-methylcyclohexyl)oxy)quinolin-2-amine

The title compound was prepared according to the procedure described in Example 37 substituting trans-2-methylcyclohexanol for heptan-3-ol. $^1$H NMR (500 MHz, CDCl$_3$) δ ppm 7.93 (d, 1H), 7.28 (t, 1H), 7.13 (m, 3H), 4.59 (m, 1H), 2.15 (m, 1H), 1.99 (m, 2H), 1.68 (m, 3H), 1.53 (m, 1H), 1.38 (m, 2H), 1.04 (d, 3H); MS (DCI/NH$_3$) m/z 257 [M+H]$^+$.

Example 42

8-(((1S)-1,2-dimethylpropyl)oxy)quinolin-2-amine

The title compound was prepared according to the procedure described in Example 37 substituting (2R)-3-meth ylbutan-2-ol for heptan-3-ol. $^1$H NMR (500 MHz, CDCl$_3$) δ ppm 7.94 (d, 1H), 7.29 (t, 1H), 7.18 (m, 1H), 7.09 (m, 2H), 4.34 (m, 1H), 2.22 (m, 1H), 1.38 (d, 3H), 1.05 (d, 3H), 1.01 (d, 3H); MS (DCI/NH$_3$) m/z 231 [M+H]$^+$.

Example 43

8-(1-(methoxymethyl)propoxy)quinolin-2-amine

The title compound was prepared according to the procedure described in Example 37 substituting 1-methoxybutan-2-ol for heptan-3-ol. $^1$H NMR (500 MHz, CDCl$_3$) δ ppm 7.94 (d, 1H), 7.29 (t, 1H), 7.21 (m, 2H), 7.05 (d, 1H), 4.56 (m, 1H), 3.88 (dd, 1H), 3.64 (dd, 1H), 3.37 (s, 3H), 1.74–1.95 (m, 2H), 1.01 (t, 3H); MS (DCI/NH$_3$) m/z 247 [M+H]$^+$.

Example 44

8-(3-ethoxy-1-ethylpropoxy)quinolin-2-amine

The title compound was prepared according to the procedure described in Example 37 substituting 1-ethoxypentan-3-ol for heptan-3-ol. $^1$H NMR (500 MHz, CDCl$_3$) δ ppm 7.97 (d, 1H), 7.30 (t, 1H), 7.24 (m, 1H), 7.19 (m, 1H), 7.05 (d, 1H), 4.68 (m, 1H), 3.55 (m, 2H), 3.46 (m, 1H), 3.33 (m, 1H), 2.20 (m, 1H), 1.95 (m, 2H), 1.78 (m, 1H), 1.13 (t, 3H), 0.97 (t, 3H); MS (DCI/NH$_3$) m/z 275 [M+H]$^+$.

Example 45

8-(((1R)-1,2-dimethylpropyl)oxy)quinolin-2-amine

The title compound was prepared according to the procedure described in Example 37 substituting (2S)-3-methylbutan-2-ol for heptan-3-ol. $^1$H NMR (500 MHz, CDCl$_3$) δ ppm 7.94 (d, 1H), 7.29 (t, 1H), 7.18 (m, 1H), 7.07 (m, 2H), 4.32 (m, 1H), 2.21 (m, 1H), 1.38 (d, 3H), 1.05 (d, 3H), 1.01 (d, 3H); MS (DCI/NH$_3$) m/z 231 [M+H]$^+$.

Example 46

8-(((1S)-2-methyl-1-phenylpropyl)oxy)quinolin-2-amine

The title compound was prepared according to the procedure described in Example 37 substituting (1R)-2-methyl-1-phenylpropan-1-ol for heptan-3-ol. $^1$H NMR (500 MHz, CDCl$_3$) δ ppm 7.79 (d, 1H), 7.45 (m, 2H), 7.30 (m, 2H), 7.22 (m, 1H), 7.09 (dd, 1H), 6.96 (t, 1H), 6.80 (dd, 1H), 6.72 (d, 1H), 4.93 (d, 1H), 2.40 (m, 1H), 1.22 (d, 3H), 0.92 (d, 3H); MS (DCI/NH$_3$) m/z 293 [M+H]$^+$.

Example 47

8-(((1R,2S)-2-methylcyclopentyl)oxy)quinolin-2-amine

The title compound was prepared according to the procedure described in Example 37 substituting trans-2-methylcyclopentanol for heptan-3-ol. $^1$H NMR (500 MHz, CDCl$_3$) δ ppm 7.94 (d, 1H), 7.28 (t, 1H), 7.18 (m, 1H), 7.13 (m, 1H), 7.07 (d, 1H), 4.81 (m, 1H), 2.21 (m, 1H), 2.07 (m, 2H), 1.87 (m, 3H), 1.61 (m, 1H), 1.12 (d, 3H); MS (DCI/NH$_3$) m/z 243 [M+H]$^+$.

Example 48

8-(1,2-diethylbutoxy)quinolin-2-amine

The title compound was prepared according to the procedure described in Example 37 substituting 4-ethylhexan-3-ol for heptan-3-ol. $^1$H NMR (500 MHz, CDCl$_3$) δ ppm 7.94 (d, 1H), 7.28 (t, 1H), 7.18 (m, 1H), 7.08 (m, 2H), 4.47 (m, 1H), 2.01 (m, 1H), 1.61–1.82 (m, 3H), 1.50 (m, 2H), 1.29 (m, 1H), 0.98 (m, 6H), 0.86 (m, 3H); MS (DCI/NH$_3$) m/z 273 [M+H]$^+$.

Example 49

8-((1,4-diethylhexyl)oxy)quinolin-2-amine

The title compound was prepared according to the procedure described in Example 37 substituting 6-ethyloctan-3-ol for heptan-3-ol. $^1$H NMR (500 MHz, CDCl$_3$) δ ppm 7.96 (d, 1H), 7.30 (t, 1H), 7.19 (m, 1H), 7.08 (m, 2H), 4.38 (m, 1H), 1.78–1.99 (m, 3H), 1.72 (m, 1H), 1.40 (m, 1H), 1.28 (m, 5H), 1.18 (m, 1H), 0.99 (t, 1H), 0.79 (m, 6H); MS (DCI/NH$_3$) m/z 301 [M+H]$^+$.

Example 50

8-(1,3-dimethylbutoxy)quinolin-2-amine

The title compound was prepared according to the procedure described in Example 37 substituting 4-methylpentan-2-ol for heptan-3-ol. $^1$H NMR (500 MHz, CDCl$_3$) δ ppm 7.96 (d, 1H), 7.3 (t, 1H), 7.20 (m, 1H), 7.13 (m, 1H), 7.06 (d, 1H), 4.67 (m, 1H), 2.01 (m, 1H), 1.83 (m, 1H), 1.53 (m, 1H), 1.41 (d, 3H), 0.96 (d, 3H), 0.92 (d, 3H); MS (DCI/NH$_3$) m/z 245 [M+H]$^+$.

Example 51

8-(((1R,2R)-2-methylcyclohexyl)oxy)quinolin-2-amine

The title compound was prepared according to the procedure described in Example 37 substituting cis-2-methylcyclohexanol for heptan-3-ol. $^1$H NMR (500 MHz, CDCl$_3$) δ ppm 7.94 (d, 1H), 7.28 (t, 1H), 7.18 (m, 1H), 7.14 (d, 1H) 7.07 (d, 1H), 3.99 (m, 1H), 2.11 (m, 2H), 1.86 (m, 2H), 1.69 (m, 1H), 1.56 (m, 1H), 1.36 (m, 2H), 1.13 (m, 1H), 1.03 (m, 3H); MS (DCI/NH$_3$) m/z 257 [M+H]$^+$.

Example 52

8-((1-isopropylbut-3-enyl)oxy)quinolin-2-amine

The title compound was prepared according to the procedure described in Example 37 substituting 2-methylhex-5-en-3-ol for heptan-3-ol. $^1$H NMR (500 MHz, CDCl$_3$) δ ppm 7.89 (d, 1H), 7.20 (m, 2H), 7.08 (d, 1H), 6.96 (m, 1H), 5.90 (m, 1H), 5.12 (dd, 1H), 4.99 (d, 1H), 4.31 (m, 1H), 2.69 (m, 1H), 2.51 (m, 1H), 2.18 (m, 1H), 1.06 (d, 3H), 1.02 (d, 3H); MS (DCI/NH$_3$) m/z 257 [M+H]$^+$.

Example 53

8-((1-isopropylpentyl)oxy)quinolin-2-amine

The title compound was prepared according to the procedure described in Example 37 substituting 2-methylheptan-3-ol for heptan-3-ol. $^1$H NMR (500 MHz, CDCl$_3$) δ ppm 7.94 (d, 1H), 7.29 (m, 1H), 7.17 (m, 1H), 7.08 (m, 2H), 4.28 (m, 1H), 2.19 (m, 1H), 1.98 (m, 1H), 1.68 (m, 1H), 1.46 (m, 1H), 1.31 (m, 3H), 1.01 (m, 6H), 0.86 (m, 3H); MS (DCI/NH$_3$) m/z 273 [M+H]$^+$.

Example 54

8-(1-benzylpropoxy)quinolin-2-amine

The title compound was prepared according to the procedure described in Example 37 substituting 1-phenylbutan-2-ol for heptan-3-ol. $^1$H NMR (500 MHz, CDCl$_3$) δ ppm 7.86 (d, 1H), 7.30 (m, 2H), 7.23 (m, 2H), 7.16 (m, 3H), 6.99 (m, 1H), 6.88 (d, 1H), 4.59 (m, 1H), 3.27 (dd, 1H), 2.99 (dd, 1H), 1.73–1.97 (m, 2H), 1.02 (t, 3H); MS (DCI/NH$_3$) m/z 293 [M+H]$^+$.

Example 55

8-(1-(4-fluorophenyl)ethoxy)quinolin-2-amine

The title compound was prepared according to the procedure described in Example 37 substituting 1-(4-fluorophenyl)ethanol for heptan-3-ol. $^1$H NMR (500 MHz, CDCl$_3$) δ ppm 7.92 (d, 1H), 7.48 (m, 2H), 7.14 (m, 2H), 7.01 (m, 3H), 6.94 (m, 1H), 5.50 (q, 1H), 1.84 (d, 3H); MS (DCI/NH$_3$) m/z 283 [M+H]$^+$.

Example 56

8-(1-cyclohexylethoxy)quinolin-2-amine

The title compound was prepared according to the procedure described in Example 37 substituting 1-cyclohexylethanol for heptan-3-ol. $^1$H NMR (500 MHz, CDCl$_3$) δ ppm 7.95 (d, 1H), 7.28 (t, 1H), 7.18 (m, 1H), 7.11 (d, 1H), 7.05 (d, 1H), 4.34 (m, 1H), 2.02 (m, 1H), 1.92 (m, 1H), 1.83 (m, 1H), 1.71 (m, 3H), 1.39 (d, 3H), 1.28 (m, 2H), 1.16 (m, 1H), 1.03 (m, 2H); MS (DCI/NH$_3$) m/z 271 [M+H]$^+$.

Example 57

8-(1-methyl-2-phenylethoxy)quinolin-2-amine

The title compound was prepared according to the procedure described in Example 37 substituting 1-phenyl-2-propanol for heptan-3-ol. $^1$H NMR (500 MHz, CDCl$_3$) δ ppm 7.93 (d, 1H), 7.28 (m, 5H), 7.17 (m, 2H), 7.07 (m, 2H), 4.80 (m, 1H), 3.39 (dd, 1H), 2.99 (dd, 1H), 1.45 (d, 3H); MS (DCI/NH$_3$) m/z 279 [M+H]$^+$.

Example 58

8-(((1S)-1-methylpropyl)oxy)quinolin-2-amine

The title compound was prepared according to the procedure described in Example 37 substituting (R)-(−)-2-butanol for heptan-3-ol. $^1$H NMR (500 MHz, CDCl$_3$) δ ppm 7.95 (d, 1H), 7.30 (t, 1H), 7.19 (m, 1H), 7.11 (m, 1H), 7.06 (d, 1H), 4.51 (m, 1H), 2.01 (m, 1H), 1.76 (m, 1H), 1.43 (d, 3H), 1.01 (t, 3H); MS (DCI/NH$_3$) m/z 217 [M+H]$^+$.

Example 59

8-(2,3-dihydro-1H-inden-2-yloxy)quinolin-2-amine

The title compound was prepared according to the procedure described in Example 37 substituting 2-indanol for heptan-3-ol. $^1$H NMR (500 MHz, DMSO-d$_6$) δ ppm 8.37 (d, 1H), 7.49 (m, 3H), 7.31 (m, 2H), 7.21 (m, 2H), 7.11 (d, 1H), 5.51 (m, 1H), 3.59 (d, 1H), 3.55 (d, 1H), 3.28 (d, 1H), 3.24 (d, 1H); MS (DCI/NH$_3$) m/z 277 [M+H]$^+$.

Example 60

8-(3-methoxybutoxy)quinolin-2-amine

The title compound was prepared according to the procedure described in Example 37 substituting 3-methoxy-1-butanol for heptan-3-ol. $^1$H NMR (500 MHz, CDCl$_3$) δ ppm 7.98 (d, 1H), 7.32 (t, 1H), 7.22 (m, 1H), 7.15 (m, 1H), 7.05 (d, 1H), 4.34 (m, 1H), 4.25 (m, 1H), 3.70 (m, 1H), 3.32 (s, 3H), 2.30 (m, 1H), 2.06 (m, 1H), 1.24 (d, 3H); MS (DCI/NH$_3$) m/z 247 [M+H]$^+$.

Example 61

8-(2-(1-naphthyl)ethoxy)quinolin-2-amine

The title compound was prepared according to the procedure described in Example 37 substituting 1-naphthaleneethanol for heptan-3-ol. $^1$H NMR (500 MHz, CDCl$_3$) δ ppm 8.16 (m, 1H), 7.98 (d, 1H), 7.86 (m, 1H), 7.74 (m, 1H), 7.50 (m, 3H), 7.41 (m, 1H), 7.23 (m, 2H), 7.07 (d, 1H), 7.02 (dd, 1H), 4.48 (d, 2H), 3.86 (d, 2H); MS (DCI/NH$_3$) m/z 315 [M+H]$^+$.

Example 62

8-((1-ethyl-4-methylpentyl)oxy)quinolin-2-amine

A 7.5 mL conical microwave vessel (Personal Chemistry) equipped with a septum cap and a magnetic stirring bar was charged with PS-PPh$_3$ resin (Aldrich Chemical Co., Inc, 140 mg, 4.40 equiv), 2-amino-8-hydroxyquinoline (15.0 mg, 0.0960 mmol) and DBAD (69 mg, 3.2 equiv) and purged by passing a stream of N$_2$ for 45 seconds. Anhydr. THF (1.5 mL) was added and contents of the vessel were stirred for 10 min. Then, neat 6-methyl-3-heptanol (4 equiv) was added to the vessel and the resulting suspension was irradiated in Personal Chemistry Smith Synthesizer (150° C. for 330 s; 300 W). The suspension was then filtered, and the resin washed with THF (3×3.0 mL). The filtrate and washings were combined and evaporated in vacuo. The residue was then treated with 6.0 mL of 4 M HCl in dioxane at room temperature for 4 h. The resulting solution was evaporated in vacuo. The residue was dissolved in 1.5 mL of a 1:1 mixture of DMSO/MeOH and purified by preparative reverse-phase HPLC. $^1$H NMR (500 MHz, CDCl$_3$) δ ppm 7.96 (d, 1H), 7.29 (t, 1H), 7.19 (m, 1H), 7.10 (d, 1H), 7.05 (br d, 1H), 4.37 (m, 1H), 1.91 (m, 2H), 1.78 (m, 2H), 1.55 (m, 1H), 1.35 (m, 1H), 1.24 (m, 1H), 0.98 (t, 3H), 0.87 (m, 6H); MS (DCI/NH$_3$) m/z 273 [M+H]$^+$.

Example 63

8-(((1S,5S)-3,3,5-trimethylcyclohexyl)oxy)quinolin-2-amine

The title compound was prepared according to the procedure described in Example 62 substituting trans-3,3,5-trimethylcyclohexanol for 6-methyl-3-heptanol. $^1$H NMR (500 MHz, CDCl$_3$) δ ppm 7.93 (br d, 1H), 7.28 (d, 1H), 7.17

(d, 1H), 7.13 (d, 1H), 7.05 (br d, 1H), 4.61 (m, 1H), 2.15 (m, 1H), 1.88 (m, 1H), 1.73 (m, 1H), 1.56 (m, 1H), 1.39 (m, 1H), 1.31 (m, 1H), 1.02 (m, 6H), 0.96 (d, 3H), 0.91 (m, 1H); MS (DCI/NH$_3$) m/z 285 [M+H]$^+$.

Example 64

8-(((1R,5S)-3,3,5-trimethylcyclohexyl)oxy)quinolin-2-amine

The title compound was prepared according to the procedure described in Example 62 substituting cis-3,3,5-trimethylcyclohexanol for 6-methyl-3-heptanol. $^1$H NMR (500 MHz, CDCl$_3$) δ ppm 7.95 (d, 1H), 7.30 (t, 1H), 7.18 (m, 1H), 7.11 (d, 1H), 7.04 (br d, 1H), 4.84 (m, 1H), 2.52 (m, 1H), 2.22 (m, 1H), 1.99 (m, 1H), 1.52 (m, 1H), 1.33 (dd, 1H), 1.27 (m, 1H), 0.98 (d, 3H), 0.94 (s, 3H), 0.90 (m, 1H), 0.88 (s, 3H); MS (DCI/NH$_3$) m/z 285 [M+H]$^+$.

Example 65

8-(benzyloxy)quinolin-2-amine

A 20 mL scintillation vial with a septum cap was charged with PS-PPh$_3$ resin (Aldrich Chemical Co., Inc, 100 mg, 2.2 equiv), 2-amino-8-hydroxyquinoline (22 mg, 0.14 mmol) and DBAD (51 mg, 1.6 equiv) and purged by passing a stream of N2 for 45 seconds. Anhydr. THF (3 mL) was added and the contents of the vial were shaken for 5 min. Then, a solution of benzyl alcohol (1.25 equiv) in anhydr. THF (1 mL) was added and the resulting suspension was shaken at room temperature for 8 h. The suspension was filtered, and the resin washed with THF (2.5, 3.5 and 3.0 mL). The filtrate and washings were combined and evaporated in vacuo. The resulting crude product was then dissolved in a mixture of DCM (1 mL), thf (1 mL) and MeOH (3 mL) and the solution was added to MP-TsOH resin (Argonaut Technologies, Inc., 0.5 g). The resulting suspension was agitated at room temperature for 1.5 h. The supernatant was subsequently drained and the resin was washed with DCM (2 mL), MeOH (2 mL), THF (2 mL) and DCM (2 mL). The washed resin was treated with 2 N NH$_3$ in MeOH (4 mL) at room temperature for 1 h. The supernatant was collected and the resin was washed with MeOH (3 mL) and DCM (3 mL). The washes were combined with the collected supernatant. The NH$_3$/MeOH treatment and washes were then repeated. The filtrate and the washes were combined with previously collected and evaporated in vacuo. The residue was dissolved in 1.5 mL of a 1:1 mixture of DMSO/MeOH and purified by preparative reverse-phase HPLC. $^1$H NMR (500 MHz, CDCl$_3$) δ ppm 7.83 (d, 1H), 7.50 (m, 2H), 7.37 (m, 2H), 7.30 (m, 1H), 7.20 (dd, 1H), 7.08 (t, 1H), 6.95 (dd, 1H), 6.68 (d, 1H), 5.38 (s, 2H); MS (DCI/NH$_3$) m/z 251 [M+H]$^+$.

Example 66

8-((3-(trifluoromethyl)benzyl)oxy)quinolin-2-amine

The title compound was prepared according to the procedure described in Example 65 substituting 3-(trifluoromethyl)benzyl alcohol for benzyl alcohol. $^1$H NMR (500 MHz, CDCl$_3$) δ ppm 7.88 (d, 1H), 7.78 (s, 1H), 7.72 (d, 1H), 7.56 (d, 1H), 7.48 (t, 1H), 7.26 (m, 1H), 7.12 (t, 1H), 6.96 (m, 1H), 6.78 (d, 1H), 5.42 (s, 2H); MS (DCI/NH$_3$) m/z 319 [M+H]$^+$.

Example 67

8-((2,4-dimethylbenzyl)oxy)quinolin-2-amine

The title compound was prepared according to the procedure described in Example 65 substituting 2,4-dimethylbenzyl alcohol for benzyl alcohol. $^1$H NMR (500 MHz, CDCl$_3$) δ ppm 7.80 (d, 1H), 7.33 (d, 1H), 7.19 (dd, 1H), 7.11 (t, 1H), 7.02 (br s, 1H), 6.98 (m, 2H), 6.57 (d, 1H), 5.24 (s, 2H), 2.37 (s, 3H), 2.32 (s, 3H); MS (DCI/NH$_3$) m/z 279 [M+H]$^+$.

Example 68

8-(((3S)-1-benzylpyrrolidin-3-yl)oxy)quinolin-2-amine

The title compound was prepared according to the procedure described in Example 62 substituting (R)-1-benzyl-3-pyrrolidinol for benzyl alcohol. $^1$H NMR (500 MHz, CDCl$_3$) δ ppm 7.83 (d, 1H), 7.37 (m, 2H), 7.32 (m, 2H), 7.28 (m, 1H), 7.20 (dd, 1H), 7.14 (t, 1H), 6.90 (dd, 1H), 6.72 (d, 1H), 5.08 (m, 1H), 3.87 (d, 1H), 3.80 (d, 1H), 3.28 (dd, 1H), 3.07 (dd, 1H), 2.95 (m, 1H), 2.83 (m, 1H), 2.38 (m, 1H), 2.24 (m, 1H); MS (DCI/NH$_3$) m/z 320 [M+H]$^+$.

Example 69

8-(((3R)-1-benzylpyrrolidin-3-yl)oxy)quinolin-2-amine

The title compound was prepared according to the procedure described in Example 65 substituting (S)-1-benzyl-3-pyrrolidinol for benzyl alcohol. $^1$H NMR (500 MHz, CDCl$_3$) δ ppm 7.83 (d, 1H), 7.37 (m, 2H), 7.32 (m, 2H), 7.28 (m, 1H), 7.20 (dd, 1H), 7.14 (t, 1H), 6.90 (dd, 1H), 6.72 (d, 1H), 5.08 (m, 1H), 3.87 (d, 1H), 3.80 (d, 1H), 3.28 (dd, 1H), 3.07 (dd, 1H), 2.95 (m, 1H), 2.83 (m, 1H), 2.38 (m, 1H), 2.24 (m, 1H); MS (DCI/NH$_3$) m/z 320 [M+H]$^+$.

Example 70

8-((1-benzylpiperidin-4-yl)oxy)quinolin-2-amine

The title compound was prepared according to the procedure described in Example 65 substituting 1-benzyl-4-hydroxypiperidine for benzyl alcohol. $^1$H NMR (500 MHz, CDCl$_3$) δ ppm 7.84 (d, 1H), 7.33 (m, 5H), 7.22 (dd, 1H), 7.15 (t, 1H), 7.04 (dd, 1H), 6.72 (d, 1H), 4.54 (m, 1H), 3.69 (s, 2H), 3.00 (m, 2H), 2.47 (m, 2H), 2.16 (m, 2H), 2.06 (m, 2H); MS (DCI/NH$_3$) m/z 334 [M+H]$^+$.

Example 71

8-((1,5-dimethylhex-4-enyl)oxy)quinolin-2-amine

The title compound was prepared according to the procedure described in Example 65 substituting 6-methyl-5-hepten-2-ol for benzyl alcohol. $^1$H NMR (500 MHz, CDCl$_3$) δ ppm 7.85 (m, 1H), 7.18 (m, 2H), 7.01 (dd, 1H), 6.74 (m, 1H), 5.16 (m, 1H), 4.55 (m, 1H), 2.19 (m, 2H), 2.04 (m, 1H), 1.72 (m, 1H), 1.66 (s, 3H), 1.55 (s, 3H), 1.44 (d, 3H); MS (DCI/NH$_3$) m/z 271 [M+H]$^+$.

Example 72

8-(((1R)-1-phenylethyl)oxy)quinolin-2-amine

The title compound was prepared according to the procedure described in Example 65 substituting (S)-(−)-1-phenylethanol for benzyl alcohol. $^1$H NMR (500 MHz, CDCl$_3$) δ ppm 7.83 (d, 1H), 7.47 (m, 2H), 7.32 (m, 2H), 7.23 (m, 1H), 7.13 (dd, 1H), 7.01 (t, 1H), 6.84 (dd, 1H), 6.76 (m, 1H), 5.51 (m, 1H), 1.82 (d, 3H); MS (DCI/NH$_3$) m/z 265 [M+H]$^+$.

Example 73

8-(1-(4-(trifluoromethyl)phenyl)ethoxy)quinolin-2-amine

The title compound was prepared according to the procedure described in Example 65 substituting α-methyl-4-trifluoromethylbenzyl alcohol for benzyl alcohol. $^1$H NMR (500 MHz, CDCl$_3$) δ ppm 7.85 (d, 1H), 7.60 (m, 4H), 7.20 (m, 1H), 7.02 (t, 1H), 6.82 (m, 1H), 6.75 (d, 1H), 5.61 (q, 1H), 1.81 (d, 3H); MS (DCI/NH$_3$) m/z 333 [M+H]$^+$.

Example 74

8-(2-(1-methylpyrrolidin-2-yl)ethoxy)quinolin-2-amine

The title compound was prepared according to the procedure described in Example 65 substituting 1-methyl-2-pyrrolidineethanol for benzyl alcohol. $^1$H NMR (500 MHz, CDCl$_3$) δ ppm 7.85 (d, 1H), 7.23 (dd, 1H), 7.17 (t, 1H), 7.03 (m, 1H), 6.75 (d, 1H), 4.35 (m, 1H), 4.21 (m, 1H), 3.50 (m, 1H), 3.02 (m, 1H), 2.59 (s, 3H), 2.53 (m, 2H), 2.17 (m, 2H), 1.98 (m, 1H), 1.84 (m, 2H); MS (DCI/NH$_3$) m/z 272 [M+H]$^+$.

Example 75

8-(2-(2-((2-aminoquinolin-8-yl)oxy)ethoxy)ethoxy)-quinolin-2-amine

A 20 mL scintillation vial equipped with a septum cap was charged with PS-PPh$_3$ resin (Aldrich Chemical Co., Inc, 132 mg, 4.2 equiv) 2-amino-8-hydroxyquinoline (151 mg, 10 equiv) and DBAD (70 mg, 3.2 equiv) and purged by passing a stream of N$_2$ for 45 seconds. Anhydr. THF (2.0 mL) was added and contents of the vial were agitated for 5 min. Then, a solution of diethylene glycol (10 mg, 0.094 mmol) in anhydr. THF (1 mL) was added to the vial and the resulting suspension was agitated at room temperature for 8 h. The suspension was then filtered, and the resin washed with DMA (6×3.0 mL). The filtrate and washings were combined and evaporated in vacuo. The resulting solid was washed with EtOAc (2.5 mL) DMF (3.0 mL) and hexanes (50 mL in a few portions) and dried under high vacuum at room temperature for 12 h to afford the product. $^1$H NMR (500 MHz, CDCl$_3$) δ ppm 8.06 (d, 2H), 7.34 (t, 2H), 7.29 (m, 2H), 7.13 (m, 2H), 7.06 (d, 2H), 4.36 (m, 4H), 4.08 (m, 4H); MS (DCI/NH$_3$) m/z 391 [M+H]$^+$.

Example 76

8-((4-(((2-aminoquinolin-8-yl)oxy)methyl)benzyl)oxy)-quinolin-2-amine

A 20 mL scintillation vial equipped with a septum cap was charged with PS-PPh$_3$ resin (Aldrich Chemical Co., Inc, 132 mg, 4.2 equiv) 2-amino-8-hydroxyquinoline (151 mg, 10equiv) and DBAD (70 mg, 3.2 equiv) and purged by passing a stream of N$_2$ for 45 seconds. Anhydr. THF (2.0 mL) was added and contents of the vial were agitated for 5 min. Then, a solution of 1,4-benzenedimethanol (10 mg, 0.072 mmol) in anhydr. THF (1 mL) was added to the vial and the resulting suspension was agitated at room temperature for 8 h. The suspension was then filtered, and the resin washed with DMA (6×3.0 mL). The filtrate and washings were combined and evaporated in vacuo. The resulting solid was washed with EtOAc (2.5 mL) and hexanes (50 mL in a few portions) and dried under high vacuum at room temperature for 12 h to afford the product. $^1$H NMR (500 MHz, CDCl$_3$) δ ppm 8.14 (d, 2H), 7.52 (br s, 4H), 7.46 (t, 2H), 7.33 (m, 2H), 7.08 (m, 2H), 7.07 (d, 2H), 5.18 (s, 4H); MS (DCI/NH$_3$) m/z 423 [M+H]$^+$.

Example 77

3-((2-aminoquinolin-8-yl)oxy)propan-1-ol

A 100 mL round bottom flask equipped with a stirring bar and a pressure equalized dropping funnel, under N$_2$, was charged with 0.652 g (2 equiv) PPh$_3$, 0.200 g (1.25 mmol) of 2-amino-8-hydroxyquinoline and 10 mL of anhydr. THF. After stirring for 10 min, 1.8 mL of 1,3-propanediol (20 equiv) was added in one portion. The reaction mixture was then cooled to 0° C. and 0.43 g (1.5 equiv) of DBAD in 15 mL THF was added dropwise over 10 minutes. The reaction was allowed to slowly warm to room temperature and stirring was maintained for 8 h. Then, 0.652 g (2 equiv) of PPh$_3$ was added, the reaction mixture was cooled to 0° C. and 0.431 g (1.5 equiv) of DBAD in 15 mL THF was added dropwise over 10 minutes. The reaction mixture was stirred at room temperature for 12 h. The solution was evaporated in vacuo, the residue was dissolved in DMA (25 mL) and MP-TsOH resin (Argonaut Technologies, Inc., 4.5 g) was added. The resulting suspension was agitated at room temperature for 12 h. The supernatant was subsequently drained and the resin was washed with DMA (2×20 mL), MeOH (2×20 mL) and DMA (20 mL). The washed resin was treated with a mixture of 2 N NH$_3$ in MeOH (15 mL) and DMA (5 mL) at room temperature for 1 h. The solution was drained and the basic wash was repeated two more times. Filtered solutions were combined. The resin was washed with MeOH (20 mL), DMA (20 mL), MeOH (20 mL), DMA (20 mL) and MeOH (20 mL). The washes were combined with the previously collected solutions and evaporated in vacuo. The resulting crude material was purified by silica gel column chromatography (20:1 EtOAc/MeOH+2% TEA) to afford the title compound. $^1$H NMR (500 MHz, CDCl$_3$) δ ppm 7.87 (d, 1H), 7.29 (dd, 1H), 7.17 (t, 1H), 7.12 (dd, 1H), 6.72 (d, 1H), 4.34 (t, 2H), 3.99 (t, 2H), 2.12 (m, 2H), MS (DCI/NH$_3$) m/z 219 [M+H]$^+$.

Example 78

8-(3-((2-methylquinolin-8-yl)oxy)propoxy)quinolin-2-amine

A 20 mL scintillation vial with a septum cap was charged with PS-PPh$_3$ resin (Aldrich Chemical Co., Inc, 60 mg, 2.4 equiv), 8-hydroxyquinaldine (1.5 equiv) and DBAD (28 mg, 1.6 equiv) and purged by passing a stream of N$_2$ for 45 seconds. Anhydr. THF (3 mL) was added and the contents of the vial were shaken for 5 min. Then, a solution of 3-((2-aminoquinolin-8-yl)oxy)propan-1-ol (16.7 mg/mL; 1.0 mL, 0.077 mmol) in anhydr. THF (1 mL) was added and the resulting suspension was agitated at room temperature for 8 h. Then, PS-PPh$_3$ resin (Aldrich Chemical Co., Inc, 60 mg, 2.4 equiv) and DBAD (28 mg, 1.6 equiv) were added and the mixture was agitated at room temperature for additional 6 h. The suspension was filtered, and the resin washed with THF (3×3.0 mL). The filtrate and washings were combined and evaporated in vacuo. The residue was then treated with 6.0 mL of 4 M HCl in dioxane at room temperature for 6 h. The resulting solution was evaporated in vacuo. The residue was dissolved in 1.5 mL of a 1:1 mixture of DMSO/MeOH and purified by preparative reverse-phase HPLC. $^1$H NMR (500 MHz, DMSO-d$_6$) δ ppm 8.60 (d, 1H), 7.90 (d, 1H), 7.69 (t, 1H), 7.65 (d, 1H), 7.53 (d, 1H), 7.46 (d, 1H), 7.30 (t, 1H), 7.24 (m, 1H), 7.16 (m, 1H), 6.99 (d, 1H), 4.65 (br t, 2H), 4.48 (br t, 2H), 3.10 (s, 3H), 2.64 (m, 2H); MS (DCI/NH$_3$) m/z 360 [M+H]$^+$.

Example 79

8-(3-(quinolin-8-yloxy)propoxy)quinolin-2-amine

The title compound was prepared according to the procedure described in Example 78 substituting 8-hydroxyquinoline for 8-hydroxyquinaldine. $^1$H NMR (500 MHz, DMSO-d$_6$) δ ppm 8.93 (m, 1H), 8.50 (br d, 1H), 8.37 (d, 1H), 7.67 (dd, 1H), 7.59 (m, 2H), 7.49 (m, 2H), 7.40 (t, 1H), 7.33 (dd, 1H), 7.13 (d, 1H), 4.57 (br t, 2H), 4.50 (br t, 2H), 2.50 (m, 2H); MS (DCI/NH$_3$) m/z 346 [M+H]$^+$.

Example 80

8-(3-((2-aminoquinolin-8-yl)oxy)propoxy)quinolin-2-ol

The title compound was prepared according to the procedure described in Example 78 substituting 2,8-quinolinediol for 8-hydroxyquinaldine. $^1$H NMR (500 MHz, DMSO-d$_6$) δ ppm 8.37 (d, 1H), 7.88 (d, 1H), 7.48 (m, 2H), 7.42 (m, 1H), 7.23 (dd, 1H), 7.10 (m, 3H), 6.52 (d, 1H), 4.59 (t, 2H), 4.35 (t, 2H), 2.45 (m, 2H); MS (DCI/NH$_3$) m/z 362 [M+H]$^+$.

Example 81

6-(3-((2-aminoquinolin-8-yl)oxy)propoxy)quinolin-2-ol

The title compound was prepared according to the procedure described in Example 78 substituting 2,6-quinolinediol for 8-hydroxyquinaldine. $^1$H NMR (500 MHz, DMSO-d$_6$) δ ppm 8.37 (d, 1H), 7.80 (d, 1H), 7.48 (m, 2H), 7.41 (m, 1H), 7.22 (m, 2H), 7.13 (m, 2H), 6.48 (d, 1H), 4.45 (t, 2H), 4.27 (t, 2H), 2.33 (m, 2H); MS (DCI/NH$_3$) m/z 362 [M+H]$^+$.

Example 82

4-(3-((2-aminoquinolin-8-yl)oxy)propoxy)quinolin-2-amine

The title compound was prepared according to the procedure described in Example 78 substituting 2-aminoquinolin-4-ol for 8-hydroxyquinaldine. $^1$H NMR (500 MHz, DMSO-d$_6$) δ ppm 8.36 (d, 1H), 7.96 (m, 1H), 7.76 (m, 1H), 7.61 (d, 1H), 7.50 (m, 2H), 7.42 (m, 2H), 7.12 (m, 1H), 6.44 (m, 1H), 4.55 (m, 4H), 2.54 (m, 2H); MS (DCI/NH$_3$) m/z 361 [M+H]$^+$.

Example 83

8-(3-phenoxypropoxy)quinolin-2-amine

The title compound was prepared according to the procedure described in Example 78 substituting phenol for 8-hydroxyquinaldine. $^1$H NMR (500 MHz, DMSO-d$_6$) δ ppm 8.37 (d, 1H), 7.45 (m, 3H), 7.28 (m, 2H), 7.13 (d, 1H), 6.93 (m, 3H), 4.44 (t, 2H), 4.24 (t, 2H), 2.34 (m, 2H); MS (DCI/NH$_3$) m/z 295 [M+H]$^+$.

Example 84

8-(3-(3,5-dichlorophenoxy)propoxy)quinolin-2-amine

The title compound was prepared according to the procedure described in Example 78 substituting 3,5-dichlorophenol for 8-hydroxyquinaldine. $^1$H NMR (500 MHz, CDCl$_3$) δ ppm 7.99 (d, 1H), 7.32 (t, 1H), 7.24 (m, 1H), 7.14 (m, 1H), 7.05 (d, 1H), 6.86 (m, 1H), 6.82 (m, 2H), 4.35 (m, 4H), 2.49 (m, 2H); MS (DCI/NH$_3$) m/z 363 [M+H]$^+$.

Example 85

4-((2-aminoquinolin-8-yl)oxy)pentan-1-ol

Example 85A 8-(1-methyl-but-3-enyloxy)-quinolin-2-ylamine

To a 100 mL round bottom flask equipped with a stirring bar, under N$_2$, was added 6.25 g (Aldrich Chemical Co., Inc, 2 equiv) of PS-PPh$_3$ resin followed by 35 mL of anhydr. THF. After stirring for 30 min, 1.5 g (9.38 mmol) of 2-amino-8-hydroxyquinoline was added, followed by 1.16 mL (1.7 equiv) of 4-penten-2-ol. The reaction mixture was then cooled to 0° C. and 2.70 g (1.25 equiv) of DBAD was added in two portions. The reaction was allowed to slowly warm to room temperature and stirring was maintained for 12 h. Then, 0.40 mL (0.5 equiv) of 4-penten-2-ol, 1.26 g (4.81 mmol) of PPh$_3$, and 1.5 g (0.7 equiv) of DBAD were added and stirring was maintained for an additional 12 h. The supernatant was then decanted and the resin was washed several times with CHCl$_3$ and MeOH. The supernatant and the washes were combined, filtered through a layer of Celite®, and evaporated in vacuo. The residue was dissolved in a 50% tfa/CH$_2$Cl$_2$ (10 mL) and left overnight at room temperature. The resulting solution was then diluted with CH$_2$Cl$_2$ (30 mL) and slowly quenched with saturated aqueous NaHCO$_3$. The organic layer was separated and evaporated in vacuo. The resulting residue was dissolved in a 3:1 mixture of MeOH/DMSO and purified by preparative HPLC. The homogeneous fractions were combined, evaporated in vacuo, re-dissolved in EtOAc and free-based with saturated aqueous NaHCO$_3$. The organic layer was separated, dried over anhydr. Na$_2$SO$_4$, and evaporated in vacuo to afford 8-(1-methyl-but-3-enyloxy)-quinolin-2-ylamine. $^1$H NMR (300 MHz, DMSO-d$_6$) δ ppm 7.83 (d, 1H), 7.22 (m, 2H), 7.03 (m, 1H), 6.74 (d, 1H), 6.37 (s, 2H), 5.79–6.02 (m, 1H), 5.00–5.21 (m, 2H), 4.68 (m, 1H), 2.35 (m, 2H), 1.28 (d, 3H), MS (DCI/NH$_3$) m/z 229 [M+H]$^+$.

Example 85B

4-((2-aminoquinolin-8-yl)oxy)pentan-1-ol

To a 100 mL round bottom flask containing 1.33 g (5.83 mmol) of 8-(1-methyl-but-3-enyloxy)-quinolin-2-ylamine was added 30 mL of a 1M solution of $BH_3$/THF via syringe. Following the addition, the flask was fitted with a reflux condenser and the solution heated to reflux under $N_2$ for 6 h. The reaction mixture was then allowed to cool to room temperature and the volatiles were removed in vacuo. The residue was dissolved in $Et_2O$. Following the addition of 2.25 g (56.2 mmol) of solid NaOH, the mixture was placed in an ice bath. The flask was then fitted with a dropping funnel and 10 mL of 20% aqueous $H_2O_2$ was added dropwise with stirring. The funnel was then replaced with a reflux condenser and the mixture heated to reflux with stirring overnight. The resulting suspension was allowed to cool to room temperature and was filtered through a fritted funnel. The ethereal layer was separated, washed thoroughly with 1 M $NaHSO_4$, dried over anhydr. $Na_2SO_4$ and evaporated in vacuo. The resulting crude material was purified by silica gel column chromatography (5–25% $MeOH/CH_2Cl_2$) to afford the title compound. $^1H$ NMR (300 MHz, DMSO-$d_6$) δ ppm 7.82 (d, 1H), 7.16 (m, 1H), 7.03 (m, 1H), 6.97 (m, 1H), 6.73 (d, 1H), 6.33 (s, 1H), 4.62 (m, 1H), 4.46 (m, 1H), 3.44 (m, 2H), 1.76 (m, 1H), 1.59 (m, 3H), 1.27 (d, 3H); MS ($DCI/NH_3$) m/z 247 $[M+H]^+$.

Example 86

8-(1-methyl-4-((2-methylquinolin-8-yl)oxy)butoxy)quinolin-2-amine

A 20 mL scintillation vial with a septum cap was charged with $PS-PPh_3$ resin (Aldrich Chemical Co., Inc, 90 mg, 4.4 equiv), 8-hydroxyquinaldine (1.5 equiv) and DBAD (22 mg, 1.6 equiv) and purged by passing a stream of $N_2$ for 45 seconds. Anhydr. THF (3 mL) was added and the contents of the vial were shaken for 5 min. Then, a solution of 4-((2-aminoquinolin-8-yl)oxy)pentan-1-ol (15.0 mg/mL; 1.0 mL, 0.061 mmol)) in anhydr. THF (1 mL) was added and the resulting suspension was agitated at room temperature for 6 h. Following this, DBAD (22 mg, 1.6 equiv) was added and the mixture was agitated at room temperature for additional 12 h. The suspension was filtered, and the resin washed with THF (3×3.0 mL). The filtrate and washings were combined and evaporated in vacuo. The residue was then treated with 6.0 mL of 4 M HCl in dioxane at room temperature for 6 h. The resulting solution was evaporated in vacuo. The residue was dissolved in 1.5 mL of a 1:1 mixture of DMSO/MeOH and purified by preparative reverse-phase HPLC. $^1H$ NMR (500 MHz, $CDCl_3$) δ ppm 8.61 (d, 1H), 7.89 (d, 1H), 7.66 (m, 2H), 7.52 (d, 1H), 7.29 (m, 3H), 7.15 (m, 2H), 4.74 (m, 1H), 4.31 (m, 2H), 3.09 (s, 3H), 2.36 (m, 2H), 2.05 (m, 2H), 1.44 (d, 3H); MS ($DCI/NH_3$) m/z 388 $[M+H]^+$.

Example 87

8-(4-((2-aminoquinolin-8-yl)oxy)-1-methylbutoxy)quinolin-2-amine

The title compound was prepared according to the procedure described in Example 86 substituting 2-aminoquinolin-8-ol for 8-hydroxyquinaldine. $^1H$ NMR (500 MHz, $CDCl_3$) δ ppm 7.99 (m, 2H), 7.33 (m, 3H), 7.22 (m, 2H), 7.14 (m, 2H), 7.08 (m, 1H), 4.69 (m, 1H), 4.23 (m, 2H), 1.88 (m, 4H), 1.46 (d, 3H); MS ($DCI/NH_3$) m/z 389 $[M+H]^+$.

Example 88

8-(4-(3,5-dichlorophenoxy)-1-methylbutoxy)quinolin-2-amine

The title compound was prepared according to the procedure described in Example 86 substituting 3,5-dichlorophenol for 8-hydroxyquinaldine. $^1H$ NMR (500 MHz, $CDCl_3$) δ ppm 7.96 (d, 1H), 7.32 (t, 1H), 7.21 (dd, 1H), 7.12 (m, 1H), 6.99 (d, 1H), 6.84 (m, 1H), 6.64 (m, 2H), 4.68 (m, 1H), 4.05 (m, 1H), 3.95 (m, 1H), 2.18 (m, 1H), 2.00 (m, 3H), 1.47 (d, 3H); MS ($DCI/NH_3$) m/z 391 $[M+H]^+$.

Example 89

8-(4-(2-methoxyphenoxy)-1-methylbutoxy)quinolin-2-amine

The title compound was prepared according to the procedure described in Example 86 substituting 2-methoxyphenol for 8-hydroxyquinaldine. $^1H$ NMR (500 MHz, $CDCl_3$) δ ppm 7.94 (d, 1H), 7.28 (t, 1H), 7.15 (m, 1H), 7.14 (d, 1H), 7.02 (d, 1H), 6.86 (m, 4H), 4.74 (m, 1H), 4.06 (m, 2H), 3.80 (m, 3H), 2.21 (m, 1H), 2.02 (m, 3H), 1.45 (d, 3H); MS ($DCI/NH_3$) m/z 353 $[M+H]^+$.

Example 90

8-(1-methyl-4-(quinolin-7-yloxy)butoxy)quinolin-2-amine

The title compound was prepared according to the procedure described in Example 86 substituting 7-hydroxyquinoline for 8-hydroxyquinaldine. $^1H$ NMR (500 MHz, $CDCl_3$) δ ppm 8.99 (br d, 1H), 8.61 (d, 1H), 7.88 (d, 1H), 7.83 (d, 1H), 7.77 (d, 1H), 7.65 (dd, 1H), 7.30 (m, 2H), 7.19 (m, 1H), 7.14 (d, 1H), 7.01 (d, 1H), 4.73 (m, 1H), 4.22–4.42 (m, 2H), 2.19 (m, 2H), 2.00 (m, 2H), 1.48 (d, 3H); MS ($DCI/NH_3$) m/z 373 $[M+H]^+$.

Example 91

N-(4-((4-((2-aminoquinolin-8-yl)oxy)pentyl)oxy)phenyl)acetamide

The title compound was prepared according to the procedure described in Example 86 substituting acetaminophen for 8-hydroxyquinaldine. $^1H$ NMR (500 MHz, $CDCl_3$) δ ppm 7.90 (d, 1H), 7.29 (t, 1H), 7.20 (m, 3H), 7.11 (m, 1H), 6.95 (d, 1H), 6.61 (m, 2H), 4.70 (m, 1H), 4.05 (m, 1H), 3.91 (m, 1H), 2.14 (s, 3H), 2.08 (m, 1H), 1.95 (m, 3H), 1.48 (d, 3H); MS ($DCI/NH_3$) m/z 380 $[M+H]^+$.

Example 92 methyl 3-((4-((2-aminoquinolin-8-yl)oxy)pentyl)oxy)benzoate

A reaction vessel of the PE Biosystems Solaris 530™ Organic Synthesizer was charged with $PS-PPh_3$ resin (Aldrich Chemical Co., Inc, 120 mg, 4.4 equiv), and purged by passing a stream of $N_2$ for 45 seconds. A solution of methyl 3-hydroxybenzoate (0.41 mL, 0.30 mM) in anhydr. THF (DMA for phenols not soluble in THF) was added to the vessel and the resultant suspension was shaken for 15 min. Then, a solution of DBAD (0.50 mL; 60 mg/mL) in anhydr. THF was added and the contents of the flask were shaken for 10 min. A solution of 4-((2-aminoquinolin-8-yl)oxy)pentan-1-ol (1.50 mL; 13.3 mg/mL) in anhydr. THF was then added and the resulting suspension was shaken at room temperature for 3 h. The addition of DBAD and the phenol was then repeated and the agitation maintained for an additional 3 h. The addition of DBAD was then repeated one more time and the agitation was maintained for an additional 6 h. The resultant suspension was filtered, and the resin washed with THF (2.5, 3.5 and 3.0 mL). The filtrate and washings were combined and evaporated in vacuo. The resulting crude product was then treated with 6.0 mL of 4 M HCl in dioxane at room temperature for 12 h. The resulting solution was evaporated in vacuo. The residue was dissolved in 1.5 mL of a 1:1 mixture of DMSO/MeOH and purified by preparative reverse-phase HPLC. $^1$H NMR (500 MHz, CDCl$_3$) δ ppm 7.94 (d, 1H), 7.56 (m, 1H), 7.46 (m, 1H), 7.29 (m, 2H), 7.19 (m, 1H), 7.13 (d, 1H), 7.00 (m, 2H), 4.71 (m, 1H), 4.11 (m, 1H), 4.04 (m, 1H), 3.89 (s, 3H), 2.21 (m, 1H), 2.01 (m, 3H), 1.47 (d, 3H); MS (DCI/NH$_3$) m/z 381 [M+H]$^+$.

Example 93

8-(1-methyl-4-(3,4,5-trimethylphenoxy)butoxy) quinolin-2-amine

The title compound was prepared according to the procedure described in Example 92 substituting methyl 3,4,5-trimethylphenol for methyl 3-hydroxybenzoate. $^1$H NMR (500 MHz, CDCl$_3$) δ ppm 7.92 (d, 1H), 7.28 (t, 1H), 7.18 (m, 1H), 7.12 (d, 1H), 6.98 (d, 1H), 6.48 (s, 2H), 4.70 (m, 1H), 4.01 (m, 1H), 3.95 (m, 1H), 2.20 (s, 6H), 2.19 (m, 1H), 2.06 (s, 3H), 1.95 (m, 3H), 1.46 (d, 3H); MS (DCI/NH$_3$) m/z 365 [M+H]$^+$.

Example 94 methyl O-(4-((2-aminoquinolin-8-yl)oxy)pentyl)-L-tyrosinate

The title compound was prepared according to the procedure described in Example 92 substituting methyl methyl L-tyrosinate for methyl 3-hydroxybenzoate. $^1$H NMR (500 MHz, DMSO-d$_6$) δ ppm 8.36 (d, 1H), 7.48 (m, 2H), 7.41 (m, 1H), 7.13 (d, 1H), 7.09 (d, 2H), 6.84 (d, 2H), 4.85 (m, 1H), 4.23 (t, 1H), 3.99 (m, 2H), 3.68 (s, 3H), 3.01 (m, 2H), 1.80–2.04 (m, 4H), 1.39 (d, 3H); MS (DCI/NH$_3$) m/z 424 [M+H]$^+$.

Example 95

8-(1-methyl-4-(2-naphthyloxy)butoxy)quinolin-2-amine

The title compound was prepared according to the procedure described in Example 92 substituting 2-naphthol for methyl 3-hydroxybenzoate. $^1$H NMR (500 MHz, CDCl$_3$) δ ppm 7.83 (d, 1H), 7.70 (m, 2H), 7.61 (d, 1H), 7.40 (m, 1H), 7.30 (m, 2H), 7.12 (m, 2H), 7.06 (m, 1H), 6.97 (dd, 1H), 6.86 (d, 1H), 4.73 (m, 1H), 4.20 (m, 1H), 4.11 (m, 1H), 2.24 (m, 1H), 2.05 (m, 3H), 1.48 (d, 3H); MS (DCI/NH$_3$) m/z 373 [M+H]$^+$.

Example 96

1-(4-((4-((2-aminoquinolin-8-yl)oxy)pentyl)oxy)-3-methylphenyl)ethanone

The title compound was prepared according to the procedure described in Example 92 substituting 1-(4-hydroxy-3-methylphenyl)ethanone for methyl 3-hydroxybenzoate. $^1$H NMR (500 MHz, CDCl$_3$) δ ppm 7.94 (d, 1H), 7.74 (dd, 1H), 7.67 (m, 1H), 7.30 (t, 1H), 7.20 (m, 1H), 7.12 (d, 1H), 6.95 (d, 1H), 6.80 (d, 1H), 4.73 (m, 1H), 4.17 (m, 1H), 4.07 (m, 1H), 2.51 (s, 3H), 2.19 (m, 1H), 2.10 (s, 3H), 2.04 (m, 3H), 1.49 (d, 3H); MS (DCI/NH$_3$) m/z 379 [M+H]$^+$.

Example 97

8-(1-methyl-4-(4-propylphenoxy)butoxy)quinolin-2-amine

The title compound was prepared according to the procedure described in Example 92 substituting 4-propylphenol for methyl 3-hydroxybenzoate. $^1$H NMR (500 MHz, CDCl$_3$) δ ppm 7.93 (d, 1H), 7.29 (t, 1H), 7.18 (m, 1H), 7.13 (d, 1H), 7.02 (m, 3H), 6.74 (m, 2H), 4.70 (m, 1H), 4.00 (m, 2H), 2.49 (t, 2H), 2.20 (m, 1H), 1.97 (m, 3H), 1.59 (m, 2H), 1.46 (d, 3H), 0.91 (t, 3H); MS (DCI/NH$_3$) m/z 365 [M+H]$^+$.

Example 98

8-(4-(3-isopropylphenoxy)-1-methylbutoxy)quinolin-2-amine

The title compound was prepared according to the procedure described in Example 92 substituting 3-isopropylphenol for methyl 3-hydroxybenzoate. $^1$H NMR (500 MHz, CDCl$_3$) δ ppm 7.94 (d, 1H), 7.29 (t, 1H), 7.19 (m, 1H), 7.14 (m, 2H), 7.01 (d, 1H), 6.78 (m, 1H), 6.72 (m, 1H), 6.66 (m, 1H), 4.71 (m, 1H), 4.02 (m, 2H), 2.83 (t, 1H), 2.21 (m, 1H), 1.88–2.10 (m, 3H), 1.47 (d, 3H), 1.22 (d, 3H), 1.21 (d, 3H); MS (DCI/NH$_3$) m/z 365 [M+H]$^+$.

Example 99

8-(4-(4-chloro-3-fluorophenoxy)-1-methylbutoxy) quinolin-2-amine

The title compound was prepared according to the procedure described in Example 92 substituting 4-chloro-3-fluorophenol for methyl 3-hydroxybenzoate. $^1$H NMR (500 MHz, CDCl$_3$) δ ppm 7.96 (d, 1H), 7.31 (t, 1H), 7.19 (m, 2H), 7.12 (m, 1H), 6.99 (d, 1H), 6.55 (m, 2H), 4.69 (m, 1H), 4.04 (m, 1H), 3.95 (m, 1H), 2.19 (m, 1H), 1.87–2.09 (m, 3H), 1.46 (d, 3H); MS (DCI/NH$_3$) m/z 375 [M+H]$^+$.

Example 100

2-((4-((2-aminoquinolin-8-yl)oxy)pentyl)oxy)benzonitrile

The title compound was prepared according to the procedure described in Example 92 substituting 2-hydroxybenzonitrile for methyl 3-hydroxybenzoate. $^1$H NMR (500 MHz, CDCl$_3$) δ ppm 7.94 (d, 1H), 7.46 (m, 2H), 7.33 (t, 1H), 7.20 (m, 2H), 6.96 (m, 2H), 6.91 (m, 1H), 4.78 (m, 1H), 4.22 (m, 1H), 4.12 (m, 1H), 2.23 (m, 1H), 1.96–2.18 (m, 3H), 1.47 (d, 3H); MS (DCI/NH$_3$) m/z 348 [M+H]$^+$.

Example 101

2-((4-((2-aminoquinolin-8-yl)oxy)pentyl)oxy)benzamide

The title compound was prepared according to the procedure described in Example 92 substituting salicylamide for methyl 3-hydroxybenzoate. $^1$H NMR (500 MHz, DMSO-$d_6$) δ ppm 7.76 (dd, 1H), 7.35–7.58 (m, 6H), 7.10 (d, 1H), 7.01 (m, 1H), 4.87 (m, 1H), 4.18 (m, 2H), 1.84–2.05 (m, 4H), 1.40 (d, 3H); MS (DCI/NH$_3$) m/z 366 [M+H]$^+$.

Example 102

8-(1-methyl-4-(2-methyl-5-nitrophenoxy)butoxy)quinolin-2-amine

The title compound was prepared according to the procedure described in Example 92 substituting 2-methyl-5-nitrophenol for methyl 3-hydroxybenzoate. $^1$H NMR (500 MHz, CDCl$_3$) δ ppm 7.96 (d, 1H), 7.68 (dd, 1H), 7.59 (d, 1H), 7.30 (t, 1H), 7.21 (m, 1H), 7.18 (m, 1H), 7.13 (d, 1H), 7.01 (d, 1H), 4.71 (m, 1H), 4.15 (m, 1H), 4.08 (m, 1H), 2.25 (m, 1H), 2.21 (s, 3H), 2.12 (m, 1H), 2.01 (m, 2H), 1.49 (d, 3H); MS (DCI/NH$_3$) m/z 382 [M+H]$^+$.

Example 103

8-(4-((5-amino-1-naphthyl)oxy)-1-methylbutoxy)quinolin-2-amine

The title compound was prepared according to the procedure described in Example 92 substituting 5-amino-1-naphthol for methyl 3-hydroxybenzoate. $^1$H NMR (500 MHz, DMSO-$d_6$) δ ppm 8.36 (d, 1H), 7.56 (d, 1H), 7.48 (m, 2H), 7.39 (m, 2H), 7.27 (t, 1H), 7.17 (m, 1H), 7.12 (d, 1H), 6.87 (d, 1H), 6.80 (d, 1H), 4.92 (m, 1H), 4.17 (m, 2H), 2.04 (m, 4H), 1.45 (d, 3H); MS (DCI/NH$_3$) m/z 388 [M+H]$^+$.

Example 104

8-(4-(3-anilinophenoxy)-1-methylbutoxy)quinolin-2-amine

The title compound was prepared according to the procedure described in Example 92 substituting 3-anilinophenol for methyl 3-hydroxybenzoate. $^1$H NMR (500 MHz, CDCl$_3$) δ ppm 7.91 (d, 1H), 7.26 (m, 3H), 7.16 (m, 1H), 7.12 (m, 1H), 7.07 (m, 3H), 6.94 (d, 1H), 6.91 (m, 1H), 6.60 (m, 1H), 6.52 (t, 1H), 6.37 (m, 1H), 4.69 (m, 1H), 4.03 (m, 1H), 3.96 (m, 1H), 2.18 (m, 1H), 1.96 (m, 3H), 1.46 (d, 3H); MS (DCI/NH$_3$) m/z 414 [M+H]$^+$.

Example 105

8-(4-(2-chloro-4-methoxyphenoxy)-1-methylbutoxy)quinolin-2-amine

The title compound was prepared according to the procedure described in Example 92 substituting 2-chloro-4-methoxyphenol for methyl 3-hydroxybenzoate. $^1$H NMR (500 MHz, CDCl$_3$) δ ppm 7.94 (d, 1H), 7.29 (t, 1H), 7.18 (d, 1H), 7.15 (d, 1H), 6.99 (d, 1H), 6.85 (m, 2H), 6.70 (dd, 1H), 4.76 (m, 1H), 4.07 (m, 1H), 4.01 (m, 1H), 3.73 (s, 3H), 2.21 (m, 1H), 2.00 (m, 3H), 1.47 (d, 3H); MS (DCI/NH$_3$) m/z 387 [M+H]$^+$.

Example 106

8-(4-((4-methoxy-1-naphthyl)oxy)-1-methylbutoxy)quinolin-2-amine

The title compound was prepared according to the procedure described in Example 92 substituting 4-methoxy-1-naphthol for methyl 3-hydroxybenzoate. $^1$H NMR (500 MHz, CDCl$_3$) δ ppm 8.13 (m, 1H), 8.02 (m, 1H), 7.82 (d, 1H), 7.43 (m, 1H), 7.37 (m, 1H), 7.18 (t, 1H), 7.07 (m, 2H), 6.92 (d, 1H), 6.65 (m, 2H), 4.76 (m, 1H), 4.21 (m, 1H), 4.12 (m, 1H), 3.92 (s, 3H), 2.24 (m, 1H), 2.10 (m, 3H), 1.51 (d, 3H); MS (DCI/NH$_3$) m/z 403 [M+H]$^+$.

Example 107 methyl (4-((4-((2-aminoquinolin-8-yl)oxy)pentyl)oxy)phenyl)acetate

The title compound was prepared according to the procedure described in Example 92 substituting methyl (4-hydroxyphenyl)acetate for methyl 3-hydroxybenzoate. $^1$H NMR (500 MHz, CDCl$_3$) δ ppm 7.93 (d, 1H), 7.29 (t, 1H), 7.19 (m, 1H), 7.12 (m, 3H), 6.98 (d, 1H), 6.76 (m, 2H), 4.70 (m, 1H), 4.04 (m, 1H), 3.97 (m, 1H), 3.68 (s, 3H), 3.53 (s, 2H), 2.17 (m, 1H), 1.97 (m, 4H), 1.47 (d, 2H); MS (DCI/NH$_3$) m/z 395 [M+H]$^+$.

Example 108 ethyl 2-((4-((2-aminoquinolin-8-yl)oxy)pentyl)oxy)-5-methylbenzoate

The title compound was prepared according to the procedure described in Example 92 substituting ethyl 2-hydroxy-5-methylbenzoate for methyl 3-hydroxybenzoate. $^1$H NMR (500 MHz, CDCl$_3$) δ ppm 7.93 (d, 1H), 7.51 (d, 1H), 7.28 (t, 1H), 7.17 (m, 3H), 7.00 (d, 1H), 6.83 (d, 1H), 4.73 (m, 1H), 4.29 (m, 2H), 4.10 (m, 1H), 4.04 (m, 1H), 2.26 (s, 3H), 2.19 (m, 1H), 2.02 (m, 3H), 1.46 (d, 3H), 1.34 (t, 3H); MS (DCI/NH$_3$) m/z 409 [M+H]$^+$.

Example 109

8-(4-(4-bromo-2-fluorophenoxy)-1-methylbutoxy)quinolin-2-amine

The title compound was prepared according to the procedure described in Example 92 substituting 4-bromo-2-fluorophenol for methyl 3-hydroxybenzoate. 1H NMR (500 MHz, CDCl$_3$) δ ppm 7.95 (d, 1H), 7.30 (t, 1H), 7.20 (m, 1H), 7.12 (m, 3H), 6.98 (d, 1H), 6.81 (m, 1H), 4.72 (m, 1H), 4.13 (m, 1H), 4.05 (m, 1H), 2.21 (m, 1H), 2.03 (m, 3H), 1.46 (d, 3H); MS (DCI/NH$_3$) m/z 419/421 [M+H]$^+$.

Example 110

N-(3-((4-((2-aminoquinolin-8-yl)oxy)pentyl)oxy)phenyl)urea

The title compound was prepared according to the procedure described in Example 92 substituting N-(3-hydroxyphenyl)urea for methyl 3-hydroxybenzoate. $^1$H NMR (500 MHz, DMSO-$d_6$) δ ppm 8.36 (d, 1H), 7.47 (m, 2H), 7.42 (m, 1H), 7.17 (t, 1H), 7.13 (d, 1H), 7.06 (t, 1H), 6.77 (dd, 1H), 6.42 (dd, 1H), 4.86 (m, 1H), 3.97 (m, 2H), 2.01 (m, 1H), 1.88 (m, 3H), 1.40 (d, 3H); MS (DCI/NH$_3$) m/z 381 [M+H]$^+$.

Example 111

4-(4-((4-((2-aminoquinolin-8-yl)oxy)pentyl)oxy)phenyl)butan-2-one

The title compound was prepared according to the procedure described in Example 92 substituting 4-(4-hydroxyphenyl)butan-2-one for methyl 3-hydroxybenzoate. $^1$H NMR (500 MHz, CDCl$_3$) δ ppm 7.94 (d, 1H), 7.29 (t, 1H), 7.19 (d, 1H), 7.13 (d, 1H), 7.03 (m, 2H), 6.98 (m, 1H), 6.74 (m, 2H), 4.70 (m, 1H), 3.99 (m, 2H), 2.80 (t, 2H), 2.70 (t, 2H), 2.19 (m, 1H), 2.12 (s, 3H), 1.95 (m, 3H), 1.46 (d, 3H); MS (DCI/NH$_3$) m/z 393 [M+H]$^+$.

Example 112 ethyl 2-((4-((2-aminoquinolin-8-yl)oxy)pentyl)oxy)benzoate

The title compound was prepared according to the procedure described in Example 92 substituting ethyl salicylate for methyl 3-hydroxybenzoate. $^1$H NMR (500 MHz, CDCl$_3$) δ ppm 7.94 (d, 1H), 7.71 (dd, 1H), 7.40 (m, 1H), 7.28 (t, 1H), 7.16 (m, 2H), 7.00 (d, 1H), 6.94 (d, 1H), 6.90 (td, 1H), 4.74 (m, 1H), 4.30 (m, 2H), 4.14 (m, 1H), 4.08 (m, 1H), 2.20 (m, 1H), 1.93–2.15 (m, 3H), 1.46 (d, 3H), 1.34 (t, 3H); MS (DCI/NH$_3$) m/z 395 [M+H]$^+$.

Example 113 methyl 2-((4-((2-aminoquinolin-8-yl)oxy)pentyl)oxy)-5-methoxybenzoate

The title compound was prepared according to the procedure described in Example 92 substituting methyl 2-hydroxy-5-methoxybenzoate for methyl 3-hydroxybenzoate. $^1$H NMR (500 MHz, CDCl$_3$) δ ppm 7.94 (d, 1H), 7.28 (t, 1H), 7.25 (d, 1H), 7.17 (dd, 1H), 7.14 (d, 1H), 6.99 (m, 2H), 6.89 (d, 1H), 4.74 (m, 1H), 4.09 (m, 1H), 4.03 (m, 1H), 3.82 (s, 3H), 3.76 (s, 3H), 2.18 (m, 1H), 2.00 (m, 3H), 1.47 (d, 3H); MS (DCI/NH$_3$) m/z 411 [M+H]$^+$.

Example 114

8-(4-(4-amino-2-chlorophenoxy)-1-methylbutoxy)quinolin-2-amine

The title compound was prepared according to the procedure described in Example 92 substituting 4-amino-2-chlorophenol for methyl 3-hydroxybenzoate. $^1$H NMR (500 MHz, DMSO-d6) δ ppm 8.37 (d, 1H), 7.48 (m, 2H), 7.41 (m, 1H), 7.13 (d, 1H), 6.96 (d, 1H), 6.90 (d, 1H), 6.75 (dd, 1H), 4.88 (m, 1H), 4.00 (m, 2H), 2.01 (m, 1H), 1.88 (m, 3H), 1.40 (d, 3H); MS (DCI/NH$_3$) m/z 372 [M+H]$^+$.

Example 115

1-(4-((4-((2-aminoquinolin-8-yl)oxy)pentyl)oxy)phenyl)propan-1-one

The title compound was prepared according to the procedure described in Example 92 substituting 1-(4-hydroxyphenyl)propan-1-one for methyl 3-hydroxybenzoate. $^1$H NMR (500 MHz, CDCl$_3$) δ ppm 7.94 (d, 1H), 7.86 (m, 2H), 7.30 (t, 1H), 7.20 (m, 1H), 7.12 (d, 1H), 6.97 (d, 1H), 6.82 (m, 2H), 4.70 (m, 1H), 4.14 (m, 1H), 4.06 (m, 1H), 2.92 (q, 2H), 2.22 (m, 1H), 2.07 (m, 1H), 1.97 (m, 2H), 1.47 (d, 3H), 1.20 (t, 3H); MS (DCI/NH$_3$) m/z 379 [M+H]$^+$.

Example 116

8-(4-(3-(diethylamino)phenoxy)-1-methylbutoxy)quinolin-2-amine

The title compound was prepared according to the procedure described in Example 92 substituting 3-(diethylamino)phenol for methyl 3-hydroxybenzoate. $^1$H NMR (500 MHz, CDCl$_3$) δ ppm 7.97 (d, 1H), 7.32 (t, 1H), 7.28 (m, 1H), 7.21 (dd, 1H), 7.15 (d, 1H), 7.06 (d, 1H), 6.90 (m, 2H), 6.74 (m, 1H), 4.69 (m, 1H), 4.11 (m, 1H), 4.05 (m, 1H), 3.49 (m, 4H), 2.21 (m, 1H), 2.08 (m, 1H), 1.93 (m, 2H), 1.46 (d, 3H), 1.11 (t, 6H); MS (DCI/NH$_3$) m/z 394 [M+H]$^+$.

Example 117

8-(4-(isoquinolin-5-yloxy)-1-methylbutoxy)quinolin-2-amine

The title compound was prepared according to the procedure described in Example 92 substituting isoquinolin-5-ol for methyl 3-hydroxybenzoate. $^1$H NMR (500 MHz, CDCl$_3$) δ ppm 9.43 (s, 1H), 8.36 (d, 1H), 8.26 (d, 1H), 7.89 (d, 1H), 7.74 (t, 1H), 7.68 (d, 1H), 7.29 (m, 2H), 7.13 (m, 2H), 6.93 (d, 1H), 4.77 (m, 1H), 4.43 (m, 1H), 4.28 (m, 1H), 2.06–2.34 (m, 4H), 1.51 (d, 3H); MS (DCI/NH$_3$) m/z 374 [M+H]$^+$.

Example 118

8-(4-(1,1'-biphenyl-3-yloxy)-1-methylbutoxy)quinolin-2-amine

The title compound was prepared according to the procedure described in Example 92 substituting 1,1'-biphenyl-3-ol for methyl 3-hydroxybenzoate. $^1$H NMR (500 MHz, CDCl$_3$) δ ppm 7.90 (d, 1H), 7.54 (m, 2H), 7.41 (m, 2H), 7.30 (m, 3H), 7.13 (m, 3H), 7.02 (t, 1H), 6.98 (d, 1H), 6.81 (dd, 1H), 4.72 (m, 1H), 4.12 (m, 1H), 4.05 (m, 1H), 2.21 (m, 1H), 2.00 (m, 3H), 1.47 (d, 3H); MS (DCI/NH$_3$) m/z 399 [M+H]$^+$.

Example 119

8-(4-(2-fluoro-5-methylphenoxy)-1-methylbutoxy)quinolin-2-amine

The title compound was prepared according to the procedure described in Example 92 substituting 2-fluoro-5-methylphenol for methyl 3-hydroxybenzoate. $^1$H NMR (500 MHz, CDCl$_3$) δ ppm 7.93 (d, 1H), 7.29 (t, 1H), 7.18 (m, 1H), 7.15 (d, 1H), 7.00 (d, 1H), 6.86 (dd, 1H), 6.74 (dd, 1H), 6.61 (m, 1H), 4.74 (m, 1H), 4.11 (m, 1H), 4.05 (m, 1H), 2.26 (s, 3H), 2.21 (m, 1H), 2.01 (m, 3H), 1.46 (d, 3H); MS (DCI/NH$_3$) m/z 355 [M+H]$^+$.

Example 120

8-(4-(2-ethoxy-5-((1E)-prop-1-enyl)phenoxy)-1-methylbutoxy)quinolin-2-amine

The title compound was prepared according to the procedure described in Example 92 substituting 2-ethoxy-5-[(1E)-prop-1-enyl]phenol for methyl 3-hydroxybenzoate.

¹H NMR (500 MHz, CDCl₃) δ ppm 7.93 (d, 1H), 7.27 (m, 1H), 7.16 (m, 2H), 7.01 (d, 1H), 6.88 (d, 1H), 6.75 (m, 2H), 6.28 (dd, 1H), 6.06 (m, 1H), 4.77 (m, 1H), 4.06 (m, 4H), 2.21 (m, 1H), 2.01 (m, 3H), 1.84 (m, 3H), 1.47 (d, 3H), 1.36 (t, 3H); MS (DCI/NH₃) m/z 407 [M+H]⁺.

Example 121 methyl 2-((4-((2-aminoquinolin-8-yl)oxy)pentyl)oxy)-4-methoxybenzoate

The title compound was prepared according to the procedure described in Example 92 substituting methyl 2-hydroxy-4-methoxybenzoate for methyl 3-hydroxybenzoate. ¹H NMR (500 MHz, CDCl₃) δ ppm 7.92 (d, 1H), 7.75 (d, 1H), 7.28 (t, 1H), 7.16 (m, 2H), 6.99 (d, 1H), 6.45 (d, 1H), 6.41 (dd,1 1H), 4.77 (m, 1H), 4.15 (m, 1H), 4.06 (m, 1H), 3.81 (s, 3H), 3.78 (s, 3H), 2.21 (m, 1H), 2.05 (m, 3H), 1.48 (d, 3H); MS (DCI/NH₃) m/z 411 [M+H]⁺.

Example 122

8-(4-(2-benzylphenoxy)-1-methylbutoxy)quinolin-2-amine

The title compound was prepared according to the procedure described in Example 92 substituting 2-benzylphenol for methyl 3-hydroxybenzoate. ¹H NMR (500 MHz, CDCl₃) δ ppm 7.91 (d, 1H), 7.26 (m, 1H), 7.21 (m, 2H), 7.17 (m, 1H), 7.13 (m, 4H), 7.07 (d, 1H), 7.02 (dd, 1H), 6.98 (d, 1H), 6.82 (m, 2H), 4.62 (m, 1H), 3.99 (m, 2H), 3.87 (m, 2H), 2.10 (m, 1H), 2.00 (m, 1H), 1.88 (m, 2H), 1.42 (d, 3H); MS (DCI/NH₃) m/z 413 [M+H]⁺.

Example 123

8-(4-(2-fluoro-4-nitrophenoxy)-1-methylbutoxy)quinolin-2-amine

The title compound was prepared according to the procedure described in Example 92 substituting 2-fluoro-4-nitrophenol for methyl 3-hydroxybenzoate. ¹H NMR (500 MHz, CDCl₃) δ ppm 7.98 (m, 2H), 7.84 (dd, 1H), 7.32 (t, 1H), 7.21 (d, 1H), 7.14 (d, 1H), 7.02 (m, 1H), 6.94 (d, 1H), 4.73 (m, 1H), 4.31 (m, 1H), 4.20 (m, 1H), 2.11–2.31 (m, 2H), 2.04 (m, 2H), 1.46 (d, 3H); MS (DCI/NH₃) m/z 386 [M+H]⁺.

Example 124

5-acetyl-2-((4-((2-aminoquinolin-8-yl)oxy)pentyl)oxy)benzamide

The title compound was prepared according to the procedure described in Example 92 substituting 5-acetyl-2-hydroxybenzamide for methyl 3-hydroxybenzoate. ¹H NMR (500 MHz, CDCl₃) δ ppm 8.66 (d, 1H), 8.06 (dd, 1H), 7.96 (d, 1H), 7.32 (t, 1H), 7.22 (m, 1H), 7.12 (d, 1H), 7.04 (d, 1H), 6.97 (d, 1H), 4.71 (m, 1H), 4.38 (m, 1H), 4.26 (m, 1H), 2.58 (s, 3H), 2.24 (m, 2H), 1.92–2.13 (m, 2H), 1.48 (d, 3H); MS (DCI/NH₃) m/z 408 [M+H]⁺.

Example 125

8-(4-(2,3-dihydro-1H-inden-5-yloxy)-1-methylbutoxy)quinolin-2-amine

The title compound was prepared according to the procedure described in Example 92 substituting indan-5-ol for methyl 3-hydroxybenzoate. ¹H NMR (500 MHz, CDCl₃) δ ppm 7.93 (d, 1H), 7.28 (t, 1H), 7.18 (m, 1H), 7.12 (d, 1H), 7.03 (d, 1H), 7.00 (d, 1H), 6.70 (d, 1H), 6.60 (dd, 1H), 4.70 (m, 1H), 4.00 (m, 2H), 2.82 (m, 4H), 2.19 (m, 1H), 1.88–2.09 (m, 5H), 1.46 (d, 3H); MS (DCI/NH₃) m/z 363 [M+H]⁺.

Example 126

8-(4-(4-(1H-imidazol-1-yl)phenoxy)-1-methylbutoxy)quinolin-2-amine

The title compound was prepared according to the procedure described in Example 92 substituting 4-(1H-imidazol-1-yl)phenol for methyl 3-hydroxybenzoate. ¹H NMR (500 MHz, CDCl₃) δ ppm 8.89 (s, 1H), 7.93 (d, 1H), 7.45 (s, 1H), 7.38 (s, 1H), 7.32 (m, 3H), 7.20 (dd, 1H), 7.12 (d, 1H), 7.06 (d, 1H), 6.96 (m, 2H), 4.69 (m, 1H), 4.21 (m, 1H), 4.10 (m, 1H), 2.23 (m, 1H), 2.12 (m, 1H), 1.94 (m, 2H), 1.48 (d, 3H); MS (DCI/NH₃) m/z 389 [M+H]⁺.

Example 127

8-(4-(dibenzo[b,d]furan-2-yloxy)-1-methylbutoxy)quinolin-2-amine

The title compound was prepared according to the procedure described in Example 92 substituting dibenzo[b,d]furan-2-ol for methyl 3-hydroxybenzoate. ¹H NMR (500 MHz, CDCl₃) δ ppm 7.86 (m, 1H), 7.79 (d, 1H), 7.51 (m, 1H), 7.42 (m, 1H), 7.34 (d, 1H), 7.28 (m, 3H), 7.11 (d, 2H), 6.90 (dd, 1H), 6.84 (d, 1H), 4.74 (m, 1H), 4.20 (m, 1H), 4.10 (m, 1H), 2.23 (m, 1H), 2.04 (m, 3H), 1.49 (d, 3H); MS (DCI/NH₃) m/z 413 [M+H]⁺.

Example 128

8-(4-((2,2-dimethyl-2,3-dihydro-1-benzofuran-7-yl)oxy)-1-methylbutoxy)quinolin-2-amine The title compound was prepared according to the procedure described in Example 92 substituting 2,2-dimethyl-2,3-dihydro-1-benzofuran-7-ol for methyl 3-hydroxybenzoate. ¹H NMR (500 MHz, CDCl₃) δ ppm 7.94 (d, 1H), 7.28 (m, 1H), 7.18 (m, 1H), 7.14 (d, 1H), 7.02 (d, 1H), 6.72 (m, 3H), 4.72 (m, 1H), 4.11 (m, 2H), 2.99 (s, 2H), 2.19 (m, 1H), 1.97 (m, 3H), 1.47 (s, 3H), 1.47 (s, 3H), 1.44 (d, 3H); MS (DCI/NH₃) m/z 393 [M+H]⁺.

Example 129

8-(4-(2-isoxazol-5-ylphenoxy)-1-methylbutoxy)quinolin-2-amine

The title compound was prepared according to the procedure described in Example 92 substituting 2-isoxazol-5-ylphenol for methyl 3-hydroxybenzoate. ¹H NMR (500 MHz, CDCl₃) δ ppm 8.20 (d, 1H), 7.92 (d, 1H), 7.86 (dd, 1H), 7.34 (m, 1H), 7.23 (t, 1H), 7.16 (dd, 1H), 7.05 (d, 1H), 6.97 (m, 3H), 6.68 (d, 1H), 4.71 (m, 1H), 4.26 (m, 1H), 4.15 (m, 1H), 1.98–2.26 (m, 4H), 1.48 (d, 3H); MS (DCI/NH$_3$) m/z 390 [M+H]$^+$.

Example 130

6-((4-((2-aminoquinolin-8-yl)oxy)pentyl)oxy)-1,3-benzoxathiol-2-one

The title compound was prepared according to the procedure described in Example 92 substituting 6-hydroxy-1,3-benzoxathiol-2-one for methyl 3-hydroxybenzoate. $^1$H NMR (500 MHz, CDCl$_3$) δ ppm 7.97 (d, 1H), 7.32 (t, 1H), 7.21 (dd, 1H), 7.17 (d, 1H), 7.13 (d, 1H), 6.95 (d, 1H), 6.74 (dd, 1H), 6.71 (d, 1H), 4.70 (m, 1H), 4.09 (m, 1H), 4.00 (m, 1H), 2.21 (m, 1H), 2.01 (m, 3H), 1.47 (d, 3H); MS (DCI/NH$_3$) m/z 397 [M+H]$^+$.

Example 131

8-(4-(2-methoxy-4-propylphenoxy)-1-methylbutoxy)quinolin-2-amine

The title compound was prepared according to the procedure described in Example 92 substituting 4-allyl-2-methoxyphenol for methyl 3-hydroxybenzoate. $^1$H NMR (500 MHz, CDCl$_3$) δ ppm 7.93 (d, 1H), 7.28 (m, 1H), 7.16 (m, 2H), 7.01 (d, 1H), 6.79 (m, 1H), 6.66 (m, 2H), 4.73 (m, 1H), 4.05 (m, 2H), 3.79 (s, 3H), 2.50 (m, 2H), 2.21 (m, 1H), 1.99 (m, 3H), 1.61 (m, 2H), 1.45 (d, 3H), 0.92 (t, 3H); MS (DCI/NH$_3$) m/z 395 [M+H]$^+$.

Example 132

8-(4-(2-chloro-3-(trifluoromethyl)phenoxy)-1-methylbutoxy)quinolin-2-amine

The title compound was prepared according to the procedure described in Example 92 substituting 2-chloro-3-(triflouromethyl)phenol for methyl 3-hydroxybenzoate. $^1$H NMR (500 MHz, DMSO-d$_6$) δ ppm 8.35 (d, 1H), 7.47 (m, 4H), 7.39 (m, 2H), 7.12 (d, 1H), 4.89 (m, 1H), 4.20 (m, 2H), 1.83–2.08 (m, 4H), 1.42 (d, 3H); MS (DCI/NH$_3$) m/z 426 [M+H]$^+$.

Example 133

8-(1-methyl-4-(2-methylphenoxy)butoxy)quinolin-2-amine

The title compound was prepared according to the procedure described in Example 92 substituting o-cresol for methyl 3-hydroxybenzoate. 1H NMR (500 MHz, DMSO-d$_6$) δ ppm 8.36 (d, 1H), 7.48 (m, 2H), 7.39 (m, 1H), 7.09 (m, 3H), 6.87 (d, 1H), 6.76 (m, 1H), 4.89 (m, 1H), 4.02 (m, 2H), 2.06 (m, 3H), 1.82–2.04 (m, 4H), 1.42 (d, 3H); MS (DCI/NH$_3$) m/z 337 [M+H]$^+$.

Example 134

8-(1-methyl-4-(3-methylphenoxy)butoxy)quinolin-2-amine

The title compound was prepared according to the procedure described in Example 92 substituting m-cresol for methyl 3-hydroxybenzoate. $^1$H NMR (500 MHz, DMSO-d$_6$) δ ppm 8.36 (d, 1H), 7.47 (m, 2H), 7.40 (m, 1H), 7.10 (m, 2H), 6.70 (d, 1H), 6.64 (m, 2H), 4.86 (m, 1H), 3.97 (m, 2H), 2.22 (m, 3H), 2.00 (m, 1H), 1.87 (m, 3H), 1.40 (d, 3H); MS (DCI/NH$_3$) m/z 337 [M+H]$^+$.

Example 135

8-(1-methyl-4-(4-methylphenoxy)butoxy)quinolin-2-amine

The title compound was prepared according to the procedure described in Example 92 substituting o-cresol for methyl 3-hydroxybenzoate. $^1$H NMR (500 MHz, DMSO-d$_6$) δ ppm 8.36 (d, 1H), 7.48 (m, 3H), 7.40 (m, 2H), 7.13 (d, 1H), 7.02 (m, 1H), 6.74 (m, 1H), 4.83 (m, 1H), 3.99 (m, 2H), 2.22 (m, 3H), 1.76–2.08 (m, 4H), 1.40 (d, 3H); MS (DCI/NH$_3$), m/z 337 [M+H]$^+$.

Example 136

8-(4-(2-chloro-5-methylphenoxy)-1-methylbutoxy)quinolin-2-amine

The title compound was prepared according to the procedure described in Example 92 substituting 2-chloro-4-methylphenol for methyl 3-hydroxybenzoate. $^1$H NMR (500 MHz, DMSO-d$_6$) δ ppm 8.36 (d, 1H), 7.43 (m, 3H), 7.21 (d, 1H), 7.12 (d, 1H), 6.91 (m, 1H), 6.72 (m, 1H), 4.89 (m, 1H), 4.10 (m, 2H), 2.26 (m, 3H), 1.94 (m, 4H), 1.42 (d, 3H); MS (DCI/NH$_3$) m/z 371 [M+H]$^+$.

Example 137

4-((4-((2-aminoquinolin-8-yl)oxy)pentyl)oxy)phenol

The title compound was prepared according to the procedure described in Example 92 substituting hydroquinone for methyl 3-hydroxybenzoate. $^1$H NMR (500 MHz, DMSO-D6) δ ppm 8.38 (m, 1H), 7.47 (m, 2H), 7.40 (m, 1H), 7.14 (m, 1H), 6.69 (m, 2H), 6.62 (m, 2H), 4.85 (m, 1H), 3.90 (m, 2H), 3.69 (m, 1H), 1.96 (m, 1H), 1.83 (m, 3H), 1.39 (m, 3H); MS (DCI/NH$_3$) m/z 339 [M+H]$^+$.

Example 138

8-(4-(3-methoxyphenoxy)-1-methylbutoxy)quinolin-2-amine

The title compound was prepared according to the procedure described in Example 92 substituting 3-methoxyphenol for methyl 3-hydroxybenzoate. $^1$H NMR (500 MHz, DMSO-d$_6$) δ ppm 8.36 (d, 1H), 7.44 (m, 3H), 7.13 (m, 2H), 6.47 (m, 2H), 6.38 (m, 1H), 4.84 (m, 1H), 4.01 (m, 2H), 3.69 (m, 3H), 1.78–2.06 (m, 4H), 1.40 (d, 3H); MS (DCI/NH$_3$) m/z 353 [M+H]$^+$.

Example 139

8-(4-(4-methoxyphenoxy)-1-methylbutoxy)quinolin-2-amine

The title compound was prepared according to the procedure described in Example 92 substituting 4-methoxyphenol for methyl 3-hydroxybenzoate. $^1$H NMR (500 MHz, DMSO-d$_6$) δ ppm 8.36 (d, 1H), 7.43 (m, 3H), 7.13 (d, 1H), 6.78 (m, 4H), 4.84 (m, 1H), 3.97 (m, 2H), 3.68 (m, 3H), 1.73–2.07 (m, 4H), 1.40 (d, 3H); MS (DCI/NH$_3$) m/z 353 [M+H]$^+$.

Example 140

8-(4-(2-fluorophenoxy)-1-methylbutoxy)quinolin-2-amine

The title compound was prepared according to the procedure described in Example 92 substituting 2-flourophenol for methyl 3-hydroxybenzoate. $^1$H NMR (500 MHz, DMSO-d$_6$) δ ppm 8.36 (d, 1H), 7.45 (m, 3H), 7.12 (m, 4H), 6.89 (m, 1H), 4.86 (m, 1H), 4.09 (m, 2H), 1.73–2.10 (m, 4H), 1.40 (d, 3H); MS (DCI/NH$_3$) m/z 341 [M+H]$^+$.

Example 141

8-(4-(3-fluorophenoxy)-1-methylbutoxy)quinolin-2-amine

The title compound was prepared according to the procedure described in Example 92 substituting 3-flourophenol for methyl 3-hydroxybenzoate. $^1$H NMR (500 MHz, DMSO-d$_6$) δ ppm 8.36 (d, 1H), 7.45 (m, 3H), 7.26 (m, 1H), 7.12 (d, 1H), 6.70 (m, 3H), 4.65–4.94 (m, 1H), 3.90–4.14 (m, 2H), 1.73–2.07 (m, 4H), 1.40 (d, 3H); MS (DC/NH$_3$) m/z 341 [M+H]$^+$.

Example 142

8-(4-(4-fluorophenoxy)-1-methylbutoxy)quinolin-2-amine

The title compound was prepared according to the procedure described in Example 92 substituting 4-flourophenol for methyl 3-hydroxybenzoate. $^1$H NMR (500 MHz, DMSO-d$_6$) δ ppm 8.36 (d, 1H), 7.43 (m, 3H), 7.13 (d, 1H), 7.05 (m, 2H), 6.71–6.94 (m, 2H), 4.87 (m, 1H), 3.85–4.13 (m, 2H), 1.71–2.08 (m, 4H), 1.40 (d, 3H); MS (DCI/NH$_3$) m/z 341 [M+H]$^+$.

Example 143

8-(4-(2-chlorophenoxy)-1-methylbutoxy)quinolin-2-amine

The title compound was prepared according to the procedure described in Example 92 substituting 2-chlorophenol for methyl 3-hydroxybenzoate. $^1$H NMR (500 MHz, DMSO-d$_6$) δ ppm 8.36 (d, 1H), 7.43 (m, 3H), 7.27 (m, 1H), 7.13 (m, 2H), 6.92 (m, 2H), 4.77–5.00 (m, 1H), 4.10 (m, 2H), 1.78–2.12 (m, 4H), 1.41 (d, 3H); MS (DCI/NH$_3$) m/z 358 [M+H]$^+$.

Example 144

8-(4-(3-chlorophenoxy)-1-methylbutoxy)quinolin-2-amine

The title compound was prepared according to the procedure described in Example 92 substituting 3-chlorophenol for methyl 3-hydroxybenzoate. $^1$H NMR (500 MHz, DMSO-d$_6$) δ ppm 8.37 (m, 1H), 7.43 (m, 3H), 7.26 (m, 1H), 7.13 (m, 1H), 6.93 (m, 2H), 6.82 (m, 2H), 4.73–4.94 (m, 1H), 3.79–4.12 (m, 2H), 1.69–2.07 (m, 4H), 1.40 (m, 3H); MS (DCI/NH$_3$) m/z 358 [M+H]$^+$.

Example 145

8-(4-(4-chlorophenoxy)-1-methylbutoxy)quinolin-2-amine

The title compound was prepared according to the procedure described in Example 92 substituting 4-chlorophenol for methyl 3-hydroxybenzoate. $^1$H NMR (500 MHz, DMSO-d$_6$) δ ppm 8.36 (d, 1H), 7.44 (m, 3H), 7.27 (m, 2H), 7.12 (d, 1H), 6.88 (m, 2H), 4.88 (m, 1H), 3.89–4.15 (m, 2H), 1.68–2.06 (m, 4H), 1.40 (d, 3H); MS (DCI/NH$_3$) m/z 358 [M+H]$^+$.

Example 146

8-(4-(2-bromophenoxy)-1-methylbutoxy)quinolin-2-amine

The title compound was prepared according to the procedure described in Example 92 substituting 2-bromophenol for methyl 3-hydroxybenzoate. $^1$H NMR (500 MHz, DMSO-d$_6$) δ ppm 8.36 (d, 1H), 7.50 (m, 3H), 7.40 (m, 1H), 7.30 (m, 1H), 7.13 (d, 1H), 7.08 (m, 1H), 6.84 (m, 1H), 4.89 (m, 1H), 4.12 (m, 2H), 1.76–2.10 (m, 4H), 1.42 (d, 3H); MS (DCI/NH$_3$) m/z 402 [M+H]$^+$.

Example 147

8-(4-(3-bromophenoxy)-1-methylbutoxy)quinolin-2-amine

The title compound was prepared according to the procedure described in Example 92 substituting 3-bromophenol for methyl 3-hydroxybenzoate. $^1$H NMR (500 MHz, DMSO-d$_6$) δ ppm 8.36 (d, 1H), 7.45 (m, 3H), 7.20 (m, 1H), 7.12 (d, 1H), 7.08 (m, 1H), 7.03 (m, 1H), 6.87 (m, 1H), 4.86 (m, 1H), 4.05 (m, 2H), 1.74–2.07 (m, 4H), 1.40 (d, 3H); MS (DCI/NH$_3$) m/z 402 [M+H]$^+$.

Example 148

8-(4-(4-bromophenoxy)-1-methylbutoxy)quinolin-2-amine

The title compound was prepared according to the procedure described in Example 92 substituting 4-bromophenol for methyl 3-hydroxybenzoate. $^1$H NMR (500 MHz, DMSO-d$_6$) δ ppm 8.36 (d, 1H), 7.45 (m, 5H), 7.13 (m, 1H), 6.83 (m, 2H), 4.86 (m, 1H), 4.03 (m, 2H), 1.73–2.10 (m, 4H), 1.40 (d, 3H); MS (DCI/NH$_3$) m/z 402 [M+H]$^+$.

Example 149

3-((4-((2-aminoquinolin-8-yl)oxy)pentyl)oxy)benzonitrile

The title compound was prepared according to the procedure described in Example 92 substituting 3-cyanophenol for methyl 3-hydroxybenzoate. $^1$H NMR (500 MHz, DMSO-d$_6$) δ ppm 8.36 (d, 1H), 7.47 (m, 2H), 7.42 (m, 2H), 7.35 (m, 1H), 7.31 (m, 1H), 7.20 (m, 1H), 7.12 (d, 1H), 4.87 (m, 1H), 4.10 (m, 2H), 1.78–2.07 (m, 4H), 1.40 (d, 3H); MS (DCI/NH$_3$) m/z 348 [M+H]$^+$.

Example 150

4-((4-((2-aminoquinolin-8-yl)oxy)pentyl)oxy)benzonitrile

The title compound was prepared according to the procedure described in Example 92 substituting 4-cyanophenol for methyl 3-hydroxybenzoate. $^1$H NMR (500 MHz, DMSO-d$_6$) δ ppm 8.36 (d, 1H), 7.70 (m, 2H), 7.44 (m, 3H), 7.12 (d, 1H), 7.00 (m, 2H), 4.84 (m, 1H), 4.12 (m, 2H), 1.74–2.05 (m, 4H), 1.40 (d, 3H); MS (DCI/NH$_3$) m/z 348 [M+H]$^+$.

Example 151

8-(1-methyl-4-(3-(trifluoromethyl)phenoxy)butoxy)quinolin-2-amine

The title compound was prepared according to the procedure described in Example 92 substituting 3-(triflouromethyl)phenol for methyl 3-hydroxybenzoate. $^1$H NMR (500 MHz, DMSO-d$_6$) δ ppm 8.36 (d, 1H), 7.48 (m, 3H), 7.41 (m, 1H), 7.25 (m, 1H), 7.18 (m, 1H), 7.12 (m, 2H), 4.86 (m, 1H), 3.96–4.17 (m, 2H), 1.79–2.06 (m, 4H), 1.41 (d, 3H); MS (DCI/NH$_3$) m/z 391 [M+H]$^+$.

Example 152

8-(1-methyl-4-(4-(trifluoromethyl)phenoxy)butoxy)quinolin-2-amine

The title compound was prepared according to the procedure described in Example 92 substituting 4-(triflouromethyl)phenol for methyl 3-hydroxybenzoate. $^1$H NMR (500 MHz, DMSO-d$_6$) δ ppm 8.36 (d, 1H), 7.58 (m, 2H), 7.45 (m, 3H), 7.12 (d, 1H), 7.02 (m, 2H), 4.76–4.96 (m, 1H), 4.13 (m, 2H), 1.80–2.06 (m, 4H), 1.40 (d, 3H); MS (DCI/NH$_3$) m/z 391 [M+H]$^+$.

Example 153

8-(1-methyl-4-(3-(trifluoromethoxy)phenoxy)butoxy)quinolin-2-amine

The title compound was prepared according to the procedure described in Example 92 substituting 3-(triflouromethoxy)phenol for methyl 3-hydroxybenzoate. $^1$H NMR (500 MHz, DMSO-d$_6$) δ ppm 8.36 (d, 1H), 7.48 (m, 2H), 7.38 (m, 2H), 7.12 (d, 1H), 6.91 (m, 2H), 6.81 (m, 1H), 4.75–4.97 (m, 1H), 3.94–4.18 (m, 2H), 1.78–2.06 (m, 4H), 1.40 (d, 3H); MS (DCI/NH$_3$) m/z 407 [M+H]$^+$.

Example 154

8-(4-(2,3-dimethylphenoxy)-1-methylbutoxy)quinolin-2-amine

The title compound was prepared according to the procedure described in Example 92 substituting 2,3-dimethylphenol for methyl 3-hydroxybenzoate. $^1$H NMR (500 MHz, DMSO-d$_6$) δ ppm 8.35 (d, 1H), 7.43 (m, 3H), 7.12 (m, 1H), 6.98 (m, 1H), 6.70 (m, 2H), 4.89 (m, 1H), 3.88–4.08 (m, 2H), 2.18 (m, 3H), 2.01 (m, 1H), 1.96 (m, 3H), 1.88 (m, 3H), 1.42 (d, 3H); MS (DCI/NH$_3$) m/z 351 [M+H]$^+$.

Example 155

8-(4-(2,4-dimethylphenoxy)-1-methylbutoxy)quinolin-2-amine

The title compound was prepared according to the procedure described in Example 92 substituting 2,4-dimethylphenol for methyl 3-hydroxybenzoate. $^1$H NMR (500 MHz, DMSO-d$_6$) δ ppm 8.35 (d, 1H), 7.43 (m, 3H), 7.12 (d, 1H), 6.89 (m, 2H), 6.75 (m, 1H), 4.77–4.98 (m, 1H), 3.99 (m, 2H), 2.18 (m, 3H), 1.99 (m, 4H), 1.88 (m, 3H), 1.41 (d, 3H); MS (DCI/NH$_3$) m/z 351 [M+H]$^+$.

Example 156

8-(4-(2,5-dimethylphenoxy)-1-methylbutoxy)quinolin-2-amine

The title compound was prepared according to the procedure described in Example 92 substituting 2,5-dimethylphenol for methyl 3-hydroxybenzoate. $^1$H NMR (500 MHz, DMSO-d$_6$) δ ppm 8.35 (d, 1H), 7.44 (m, 3H), 7.11 (d, 1H), 6.92 (d, 1H), 6.70 (m, 1H), 6.58 (m, 1H), 4.88 (m, 1H), 3.99 (m, 2H), 2.24 (m, 3H), 1.80–2.04 (m, 7H), 1.42 (d, 3H); MS (DCI/NH$_3$) m/z 351 [M+H]$^+$.

Example 157

8-(4-(3,4-dimethylphenoxy)-1-methylbutoxy)quinolin-2-amine

The title compound was prepared according to the procedure described in Example 92 substituting 3,4-dimethylphenol for methyl 3-hydroxybenzoate. $^1$H NMR (500 MHz, DMSO-d$_6$) δ ppm 8.37 (m, 1H), 7.43 (m, 3H), 7.13 (m, 1H), 6.96 (m, 1H), 6.57 (m, 2H), 4.82 (m, 1H), 3.76–4.05 (m, 2H), 2.11 (m, 6H), 1.73–2.02 (m, 4H), 1.38 (m, 3H); MS (DCI/NH$_3$) m/z 351 [M+H]$^+$.

Example 158

8-(4-(3,5-dimethylphenoxy)-1-methylbutoxy)quinolin-2-amine

The title compound was prepared according to the procedure described in Example 92 substituting 3,5-dimethylphenol for methyl 3-hydroxybenzoate. $^1$H NMR (500 MHz, DMSO-d$_6$) δ ppm 8.37 (m, 1H), 7.31–7.52 (m, 3H), 7.12 (m, 1H), 6.53 (m, 1H), 6.27–6.47 (m, 2H), 4.67–4.98 (m, 1H), 3.88–4.10 (m, 2H), 2.16 (m, 6H), 1.73–2.06 (m, 4H), 1.41 (m, 3H); MS (DCI/NH$_3$) m/z 351 [M+H]$^+$.

Example 159

8-(4-(1,3-benzodioxol-5-yloxy)-1-methylbutoxy)quinolin-2-amine

The title compound was prepared according to the procedure described in Example 92 substituting sesamol for methyl 3-hydroxybenzoate. $^1$H NMR (500 MHz, DMSO-d$_6$) δ ppm 8.39 (m, 1H), 7.43 (m, 3H), 7.10 (m, 1H), 6.72 (m, 1H), 6.49 (m, 1H), 6.26 (m, 1H), 5.93 (m, 2H), 4.64–4.96 (m, 1H), 3.76–4.01 (m, 2H), 1.74–2.03 (m, 4H), 1.39 (m, 3H); MS (DCI/NH$_3$) m/z 367 [M+H]$^+$.

Example 160

8-(4-(2,3-dichlorophenoxy)-1-methylbutoxy)quinolin-2-amine

The title compound was prepared according to the procedure described in Example 92 substituting 2,3-dichlorophenol for methyl 3-hydroxybenzoate. $^1$H NMR (500 MHz, DMSO-d$_6$) δ ppm 8.37 (m, 1H), 7.45 (m, 3H), 7.28 (m, 1H), 7.12 (m, 3H), 4.91 (m, 1H), 4.00–4.26 (m, 2H), 1.71–2.08 (m, 4H), 1.42 (m, 3H); MS (DCI/NH$_3$) m/z 392 [M+H]$^+$.

Example 161

8-(4-(2,4-dichlorophenoxy)-1-methylbutoxy)quinolin-2-amine

The title compound was prepared according to the procedure described in Example 92 substituting 2,4-dichlorophenol for methyl 3-hydroxybenzoate. $^1$H NMR (500 MHz, DMSO-d$_6$) δ ppm 8.36 (m, 1H), 7.31–7.58 (m, 5H), 6.95–7.24 (m, 2H), 4.74–5.11 (m, 1H), 3.84–4.11 (m, 2H), 1.80–2.14 (m, 4H), 1.41 (m, 3H); MS (DCI/NH$_3$) m/z 392 [M+H]$^+$.

Example 162

8-(4-(2,5-dichlorophenoxy)-1-methylbutoxy)quinolin-2-amine

The title compound was prepared according to the procedure described in Example 92 substituting 2,5-dichlorophenol for methyl 3-hydroxybenzoate. $^1$H NMR (500 MHz, DMSO-d$_6$) δ ppm 8.36 (m, 1H), 7.42 (m, 4H), 7.16 (m, 2H), 6.95 (m, 1H), 4.79–5.07 (m, 1H), 4.16 (m, 2H), 1.73–2.10 (m, 4H), 1.41 (m, 3H); MS (DCI/NH$_3$) m/z 392 [M+H]$^+$.

Example 163

8-(4-(3-isopropyl-5-methylphenoxy)-1-methylbutoxy)quinolin-2-amine

The title compound was prepared according to the procedure described in Example 92 substituting 3-isopropyl-5-methylphenol for methyl 3-hydroxybenzoate. $^1$H NMR (500 MHz, DMSO-d$_6$) δ ppm 8.36 (m, 1H), 7.45 (m, 3H), 7.12 (m, 1H), 6.59 (m, 1H), 6.48 (m, 2H), 4.72–4.93 (m, 1H), 3.83–4.05 (m, 2H), 2.75 (m, 1H), 2.21 (m, 3H), 1.75–2.05 (m, 4H), 1.37 (m, 3H), 1.12 (m, 6H); MS (DCI/NH$_3$) m/z 379 [M+H]$^+$.

Example 164

8-(4-(3,4-dichlorophenoxy)-1-methylbutoxy)quinolin-2-amine

The title compound was prepared according to the procedure described in Example 92 substituting 3,4-dichlorophenol for methyl 3-hydroxybenzoate. $^1$H NMR (500 MHz, DMSO-d$_6$) δ ppm 8.37 (m, 1H), 7.44 (m, 3H), 7.11 (m, 2H), 6.88 (m, 2H), 4.86 (m, 1H), 4.10 (m, 2H), 1.71–2.03 (m, 4H), 1.40 (m, 3H); MS (DCI/NH$_3$) m/z 392 [M+H]$^+$.

Example 165

N-methyl-8-(1,3,3-trimethylbutoxy)quinolin-2-amine

Example 165A 8-(1,3,3-trimethylbutoxy)quinoline

A 250 mL round bottom flask equipped with a pressure equalizing dropping funnel, stirring bar and N$_2$ outlet was charged with 4.00 g (27.6 mmol) of 8-hydroxyquinoline, 21.7 g (3 equiv) of PPh$_3$ and 80 mL of anhydr. THF. After stirring for 5 min, 4.91 mL (1.25 equiv) of 4,4-dimethyl-2-pentanol was added. The reaction mixture was then cooled in an ice bath and a solution of 9.52 g (1.5 equiv) of DBAD in 50 mL of anhydr. THF was added dropwise over 30 minutes. The reaction was allowed to slowly warm to room temperature, and stirring was maintained for an additional 6 h. Then, an additional 2.46 mL (0.62 equiv) of the alcohol was added, the reaction mixture was cooled in an ice bath and a solution of 4.76 g (0.75 equiv) of DBAD in 25 mL of anhydr. THF was added dropwise over 15 minutes. The reaction was allowed to slowly warm to room temperature, and stirring was maintained for an additional 12 h. An additional 10.9 g (1.5 equiv) of PPh$_3$ was added, followed by 2.46 mL (0.62 equiv) of the alcohol. The reaction mixture was cooled in an ice bath and a solution of 4.76 g (0.75 equiv) of DBAD in 25 mL of anhydr. THF was added dropwise over 15 minutes. The reaction was allowed to slowly warm to room temperature, and stirring was maintained for an additional 6 h. The reaction mixture was then evaporated in vacuo and the resulting residue dissolved in 150 mL of EtOAc. The solution was washed with 2 N HCl (3×400 mL). The aqueous layers were combined and basified with 10 N NaOH to pH 14. The resulting solution was extracted with EtOAc (3×150 mL), the organic layers were combined, dried over anhydr. Na$_2$SO$_4$ and evaporated in vacuo. The crude material was purified by silica gel column chromatography (10% EtOAc/hexanes+2% TEA) to afford the title compound. $^1$H NMR (300 MHz, CDCl$_3$) δ ppm 8.95 (dd, 1H), 8.10 (dd, 1H), 7.40 (m, 3H), 7.09 (br d, 1H), 4.79 (m, 1H), 2.20 (dd, 1H), 1.57 (m, 1H), 1.46 (d, 3H), 0.98 (s, 9H); MS (DCI/NH$_3$) m/z 244 [M+H]$^+$.

Example 165B 2-chloro-8-(1,3,3-trimethylbutoxy)quinoline

To a 100 mL round bottom flask charged with 2 mL of CH$_2$Cl$_2$, 0.500 g (2.07 mmol) of 8-(1,3,3-trimethylbutoxy) quinoline was slowly added with gentle heating in order to dissolve the material. To this was added 1.8 equiv m-CPBA (50–70% by weight) in three portions. After stirring for 30 min, the dense solution became a brown solid. The solid was dissolved in 25 mL EtOAc and the resulting solution was washed with 10% aqueous NaHSO$_3$, saturated aqueous NaHCO$_3$, and the organic layer evaporated in vacuo. After co-evaporation with toluene, the residue was dissolved in POCl$_3$ (5 mL) and the flask fitted with a reflux condenser. The reaction flask was then placed in an oil bath that had been preheated to 95° C. for 15 min. After cooling to room temperature, the solution was concentrated down to a red oil, which was then dissolved in CH$_2$Cl$_2$ and washed with saturated aqueous NaHCO$_3$ until the aqueous layers became basic. The organic layer was evaporated in vacuo and the residue was purified by silica gel column chromatography (EtOAc/hexanes) to afford the title compound. $^1$H NMR (300 MHz, DMSO-d$_6$) δ ppm 8.37 (d, 1H), 7.55 (m, 3H), 7.34 (m, 1H), 4.70–4.93 (m, 1H), 1.90 (dd, 1H), 1.53 (dd, 1H), 1.30 (d, 3H), 0.94 (s, 9H); MS (DCI/NH$_3$) m/z 277 [M+H]$^+$.

Example 165C

N-methyl-8-(1,3,3-trimethylbutoxy)quinolin-2-amine

A 7.5 mL conical microwave vessel (Personal Chemistry) equipped with a septum cap and a magnetic stirring bar was charged with 0.25 g (0.90 mmol) of 2-Chloro-8-(1,3,3-trimethylbutoxy)quinoline, NEt$_3$ (1.26 mL) and NMP (1.26 mL). The resulting suspension was irradiated in Personal Chemistry Smith Synthesizer (220° C. for 25 min; 300 W). Upon cooling, the residue was dissolved in a 3:1 hexanes/CH$_2$Cl$_2$ mixture (10 mL) and washed with H$_2$O. The organic layer was evaporated in vacuo and the residue was purified by silica gel column chromatography (5–15% MeOH/CH$_2$Cl$_2$) to afford the title compound. $^1$H NMR (500 MHz, DMSO-d$_6$) δ ppm 6.67–7.79 (m, 5H), 4.87 (m, 1H), 3.11 (m, 3H), 2.03 (m, 1H), 1.56 (m, 1H), 1.30 (m, 3H), 0.89 (m, 9H); MS (DCI/NH$_3$) m/z 273 [M+H]$^+$.

Example 166

N-propyl-8-(1,3,3-trimethylbutoxy)quinolin-2-amine

To a 4 mL scintillation vial was added a stir bar and the title compound from Example 16 (15.0 mg, 0.058 mmol). To this was added 0.42 mL of a 1:1 MeOH/ClCH$_2$CH$_2$Cl mixture followed by MP-cyanoborohydride resin (84 mg, 3.7 equiv Argonaut Technologies, Inc.) and 40 μL (10 equiv) of propionaldehyde. The reaction vessel was placed in an oil bath that had been preheated to 80° C. and the contents were allowed to stir overnight. Upon cooling to room temperature, the suspension was filtered and the filtrate was evaporated in vacuo. The crude material was purified by reverse phase HPLC to afford the title compound. $^1$H NMR (500 MHz, CDCl$_3$) δ ppm 8.06 (d, 1H), 7.30 (m, 1H), 7.17 (m, 2H), 6.90 (d, 1H), 4.54–4.81 (m, 1H), 3.38 (m, 2H), 2.38 (m, 1H), 1.80 (m, 1H), 1.50 (m, 2H), 1.39 (d, 3H), 1.03 (t, 3H), 0.96 (s, 9H); MS (DCI/NH$_3$) m/z 301 [M+H]$^+$.

Example 167

8-(((1R)-1,3,3-trimethylbutyl)oxy)quinolin-2-amine

Example 168

8-(((1S)-1,3,3-trimethylbutyl)oxy)quinolin-2-amine 100 mg of the title compound from Example 16 (3.88 mmol) were dissolved in 100 mL EtOH, loaded on a preparative column with chiral stationary phase (Chiralcel OD; 4.6×250 mm, flow=1.0 mL/min, detection: UV210 nm), and eluted with hexanes/EtOH. The two enantiomeric compounds were collected at 7.2 min and 12.8 min, respectively (dextrorotatory, assumed R; levorotatory, assumed S). The solvents were evaporated to afford the title products.

Example 167 {α}$_D^{20}$=+107°. $^1$H NMR (300 MHz, DMSO-d$_6$) δ ppm 7.83 (m, 1H), 7.16 (m, 1H), 7.03 (m, 2H), 6.76 (m, 1H), 6.18–6.38 (m, 2H), 4.72 (m, 1H), 1.85 (m, 1H), 1.47 (m, 1H), 1.24 (m, 3H), 0.84–1.04 (m, 9H); MS (DCI/NH$_3$) m/z 259 [M+H]$^+$.

Example 168 {α}$_D^{20}$=−111°. $^1$H NMR (300 MHz, DMSO-d$_6$) δ ppm 7.83 (m, 1H), 7.16 (m, 1H), 7.03 (m, 2H), 6.76 (m, 1H), 6.18–6.38 (m, 2H), 4.72 (m, 1H), 1.85 (m, 1H), 1.47 (m, 1H), 1.24 (m, 3H), 0.84–1.04 (m, 9H); MS (DCI/NH$_3$) m/z 259 [M+H]$^+$.

Example 169

N-((5-(2-(trifluoromethyl)phenyl)-2-furyl)methyl)-8-(1,3,3-trimethylbutoxy)quinolin-2-amine The title compound was prepared according to the procedure described in Example 166 substituting 5-(2-(trifluoromethyl)phenyl)-2-furaldehyde for propionaldehyde. $^1$H NMR (300 MHz, DMSO-d$_6$) δ ppm 7.68–7.94 (m, 5H), 7.42–7.66 (m, 4H), 6.67–6.89 (m, 2H), 4.79–5.05 (m, 3H), 1.96 (m, 1H), 1.56 (m, 1H), 1.31 (m, 3H), 0.92 (m, 9H); MS (DCI/NH$_3$) m/z 483 [M+H]$^+$.

Example 170

N-((5-(2-nitrophenyl)-2-furyl)methyl)-8-(1,3,3-trimethylbutoxy)quinolin-2-amine

The title compound was prepared according to the procedure described in Example 166 substituting 5-(2-nitrophenyl)-2-furaldehyde for propionaldehyde. $^1$H NMR (300 MHz, DMSO-d$_6$) δ ppm 7.83 (m, 2H), 7.71 (m, 2H), 7.40–7.63 (m, 5H), 6.95 (m, 1H), 6.70 (m, 1H), 4.74–5.02 (m, 3H), 1.99 (m, 1H), 1.58 (m, 1H), 1.31 (m, 3H), 0.76–0.99 (m, 9H); MS (DCI/NH$_3$) m/z 460 [M+H]$^+$.

Example 171

N-((5-(2-chlorophenyl)-2-furyl)methyl)-8-(1,3,3-trimethylbutoxy)quinolin-2-amine The title compound was prepared according to the procedure described in Example 166 substituting 5-(2-chlorophenyl)-2-furaldehyde for propionaldehyde. $^1$H NMR (500 MHz, CHCl$_3$) δ ppm 8.11 (m, 1H), 7.78 (m, 1H), 7.41 (m, 1H), 7.33 (m, 2H), 7.19 (m, 4H), 7.04 (m, 1H), 6.48 (m, 1H), 4.59–4.80 (m, 3H), 2.39 (m, 1H), 1.50 (m, 1H), 1.37 (m, 3H), 0.96 (m, 9H); MS (DCI/NH$_3$) m/z 407 [M+H]$^+$.

Example 172

8-hexylquinolin-2-amine

Example 172A 8-trifluoromethylsulfonylquinoline-2-amine

To an oven-dried 500 mL round bottom flask was added of 2-amino-8-hydroxyquinoline (5.04 g, 31.5 mmol). The system was evacuated and purged with N$_2$ three times, then charged with THF (70.0 mL) and pyridine (23.0 mL, 8 equiv). The solution was cooled to −30° C. in an isopropyl alcohol/dry ice bath, and triflic anhydride (14.9 mL, 2.8 equiv) was added dropwise over 50 min. The reaction mixture was allowed to warm to room temperature under N$_2$. After 2 h, the crude mixture was filtered through a pad of Celite, which was subsequently washed with THF (100 mL). The resulting solution was concentrated and the residue was dissolved in EtOAc (100 mL). This solution was washed with 1 M ammonium chloride (4×100 mL), saturated aqueous NaHCO$_3$, (4×100 mL), and brine (2×100 mL). The organic phase was concentrated, and the residue was purified by flash chromatography (20% EtOAc/hexane) to afford the title compound. MS (DCI/NH$_3$) m/z 293 [M]$^+$, 160.

Example 172

8-hexylquinolin-2-amine

A solution of 2-amino-8-trifluoromethanesulfonylquinoline (50.0 mg, 0.171 mmol) in THF (1.0 mL) was degassed by bubbling N$_2$ through the solution under vacuum for 5 min. The solution was added to a glass screw-top tube containing Pd(dppf)$_2$Cl$_2$.CH$_2$Cl$_2$ (13.9 mg, 0.1 equiv). Argon was then bubbled through the mixture for 1 minute, and 1-hexylzinc bromide (1.0 mL, 1 M in THF) was added. The tube was quickly sealed and placed in a heater/shaker at 65° C. for 20 h. The reaction mixture was cooled to room temperature, filtered through a 0.45 μm filter, and concentrated. The residue was dissolved in 1:1 DMSO/MeOH, filtered through a 0.45 μm filter, and purified by reverse phase HPLC. $^1$H NMR (300 MHz, DMSO-d$_6$) δ 9.10 (br s, 1H), 8.36 (br s, 1H), 8.23 (br s, 1H), 7.77 (d, 1H), 7.63 (d, 1H), 7.43 (br s, 1H), 7.10 (d, 1H), 1.41–1.25 (m, 10H), 0.86 (t, 3H); MS (DCI/NH$_3$) m/z 228 [M]$^+$.

Example 173

8-(1-methylpentyl)quinolin-2-amine

The title compound was prepared according to the procedure described in Example 172 substituting 1-methylpentylzinc bromide for 1-hexylzinc bromide. $^1$H NMR (300 MHz, DMSO-d$_6$) δ 9.20 (br s, 1H), 8.45 (br s, 1H), 8.37 (d, 1H), 7.77 (d, 1H), 7.70 (d, 1H), 7.49 (br s, 1H), 7.12 (d, 1H), 1.71–1.67 (m, 3H), 1.28–1.14 (m, 4H), 0.82 (d, 3H), 0.74 (t, 3H); MS (DCI/NH$_3$) m/z 228 [M]$^+$.

Example 174

8-(1-ethylbutyl)quinolin-2-amine

The title compound was prepared according to the procedure described in Example 172 substituting 1-ethylbutylzinc bromide for 1-hexylzinc bromide. $^1$H NMR (300 MHz, DMSO-d$_6$) δ 9.20 (br s, 1H), 8.40 (br s, 1H), 8.37 (br s, 1H), 7.77 (d, 1H), 7.69 (d, 1H), 7.49 (br s, 1H), 7.12 (d, 1H), 1.79–1.62 (m, 3H), 1.28–1.18 (m, 4H), 0.81 (t, 3H), 0.74 (t, 3H); MS (DCI/NH$_3$) m/z 228 [M]$^+$.

Example 175

8-(1-ethylpentyl)quinolin-2-amine

The title compound was prepared according to the procedure described in Example 172 substituting 1-ethylpentylzinc bromide for 1-hexylzinc bromide. $^1$H NMR (300 MHz, DMSO-d$_6$) δ 9.15 (br s, 1H), 8.37 (br s, 1H), 8.20 (br s, 1H), 7.77 (d, 1H), 7.67 (d, 1H), 7.48 (br s, 1H), 7.08 (d, 1H), 1.81–1.62 (m, 3H), 1.21–1.15 (m, 6H), 0.79 (t, 3H), 0.73 (t, 3H); MS (DCI/NH$_3$) m/z 242 [M]$^+$.

Example 176

8-cyclohexylquinolin-2-amine

The title compound was prepared according to the procedure described in Example 172 substituting cyclohexylzinc bromide for 1-hexylzinc bromide. $^1$H NMR (300 MHz, DMSO-d$_6$) δ 9.10 (br s, 1H), 8.36 (br s, 1H), 8.23 (br s, 1H), 7.75 (d, 1H), 7.67 (br s, 1H), 7.45 (d, 1H), 7.09 (br s, 1H), 1.80 (m, 1H), 1.60–1.48 (m, 8H), 1.35–1.28 (m, 2H); MS (DCI/NH$_3$) m/z 226 [M]$^+$.

Example 177

8-((5-((2-aminoquinolin-8-yl)oxy)pentyl)oxy)-quinolin-2-amine

A 20 mL scintillation vial with a septum cap was charged with PS-PPh$_3$ resin (Aldrich Chemical Co., Inc, 132 mg, 4.2 equiv) 2-amino-8-hydroxyquinoline (154 mg, 10 equiv) and DBAD (70 mg, 3.2 equiv) and purged by passing a stream of N$_2$ for 45 seconds. Anhydr. THF (2.0 mL) was added and contents of the vial were agitated for 5 min. Then, a solution of 1,5-pentanediol (10 mg, 0.094 mmol) in anhydr. THF (1 mL) was added to the vial and the resulting suspension was agitated at room temperature for 8 h. The suspension was then filtered, and the resin washed with DMA (6×3.0 mL). The filtrate and washings were combined and evaporated in vacuo. The resulting oily residue was dissolved in 50 mL of EtOAc and washed with aqueous NH$_3$. The solution was then evaporated in vacuo and the residue was dissolved in 3.0 mL of a 1:1 mixture of DMSO/MeOH and purified by preparative reverse-phase HPLC. $^1$H NMR (500 MHz, CDCl$_3$) δ ppm 7.95 (d, 2H), 7.27 (m, 2H), 7.21 (m, 2H), 7.14 (d, 2H), 7.05 (m, 2H), 4.20 (m, 4H), 2.04 (m, 4H), 1.94 (m, 2H); MS (DCI/NH$_3$) m/z 389 [M+H]$^+$.

Example 178

8-(3-((2-aminoquinolin-8-yl)oxy)butoxy)quinolin-2-amine

The title compound was prepared according to the procedure described in Example 177 substituting 1,3-butanediol for 1,5-pentanediol. $^1$H NMR (500 MHz, DMSO-d$_6$) δ ppm 8.31 (m, 2H), 7.41 (m, 3H), 7.32 (m, 3H), 7.10 (m, 2H), 5.15 (m, 1H), 4.46 (m, 2H), 2.41 (m, 2H), 1.46 (m, 3H); MS (DCI/NH$_3$) m/z 375 [M+H]$^+$.

Example 179

8-(3-(2-aminoquinolin-8-yloxy)propoxy)quinolin-2-amine

A 20 mL scintillation vial with a septum cap was charged with PS-PPh$_3$ resin (Aldrich Chemical Co., Inc, 200 mg, 4 equiv) 2-amino-8-hydroxyquinoline (100 mg, 5 equiv) and purged by passing a stream of N$_2$ for 45 seconds. Anhydr. THF (3.0 mL) was added and contents of the vial were agitated for 3 min. Then, 1,3-propanediol (10 mg, 0.13 mmol) was added to the vial followed by DBAD (66 mg, 2 equiv) and the resulting suspension was agitated at room temperature for 15 min. Then additional DBAD (33 mg, 1 equiv) was added and the mixture was agitated for additional 15 min. The last addition of DBAD was repeated and the mixture was agitated for 6 h. The suspension was then filtered, and the resin washed with DMA (6×3.0 mL). The filtrate and washings were combined and evaporated in vacuo. The residue was dissolved in DMA (10 mL) and MP-TsOH resin (Argonaut Technologies, Inc., 4.5 g) was added. The resulting suspension was agitated at room temperature for 12 h. The supernatant was subsequently drained and the resin was washed with DMA (10 mL), MeOH (10 mL) and DMA (10 mL) and MeOH (10 mL). The washed resin was treated with a mixture of 2 N NH₃ in MeOH (15 mL) and DMA (5 mL) at room temperature for 1 h. The solution was drained and the basic wash was repeated two. more times. The filtered solutions were combined. The resin was washed with MeOH (10 mL), DMA (10 mL), MeOH (10 mL), DMA (10 mL) and MeOH (10 mL). The washes were combined with the previously collected solutions and evaporated in vacuo. The residue was dissolved in 1.5 mL of a 1:1 mixture of DMSO/MeOH and purified by preparative reverse-phase HPLC. $^1$H NMR (500 MHz, MeOH-d₄) δ ppm 8.00 (d, 2H), 7.26 (m, 2H), 7.18 (m, 4H), 6.89 (d, 2H), 4.46 (m, 4H), 2.53 (m, 2H); MS (DCI/NH₃) m/z 361 [M+H]⁺.

Example 180

8-((2E)-but-2-enyloxy)quinolin-2-amine

A 250 mL round bottom flask was charged with 2.00 g (12.5 mmol) of 2-amino-8-hydroxyquinoline, 3.46 g (25.0 mmol), of K₂CO₃ and 63 mL of anhydr ethanol. Following the dissolution of 2-amino-8-hydroxyquinoline, 1.51 mL of 3-chloro-1-butene (15.0 mmol) was added in one portion, and the mixture was heated to 65° C. in an oil bath. After 48 h, the solvent was evaporated and the residue dissolved in EtOAc and washed with H₂O. The combined aqueous layers were back-extracted with EtOAc. The organic layers were then pooled, dried, and filtered. The residue was then purified by column chromatography (SiO₂; EtOAc/hexanes with 0.1% Et₃N). The resultant material was then re-crystallized from Et₂O to afford the title compound. $^1$H NMR (300 MHz, DMSO-d₆) δ ppm 7.82 (m, 1H), 7.16 (m, 1H), 7.00 (m, 2H), 6.73 (m, 1H), 6.39 (m, 2H), 5.67–5.98 (m, 2H), 4.44–4.67 (m, 2H), 1.74 (m, 3H); MS (DCI/NH₃) m/z 215 [M+H]⁺.

Example 181

3-methyl-8-(1,3,3-trimethylbutoxy)quinolin-2-amine

Example 181A 2,2-dimethyl-N-(8-(1,3,3-trimethylbutoxy)quinolin-2-yl)propanamide To a 20 mL scintillation vial was added a stir bar, the title compound from Example 16 (161 mg, 0.624 mmol) and 1.5 mL of THF. To the resultant solution was added Et₃N (0.174 mL, 2 equiv) and trimethylacetylchloride (93 μL, 1.2 equiv). The solution was allowed to stir overnight, after which time the mixture placed directly on a silica column and eluted with EtOAc/hexanes to afford the title compound. $^1$H NMR (300 MHz, DMSO-d₆) δ ppm 8.27 (m, 1H), 7.96–8.18 (m, 1H), 7.42 (m, 2H), 7.21 (m, 1H), 4.64–4.90 (m, 1H), 1.90 (m, 1H), 1.53 (m, 1H), 1.31 (m, 12H), 0.83–1.05 (m, 9H); MS (DCI/NH₃) m/z 343 [M+H]⁺.

Example 181B 2,2-dimethyl-N-(3-methyl-8-(1,3,3-trimethylbutoxy) quinolin-2-yl)propanamide A 50 mL three-neck flask with a stir bar was charged with the title compound from Example 181A (270 mg, 0.790 mmol) and 3 mL of THF. The flask was cooled to 0° C. in an ice bath and 0.9 mL of a 2.5 M solution of n-BuLi in THF was added slowly via syringe. The resultant solution was allowed to stir at 0° C. for 4 h, and then cooled to −78° C. After 5 min at this temperature iodomethane (74.0 μL, 1.5 equiv.) was added slowly and the mixture was allowed to slowly warm to room temperature. After stirring overnight, the reaction was quenched with water and extracted with Et₂O. The ethereal layers were combined and washed with saturated aqueous NH₄Cl, dried, and evaporated. The residue was then purified by silica gel chromatography EtOAc/hexanes) to afford the title compound. $^1$H NMR (300 MHz, DMSO-d₆) δ ppm 8.08 (m, 1H), 7.44 (m, 2H), 7.17 (m, 1H), 4.69–5.03 (m, 1H), 2.27 (m, 3H), 1.73–1.95 (m, 1H), 1.44–1.65 (m, 1H), 1.29 (m, 3H), 1.27 (m, 9H), 0.95 (m, 9H); MS (DCI/NH₃) m/z 357 [M+H]⁺.

Example 181C 3-methyl-8-(1,3,3-trimethylbutoxy)quinolin-2-amine

A 20 mL glass tube was charged with the title compound from Example 181B(57.0 mg, 0.160 mmol), 1.5 mL of MeOH and sodium methoxide (26.0 mg, 3 equiv.). The tube was sealed and heated to 70° C. in an oil bath for 12 h. The reaction mixture was then allowed to cool to room temperature and was then quenched with saturated aqueous NH₄Cl. The mixture was diluted with Et₂O and partitioned, the aqueous layer was washed with Et₂O. The ethereal layers were combined, dried, and filtered. Evaporation of the solvent afforded a residue, which was purified by silica gel chromatography (MeOH/CH₂Cl₂) to afford the title product. $^1$H NMR (300 MHz, DMSO-d₆) δ ppm 8.11 (s, 1H), 7.35–7.49 (m, 2H), 7.16 (m, 1H), 4.86 (m, 1H), 2.26 (s, 3H), 1.86 (dd, 1H), 1.52 (dd, 1H), 1.27 (d, 3H), 0.97 (m, 9H); MS (DCI/NH₃) m/z 273 [M+H]⁺.

Example 182

2-(((8-(1,3,3-trimethylbutoxy)quinolin-2-yl)amino) carbonyl)benzyl benzoate

To a 20 mL scintillation vial was added a stir bar, the title compound from Example 16 (100 mg, 0.388 mmol) and anhydr. THF (1.3 mL). To the resultant solution was added of Et₃N (0.12 mL, 2.2 equiv), DMAP (5.0 mg, 1.06 equiv) and of 2-(benzoyloxymethyl)benzoyl chloride (116 mg, 1.1 equiv). The solution was stirred overnight, after which time the mixture was placed directly on a silica gel column and eluted with EtOAc/hexanes to afford the title compound. $^1$H NMR (300 MHz, DMSO-d₆) δ ppm 8.23 (m, 1H), 8.16 (m, 1H), 7.92 (m, 2H), 7.72 (m, 1H), 7.55 (m, 4H), 7.38 (m, 4H), 7.24 (m, 1H), 5.51 (s, 2H), 4.82 (m, 1H), 1.88 (dd, 1H), 1.49 (dd, 1H), 1.34 (d, 3H), 0.92 (s, 9H); MS (DCI/NH₃) m/z 497 [M+H]⁺.

Example 183

N-(3-((2-aminoquinolin-8-yl)oxy)propyl)-8-(1,3,3-trimethylbutoxy)quinolin-2-amine

Example 183A 3-((8-(1,3,3-trimethylbutoxy)quinolin-2-yl)amino) propan-1-ol

A 7.5 mL conical microwave vessel (Personal Chemistry) equipped with a septum cap and a magnetic stirring bar was charged with the title compound from Example 165B (150 mg, 0.540 mmol) and 3-aminopropanol (0.825 mL, 20 equiv). The resulting solution was irradiated in Personal Chemistry Smith Synthesizer (220° C. for 25 min; 300 W). After cooling to room temperature, the contents were directly loaded on a silica gel column and eluted with EtOAc/hexanes to afford the title compound. $^1$H NMR (300 MHz, DMSO-$d_6$) δ ppm 7.77 (m, 1H), 7.15 (m, 1H), 7.02 (m, 3H), 6.70 (m, 1H), 5.03 (m, 1H), 4.64–4.86 (m, 1H), 3.62 (m, 1H), 3.43 (m, 3H), 1.91 (m, 1H), 1.55–1.78 (m, 2H), 1.44 (m, 1H), 1.23 (m, 3H), 0.96 (m, 9H); MS (DCI/NH$_3$) m/z 317 [M+H]$^+$.

Example 183B

N-(3-((2-aminoquinolin-8-yl)oxy)propyl)-8-(1,3,3-trimethylbutoxy)quinolin-2-amine A 20 mL scintillation vial with a septum cap was charged with PS-PPh$_3$ resin (Aldrich Chemical Co., Inc, 46 mg, 2.2 equiv), the title compound from Example 183A (10 mg, 0.03 mmol) and DBAD (12 mg, 1.6 equiv) and purged by passing a stream of N$_2$ for 45 seconds. Anhydr. THF (3 mL) was added and the contents of the vial were shaken for 5 min. Then, a solution of 2-amino-8-hydroxyquinoline (11 mg, 0.07 mmol) in anhydr. THF (1 mL) was added and the resulting suspension was shaken at room temperature for 6 h. The suspension was filtered, and the resin washed with THF (three times 3.0 mL). The filtrate and washings were combined and evaporated in vacuo. The residue was then treated with 6.0 mL of 4 M HCl in dioxane at room temperature for 12 h. The resulting solution was evaporated in vacuo. The residue was dissolved in 1.5 mL of a 1:1 mixture of DMSO/MeOH and purified by preparative reverse-phase HPLC. $^1$H NMR (500 MHz, CDCl$_3$) δ ppm 8.04 (br d, 1H), 7.92 (br d, 1H), 7.29 (m, 2H), 7.16 (m, 4H), 7.01 (m, 2H), 4.71 (m, 1H), 4.35 (m, 2H), 3.82–4.03 (m, 2H), 2.46 (m, 2H), 2.29 (m, 1H), 1.51 (m, 1H), 1.37 (d, 3H), 0.94 (s, 9H); MS (DCI/NH$_3$) m/z 459 [M+H]$^+$.

Example 184

8-(4-(2-chloro-4-methylphenoxy)-1-methylbutoxy)quinolin-2-amine

The title compound was prepared according to the procedure described in Example 92 substituting 2-chloro-4-methylphenol for methyl 3-hydroxybenzoate. $^1$H NMR (500 MHz, CDCl$_3$) δ ppm 7.93 (d, 1H), 7.29 (t, 1H), 7.18 (m, 1H), 7.15 (m, 1H), 7.09 (m, 1H), 6.99 (d, 1H), 6.94 (m, 1H), 6.79 (d, 1H), 4.77 (m, 1H), 4.10 (m, 1H), 4.03 (m, 1H), 2.22 (s, 3H), 2.20 (m, 1H), 2.03 (m, 3H), 1.47 (d, 3H); MS (DCI/NH$_3$) m/z 371 [M+H]$^+$.

Example 185

8-(4-(2-(benzyloxy)phenoxy)-1-methylbutoxy)quinolin-2-amine

The title compound was prepared according to the procedure described in Example 92 substituting 2-(benzyloxy)phenol for methyl 3-hydroxybenzoate. $^1$H NMR (500 MHz, CDCl$_3$) δ ppm 7.91 (d, 1H), 7.40 (m, 2H), 7.31 (m, 2H), 7.25 (m, 1H), 7.20 (t, 1H), 7.14 (dd, 1H), 7.08 (m, 1H), 6.99 (d, 1H), 6.90 (m, 3H), 6.83 (m, 1H), 5.06 (d, 2H), 4.73 (m, 1H), 4.09 (m, 2H), 2.20 (m, 1H), 2.01 (m, 3H), 1.42 (d, 3H); MS (DCI/NH$_3$) m/z 429 [M+H]$^+$.

Example 188

8-(((3S)-1-(1,3-benzodioxol-5-ylmethyl)pyrrolidin-3-yl)oxy)quinolin-2-amine

A 4 dram scintillation vial was charged with 135 mg (0.509 mmol) of Example 195, 1,3-benzodioxole-5-carbaldehyde (92.0 mg, 0.613 mmol), and macroporous sodium cyanoborohydride resin (400 mg, 2.55 mmol/g, 2 equiv). A solution of 1:1 MeOH/dichloroethane with 1% AcOH was added (3 mL) and the reaction vessel shaken for approximately 16 hours. After this time the resin was filtered off and the solvents evaporated. The residue was dissolved in 1:1 MeOH/DMSO and purified on a reverse-phase HPLC column to afford the title compound. $^1$H NMR (300 MHz, DMSO-$d_6$, 90° C.) δ ppm 7.81 (m, 1H), 7.17 (m, 1H), 7.02 (m, 1H), 6.86 (m, 3H), 6.76 (m, 2H), 5.97 (m, 2H), 5.00 (m, 1H), 3.56 (m, 2H), 2.88 (m, 1H), 2.72 (m, 2H), 2.31 (m, 2H), 1.87 (m, 1H); MS (DCI/NH$_3$) m/z 364 [M+H]$^+$.

Example 189

8-(((3S)-1-(2-fluorobenzyl)pyrrolidin-3-yl)oxy)quinolin-2-amine

The title compound was prepared according to the procedure described in Example 188 substituting 2-flourobenzaldehyde for 1,3-benzodioxole-5-carbaldehyde. $^1$H NMR (300 MHz, DMSO-$d_6$, 90° C.) δ ppm 8.39 (m, 1H), 7.58 (m, 2H), 7.43 (m, 3H), 7.29 (m, 2H), 7.13 (m, 1H), 5.28–5.52 (m, 1H), 4.34–4.67 (m, 2H), 3.80 (m, 1H), 3.17 (m, 2H), 2.77 (m, 1H), 2.21–2.45 (m, 2H); MS (DCI/NH$_3$) m/z 338 [M+H]$^+$.

Example 190

8-(((3S)-1-(1,1'-biphenyl-4-ylmethyl)pyrrolidin-3-yl)oxy)quinolin-2-amine

The title compound was prepared according to the procedure described in Example 188 substituting 4-biphenylcarboxaldehyde for 1,3-benzodioxole-5-carbaldehyde. $^1$H NMR (300 MHz, DMSO-$d_6$, 90° C.) δ ppm 8.29 (m, 1H), 7.70 (m, 4H), 7.59 (m, 2H), 7.49 (m, 3H), 7.37 (m, 3H), 7.12 (m, 1H), 5.40 (m, 1H), 4.43 (m, 2H), 3.79 (m, 2H), 3.63 (m, 1H), 2.58 (m, 1H), 2.37 (m, 2H); MS (DCI/NH$_3$) m/z 396 [M+H]$^+$.

Example 191

8-(((3S)-1-((3-methyl-1-benzothien-2-yl)methyl)pyrrolidin-3-yl)oxy)quinolin-2-amine The title compound was prepared according to the procedure described in Example 188 substituting 3-methylbenzo(B)thiophene-2-carboxaldehyde for 1,3-benzodioxole-5-carbaldehyde. $^1$H NMR (500 MHz, DMSO-$d_6$, 90° C.) δ ppm 8.22–8.44 (m, 1H), 7.77 (m, 1H), 7.40 (m, 5H), 7.11 (m, 2H), 5.28–5.59 (m, 1H), 4.61–5.00 (m, 2H), 3.77–4.10 (m, 1H), 3.21 (m, 2H), 2.69–2.96 (m, 1H), 2.23–2.48 (m, 5H); MS (DCI/NH$_3$) m/z 390 [M+H]$^+$.

Example 193

8-(((3S)-1-((2,2-dimethyl-3,4-dihydro-2H-chromen-6-yl)methyl)pyrrolidin-3-yl)oxy)quinolin-2-amine The title compound was prepared according to the procedure described in Example 188 substituting 2,2-dimethylchromane-6-carboxaldehyde for 1,3-benzodioxole-5-carbaldehyde. $^1$H NMR (300 MHz, DMSO-d$_6$, 90° C.) δ ppm 8.31 (m, 1H), 7.51 (m, 1H), 7.37 (m, 2H), 7.16 (m, 3H), 6.70 (m, 1H), 5.37 (m, 1H), 4.34 (m, 2H), 3.60 (m, 3H), 2.72 (m, 2H), 2.55 (m, 1H), 2.40 (m, 1H), 1.58–1.82 (m, 2H), 1.24 (m, 7H); MS (DCI/NH$_3$) m/z 404 [M+H]$^+$.

Example 194 tert-butyl 8-((3S)-pyrrolidin-3-yloxy)quinolin-2-ylcarbamate

The title compound was prepared according to the procedure described in Example 92 substituting (3S)-hydroxypyrrolidine-1-carboxylic acid-tert-butyl ester for methyl 3-hydroxybenzoate. $^1$H NMR (500 MHz, CDCl$_3$) δ ppm 7.87 (m, 1H), 7.22 (m, 1H), 7.16 (m, 1H), 6.96 (m, 1H), 5.31 (s, 1H), 5.10 (m, 1H), 3.51–3.89 (m, 4H), 2.30–2.56 (m, 1H), 2.18 (m, 1H), 1.47 (s, 9H); MS (DCI/NH$_3$) m/z 330 [M+H]$^+$.

Example 195

8-((3S)-pyrrolidin-3-yloxy)quinolin-2-amine

To a 4 dram vial containing Example 194 (300 mg, 0.608 mmol) was added 3 mL of a 4 M solution of HCl in dioxane. The mixture was allowed to sit for 60 min and then the solvent was evaporated to afford the HCl salt of the title compound. $^1$H NMR (300 MHz, d$_4$-MeOH) δ ppm 8.31 (m, 1H), 7.46 (m, 3H), 7.07 (m, 1H), 5.55 (m, 1H), 3.82 (m, 1H), 3.44–3.71 (m, 3H), 2.41 (m, 2H); MS (DCI/NH$_3$) m/z 230 [M+H]$^+$.

Example 196

8-(((3S)-1-(4-tert-butylbenzyl)pyrrolidin-3-yl)oxy)quinolin-2-amine

The title compound was prepared according to the procedure described in Example 188 substituting 4-tert-butylbenzaldehyde for 1,3-benzodioxole-5-carbaldehyde. $^1$H NMR (300 MHz, DMSO-d$_6$, 90° C.) δ ppm 8.31 (m, 1H), 7.50 (m, 1H), 7.43 (m, 4H), 7.37 (m, 2H), 7.12 (m, 1H), 5.38 (m, 1H), 3.54–3.84 (m, 3H), 3.38 (m, 1H), 2.55 (m, 1H), 2.36 (m, 1H), 1.27 (m, 9H); MS (DCI/NH$_3$) m/z 376 [M+H]$^+$.

Example 197

8-(((3S)-1-(2,3-dihydro-1,4-benzodioxin-6-ylmethyl)pyrrolidin-3-yl)oxy)quinolin-2-amine The title compound was prepared according to the procedure described in Example 188 substituting 1,4-benzodioxan-6-carboxaldehyde for 1,3-benzodioxole-5-carbaldehyde. $^1$H NMR (300 MHz, DMSO-d$_6$, 90° C.) δ ppm 8.29 (m, 1H), 7.50 (m, 1H), 7.36 (m, 2H), 7.13 (m, 1H), 7.02 (m, 1H), 6.94 (m, 1H), 6.85 (m, 1H), 5.34 (m, 1H), 4.25 (m, 6H), 3.48–3.75 (m, 4H), 2.54 (m, 1H), 2.36 (m, 1H); MS (DCI/NH$_3$) m/z 378 [M+H]$^+$.

Example 198

8-(((3S)-1-(2,3-difluorobenzyl)pyrrolidin-3-yl)oxy)quinolin-2-amine

The title compound was prepared according to the procedure described in Example 188 substituting 2,3-diflourobenzaldehyde for 1,3-benzodioxole-5-carbaldehyde. $^1$H NMR (300 MHz, DMSO-d$_6$, 90° C.) δ ppm 8.34 (m, 1H), 7.50 (m, 1H), 7.38 (m, 4H), 7.23 (m, 1H), 7.14 (m, 1H), 5.20–5.40 (m, 1H), 4.17–4.38 (m, 2H), 3.61 (m, 1H), 3.41 (m, 2H), 3.02–3.28 (m, 1H), 2.55 (m, 1H), 2.12–2.40 (m, 1H); MS (DCI/NH$_3$) m/z 356 [M+H]$^+$.

Example 199

8-(((3S)-1-(3-(trifluoromethyl)benzyl)pyrrolidin-3-yl)oxy)quinolin-2-amine

The title compound was prepared according to the procedure described in Example 188 substituting 3-(triflouromethyl)benzaldehyde for 1,3-benzodioxole-5-carbaldehyde. $^1$H NMR (300 MHz, DMSO-d$_6$, 90° C.) δ ppm 8.33 (m, 1H), 7.84 (m, 1H), 7.75 (m, 2H), 7.63 (m, 1H), 7.50 (m, 1H), 7.36 (m, 2H), 7.11 (m, 1H), 5.33 (m, 1H), 4.37 (m, 2H), 3.64 (m, 1H), 3.47 (m, 2H), 3.26 (m, 1H), 2.58 (m, 1H), 2.35 (m, 1H); MS (DCI/NH$_3$) m/z 388 [M+H]$^+$.

Example 200

8-(((3S)-1-((2,2-difluoro-1,3-benzodioxol-5-yl)methyl)pyrrolidin-3-yl)oxy)quinolin-2-amine The title compound was prepared according to the procedure described in Example 188 substituting 2,2-diflouro-1,3-benzodioxolo-5-carboxaldehyde for 1,3-benzodioxole-5-carbaldehyde. $^1$H NMR (300 MHz, MEOH) δ ppm 7.87 (m, 1H), 7.26 (m, 1H), 7.20 (m, 1H), 7.15 (m, 1H), 7.13 (m, 1H), 7.09 (m, 1H), 6.92 (m, 1H), 6.81 (m, 1H), 5.06 (m, 1H), 3.71 (m, 2H), 3.13 (m, 1H), 2.91 (m, 1H), 2.82 (m, 1H), 2.68 (m, 1H), 2.39 (m, 1H), 2.18 (m, 1H); MS (DCI/NH$_3$) m/z 364 [M+H]$^+$.

Example 201

8-(((3S)-1-(2,4-dimethylbenzyl)pyrrolidin-3-yl)oxy)quinolin-2-amine

The title compound was prepared according to the procedure described in Example 188 substituting 2,4-dimethylbenzaldehyde for 1,3-benzodioxole-5-carbaldehyde. $^1$H NMR (300 MHz, DMSO-d$_6$, 90° C.) δ ppm 8.30 (m, 1H), 7.49 (m, 1H), 7.33 (m, 3H), 7.06 (m, 3H), 5.20–5.42 (m, 1H), 4.16–4.38 (m, 2H), 3.44–3.75 (m, 5H), 2.55 (m, 1H), 2.34 (m, 3H), 2.24 (m, 3H); MS (DCI/NH$_3$) m/z 348 [M+H]$^+$.

Example 202

N-(2,3-dihydro-1,4-benzodioxin-6-ylmethyl)-8-(((3S)-1-(2,3-dihydro-1,4-benzodioxin-6-ylmethyl)pyrrolidin-3-yl)oxy)quinolin-2-amine The title compound was prepared according to the procedure described in Example 188 substituting 1,4-benzodioxan-6-carboxaldehyde for 1,3-benzodioxole-5-carbaldehyde. $^1$H NMR (300 MHz, DMSO-d$_6$, 90° C.) δ ppm 8.00 (m, 1H), 7.41 (m, 1H), 7.19 (m, 2H), 7.04 (m, 2H), 6.96 (m, 2H), 6.87 (m, 2), 6.77 (m, 1H), 5.39 (m, 1H), 4.57 (m, 2H), 4.34 (m, 2H), 4.21 (m, 10H), 3.38 (m, 2H), 2.13–2.44 (m, 2H); MS (DCI/NH$_3$) m/z 526 [M+H]$^+$.

Example 203

4-((3-((2-aminoquinolin-8-yl)oxy)propyl)amino)-6-methyl-2H-chromen-2-one

Example 203 A 6-methyl-4-(((trifluoromethyl)sulfonyl)methyl)-2H-chromen-2-one A 250 mL round bottom flask equipped with a magnetic stirring bar and a pressure equalizing dropping funnel was charged with 5.20 g (29.5 mmol) of 4-hydroxy-6-methyl-chromen-2-one. The flask was purged with nitrogen and a solution of NEt$_3$ (8.3 mL) in DCM (60 mL) was added. The resulting solution was cooled to −10° C. and trifluoromethanesulfonic anhydride (10.0 g; 1.2 eq) was added dropwise to the flask over 5 min. The resulting mixture was kept at −10° C. for 2 h then diluted with 130 mL of 1:1 mixture of ether/hexanes. The mixture was allowed to warm up to 0° C. and stirring was maintained for additional 10 min. The reaction mixture was then filtered through a short column of silica gel. Additional 100 mL of 1:1 mixture of ether hexanes and 50 mL of EtOAc were used to completely elute the product from the column. The volatiles were removed in vacuo to give 8.45 g (93%) of the title compound. $^1$H NMR (500 MHz, DMSO-d$_6$) δ ppm; MS (DCI/NH$_3$) m/z 309 [M+H]$^+$.

Example 203 B 4-((3-hydroxypropyl)amino)-6-methyl-2H-chromen-2-one

A 7.5 mL conical microwave reaction vessel (Personal Chemistry) was charged with the title compound from Example 203 A (0.030 g, 0.097 mol) and purged with N$_2$. Then a solution of 3-amino-propan-1-ol (0.075 mL, 10 eq.) in a mixture of acetonitrile (2 mL) and triethylamine (0.2 mL) was added. The resulting solution was irradiated in Personal Chemistry Smith Synthesizer (150° C. for 180 s; 300 W). The reaction mixture was then evaporated in vacuo. The resulting crude material was purified by silica gel column chromatography (ACN+2% DIEA) to afford the title compound. $^1$H NMR (500 MHz, DMSO-d$_6$) δ ppm 7.86 (m, 1H), 7.54 (m, 1H), 7.39 (m, 1H), 7.19 (m, 1H), 5.12 (s, 1H), 4.57 (m, 1H), 3.52 (m, 2H), 2.38 (s, 3H), 1.80 (m, 2H); MS (DCI/NH$_3$) m/z 234 [M+H]$^+$.

Example 203 C 4-((3-((2-aminoquinolin-8-yl)oxy)propyl)amino)-6-methyl-2H-chromen-2-one A 20 mL scintillation vial equipped with a septum cap was charged with PS-PPh$_3$ resin (Aldrich Chemical Co., Inc, 130 mg, 2.2 equiv), 2-amino-8-hydroxyquinoline (31 mg, 2 equiv) and DBAD (36 mg, 1.6 equiv) and purged by passing a stream of N$_2$ for 45 seconds. Anhydrous THF (2.0 mL) was added and contents of the vial were agitated for 5 min. Then, a solution of the title compound from Example 1 B (22 mg, 0.094 mmol) in anhydr. THF (1 mL) was added to the vial and the resulting suspension was agitated at room temperature for 16 h. The suspension was then filtered, and the resin washed with THF (3×3.0 mL). The filtrate and washings were combined and evaporated in vacuo. The residue was dissolved in 1.5 mL of a 1:1 mixture of DMSO/MeOH and purified by preparative reverse-phase HPLC. $^1$H NMR (500 MHz, acetone-d$_6$) δ ppm 8.36 (d, 1H), 7.82 (br s, 1H), 7.43 (m, 3H), 7.30 (m, 1H), 7.25 (d, 1H), 7.06 (d, 1H), 5.17 (s, 1H), 4.49 (m, 2H), 3.71 (m, 2H), 2.47 (m, 2H), 2.33 (s, 3H); MS (DCI/NH$_3$) m/z 376 [M+H]$^+$.

Example 204

4-[3-(2-amino-quinolin-8-yloxy)-propylamino]-6-chloro-chromen-2-one

Example 204 A

Trifluoromethanesulfonic acid 6-chloro-2-oxo-2H-chromen-yl ester

The title compound was prepared according to the procedure described in Example 203 A substituting 4-hydroxy-6-methyl-chromen-2-one for 4-hydroxy-6-chloro-chromen-2-one. $^1$H NMR (300 MHz, MeOD-d$_4$) δ 6.56 (s, 1H), 7.26 (s, 1H), 7.38 (d, 1H, d), 7.64 (d, 1H); MS (DCI/NH$_3$) m/z 329 [M+H]$^+$.

Example 204 B 6-chloro-4-((3-hydroxypropyl)amino)-2H-chromen-2-one

The title compound was prepared according to the procedure described in Example 203 B substituting trifluoromethanesulfonic acid 6-chloro-2-oxo-2H-chromen-yl ester for trifluoromethanesulfonic acid 6-methyl-2-oxo-2H-chromen-yl ester. $^1$H NMR (500 MHz, DMSO-d$_6$) δ ppm 8.22 (d, 1H), 7.64 (m, 2H), 7.36 (d, 1H), 5.19 (s, 1H), 4.56 (m, 1H), 3.52 (m, 2H), 1.79 (m, 2H); MS (DCI/NH$_3$) m/z 254 [M+H]$^+$.

Example 204 C

4-[3-(2-amino-quinolin-8-yloxy)-propylamino]-6-chloro-chromen-2-one

The title compound was prepared according to the procedure described in Example 203 C substituting 4-(3-hydroxy-propylamino)-6-chloro-chromen-2-one for 4-(3-hydroxy-propylamino)-6-methyl-chromen-2-one. $^1$H NMR (500 MHz, acetone-d$_6$) δ ppm 8.35 (br s, 1H), 8.08 (m, 1H), 7.49 (m, 1H), 7.41 (m, 3H), 7.25 (d, 1H), 7.18 (d, 1H), 5.23 (s, 1H), 4.49 (m, 2H), 3.72 (m, 2H), 2.48 (m, 2H); MS (DCI/NH$_3$) m/z 396 [M+H]$^+$.

What is claimed is:

1. A compound according to formula (I),

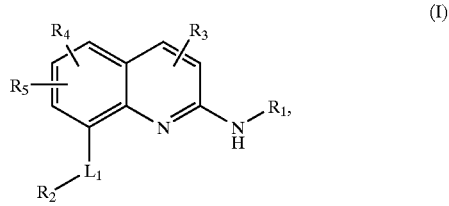

or a therapeutically suitable salt or prodrug thereof, wherein L$_1$ is a bond or is a member selected from the group consisting of —C(O)—, —O—, —S—, —S(O)—, and —S(O)$_2$—;

$R_1$ is a member selected from the group consisting of hydrogen, alkyl, alkoxy, arylalkyl, arylalkoxy, arylcarbonyl, heterocycle, heterocyclealkyl, and $R_AR_B$Ncarbonyl;

$R_2$ is a member selected from the group consisting of alkyl, alkoxy, alkenyl, alkoxyalkyl, aryl, arylalkyl, aryloxyalkyl, cycloalkyl, cycloalkylalkyl, haloalkyl, heterocycle, heterocyclealkyl, heterocycleoxyalkyl, heterocycleoxyalkoxyalkyl, $R_7L_2R_6$—, $R_A$Salkyl, and $R_AR_B$Nalkyl;

$R_3$ is hydrogen;

$R_4$, and $R_5$ are each independently a member selected from the group consisting of hydrogen, alkyl, alkoxy, hydroxy, cyano, halo, haloalkoxy, $R_AR_B$N—, and alkylcarbonylNH—;

$R_6$ and $R_7$ are each independently a member selected from the group consisting of aryl, cycloalkyl, and heterocycle;

$R_A$ and $R_B$ are each independently a member selected from the group consisting of hydrogen, alkyl, aryl and heterocycle;

$L_2$ is —$(CH_2)_m X(CH_2)_n$—,

X is a member selected from the group consisting of —C(O)—, —O—, —S—, —S(O)—, —S(O)$_2$— or is a covalent bond, m is 0, 1, 2, 3, or 4;

n is 0, 1, 2, 3, or 4; and provided that if i) any of $R_3$, $R_4$, or $R_5$ is alkyl or alkoxy, or if ii) L is a bond and $R_2$ is either alkyl or alkoxy; then $R_1$ must be other than hydrogen.

2. A compound according to formula (Ia),

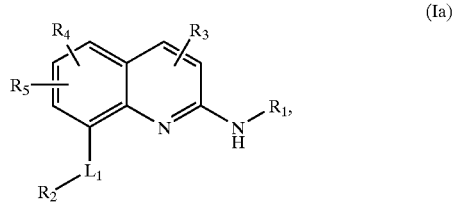

(Ia)

or a therapeutically suitable salt or prodrug thereof, wherein $L_1$ is —O—;

$R_1$ is selected from the group consisting of hydrogen, alkyl, alkoxy, arylalkyl, arylalkoxy, arylcarbonyl, heterocycle, heterocyclealkyl, and $R_AR_B$Ncarbonyl;

$R_2$ is selected from the group consisting of alkyl, alkenyl;

$R_3$ is hydrogen;

$R_4$, and $R_5$ are each independently selected from the group consisting of hydrogen, alkyl, alkoxy, hydroxy, cyano, halo, haloalkoxy, $R_AR_B$N—, and alkylcarbonylNH—;

$R_A$ and $R_B$ are each independently selected from the group consisting of hydrogen, alkyl, aryl and heterocycle;

provided that if i) any of $R_3$, $R_4$, or $R_5$ is alkyl or alkoxy, or if ii) L is a bond and $R_2$ is either alkyl or alkoxy; then $R_1$ must be other than hydrogen.

3. The compound according to claim 2, that is a member selected from the group consisting of 2-(((8-(1,3,3-trimethylbutoxy)quinolin-2-yl)amino)carbonyl)benzyl benzoate;

N-(3-((2-aminoquinolin-8-yl)oxy)propyl)-8-(1,3,3-trimethylbutoxy)quinolin-2-amine.

4. A compound according to formula (Ib),

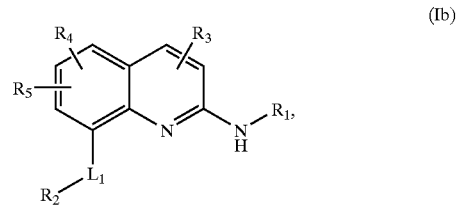

(Ib)

or a therapeutically suitable salt or prodrug thereof, wherein $L_1$ is —O—;

$R_1$ is a member selected from the group consisting of hydrogen, alkyl, alkoxy, aryl, arylalkyl, arylalkoxy, arylcarbonyl, heterocycle, heterocyclealkyl, and $R_AR_B$Ncarbonyl;

$R_2$ is alkyl, wherein alkyl is $C_6$ or larger;

$R_3$ is a member selected from the group consisting of hydrogen, alkyl, hydroxy, cyano, halo, haloalkoxy, $R_AR_B$N—, and alkylcarbonylNH—;

$R_4$, and $R_5$ are each independently a member selected from the group consisting of hydrogen, alkyl, alkoxy, hydroxy, cyano, halo, haloalkoxy, $R_AR_B$N—, and alkylcarbonylNH—; and $R_A$ and $R_B$ are each independently a member selected from the group consisting of hydrogen, alkyl, aryl and heterocycle.

5. The compound according to claim 4, that is a member selected from the group consisting of 8-(1,3,3-trimethylbutoxy)quinolin-2-amine;
8-(2-ethyl-1-methylbutoxy)quinolin-2-amine;
8-(hexyloxy)quinolin-2-amine;
8-(3,3-dimethylbutoxy)quinolin-2-amine;
8-((1-ethylpentyl)oxy)quinolin-2-amine;
8-(1-ethyl-2-methylpropoxy)quinolin-2-amine;
8-(1,2-diethylbutoxy)quinolin-2-amine;
8-((1,4-diethylhexyl)oxy)quinolin-2-amine;
8-(1,3-dimethylbutoxy)quinolin-2-amine;
8-((1-isopropylpentyl)oxy)quinolin-2-amine;
8-((1-ethyl-4-methylpentyl)oxy)quinolin-2-amine;
N-methyl-8-(1,3,3-trimethylbutoxy)quinolin-2-amine;
N-propyl-8-(1,3,3-trimethylbutoxy)quinolin-2-amine;
8-(((1R)-1,3,3-trimethylbutyl)oxy)quinolin-2-amine;
8-(((1S)-1,3,3-trimethylbutyl)oxy)quinolin-2-amine; and
3-methyl-8-(1,3,3-trimethylbutoxy)quinolin-2-amine.

6. A compound according to formula (Ic),

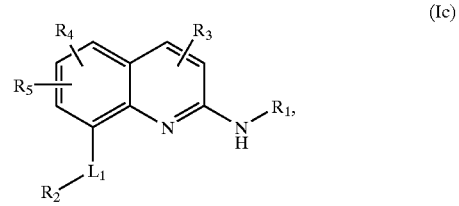

(Ic)

or a therapeutically suitable salt or prodrug thereof, wherein $L_1$ is —O—;

R₁ is a member selected from the group consisting of hydrogen, alkyl, alkoxy, aryl, arylalkyl, arylalkoxy, arylcarbonyl, heterocycle, heterocyclealkyl, and R$_A$R$_B$Ncarbonyl;

R₂ is a member selected from the group consisting of alkoxyalkyl, haloalkyl, R$_A$Salkyl, and R$_A$R$_B$Nalkyl;

R₃ is a member selected from the group consisting of hydrogen, alkyl, hydroxy, cyano, halo, haloalkoxy, R$_A$R$_B$N—, and alkylcarbonylNH—;

R₄, and R₅ are each independently a member selected from the group consisting of hydrogen, alkyl, alkoxy, hydroxy, cyano, halo, haloalkoxy, R$_A$R$_B$N—, and alkylcarbonylNH—;

R$_A$ and R$_B$ are each independently a member selected from the group consisting of hydrogen, alkyl, aryl and heterocycle.

7. The compound according to claim 6, that is a member selected from the group consisting of
8-(2-methoxy-1-methylethoxy)quinolin-2-amine;
8-(2-ethoxy-1-methylethoxy)quinolin-2-amine;
8-(3-methoxy-3-methylbutoxy)quinolin-2-amine;
8-(1-(methoxymethyl)propoxy)quinolin-2-amine;
8-(3-ethoxy-1-ethylpropoxy)quinolin-2-amine;
8-(3-methoxybutoxy)quinolin-2-amine;
8-(3,3,3-trifluoropropoxy)quinolin-2-amine;
8-(2-(methylthio)ethoxy)quinolin-2-amine;
4-((3-((2-aminoquinolin-8-yl)oxy)propyl)amino)-6-methyl-2H-chromen-2-one; and
4-((3-((2-aminoquinolin-8-yl)oxy)propyl)amino)-6-chloro-2H-chromen-2-one.

8. A compound according to formula (Id),

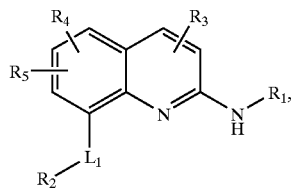

(Id)

or a therapeutically suitable salt or prodrug thereof, wherein
L₁ is —O—;
R₁ is a member selected from the group consisting of hydrogen, alkyl, alkoxy, aryl, arylalkyl, arylalkoxy, arylcarbonyl, heterocycle, heterocyclealkyl, and R$_A$R$_B$Ncarbonyl;
R₂ is a member selected from the group consisting of aryl, cycloalkyl and heterocycle;
R₃ is a member selected from the group consisting of hydrogen, alkyl, hydroxy, cyano, halo, haloalkoxy, R$_A$R$_B$N—, and alkylcarbonylNH—;
R₄, and R₅ are each independently a member selected from the group consisting of hydrogen, alkyl, alkoxy, hydroxy, cyano, halo, haloalkoxy, R$_A$R$_B$N—, and alkylcarbonylNH—;
R$_A$ and R$_B$ are each independently a member selected from the group consisting of hydrogen, alkyl, aryl and heterocycle.

9. The compound according to claim 8, that is a member selected from the group consisting of
8-(cyclobutyloxy)quinolin-2-amine;
8-(cyclopentyloxy)quinolin-2-amine;
8-(cyclohexyloxy)quinolin-2-amine;
8-((3-methylcyclopentyl)oxy)quinolin-2-amine;
8-((2-methylcyclohexyl)oxy)quinolin-2-amine;
8-((3-methylcyclohexyl)oxy)quinolin-2-amine;
8-((4-methylcyclohexyl)oxy)quinolin-2-amine;
8-(cycloheptyloxy)quinolin-2-amine;
8-(((1R,2S)-2-methylcyclohexyl)oxy)quinolin-2-amine;
8-(((1R,2S)-2-methylcyclopentyl)oxy)quinolin-2-amine;
8-(2,3-dihydro-1H-inden-2-yloxy)quinolin-2-amine;
8-(((1S,5S)-3,3,5-trimethylcyclohexyl)oxy)quinolin-2-amine;
8-(((1R,5S)-3,3,5-trimethylcyclohexyl)oxy)quinolin-2-amine;
8-(((3S)-1-benzylpyrrolidin-3-yl)oxy)quinolin-2-amine;
8-(((3R)-1-benzylpyrrolidin-3-yl)oxy)quinolin-2-amine;
8-((1-benzylpiperidin-4-yl)oxy)quinolin-2-amine;
8-(((3S)-1-(1,3-benzodioxol-5-ylmethyl)pyrrolidin-3-yl)oxy)quinolin-2-amine;
8-(((3S)-1-(2-fluorobenzyl)pyrrolidin-3-yl)oxy)quinolin-2-amine;
8-(((3S)-1-(1,1'-biphenyl-4-ylmethyl)pyrrolidin-3-yl)oxy)quinolin-2-amine;
8-(((3S)-1-((3-methyl-1-benzothien-2-yl)methyl)pyrrolidin-3-yl)oxy)quinolin-2-amine;
8-(((3S)-1-((2,2-dimethyl-3,4-dihydro-2H-chromen-6-yl)methyl)pyrrolidin-3-yl)oxy)quinolin-2-amine;
tert-butyl (3S)-3-((2-aminoquinolin-8-yl)oxy)pyrrolidine-1-carboxylate;
8-((3S)-pyrrolidin-3-yloxy)quinolin-2-amine;
8-(((3S)-1-(4-tert-butylbenzyl)pyrrolidin-3-yl)oxy)quinolin-2-amine;
8-(((3S)-1-(2,3-dihydro-1,4-benzodioxin-6-ylmethyl)pyrrolidin-3-yl)oxy)quinolin-2-amine;
8-(((3S)-1-(2,3-difluorobenzyl)pyrrolidin-3-yl)oxy)quinolin-2-amine;
8-(((3S)-1-(3-(trifluoromethyl)benzyl)pyrrolidin-3-yl)oxy)quinolin-2-amine;
8-(((3S)-1-((2,2-difluoro-1,3-benzodioxol-5-yl)methyl)pyrrolidin-3-yl)oxy)quinolin-2-amine;
8-(((3S)-1-(2,4-dimethylbenzyl)pyrrolidin-3-yl)oxy)quinolin-2-amine; and
N-(2,3-dihydro-1,4-benzodioxin-6-ylmethyl)-8-(((3S)-1-(2,3-dihydro-1,4-benzodioxin-6-ylmethyl)pyrrolidin-3-yl)oxy)quinolin-2-amine.

10. A compound according to formula (Ie),

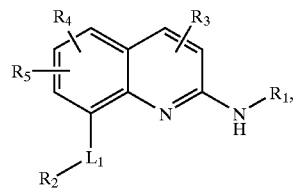

(Ie)

or a therapeutically suitable salt or prodrug thereof, wherein
L₁ is —O—;
R₁ is a member selected from the group consisting of hydrogen, alkyl, alkoxy, aryl, arylalkyl, arylalkoxy, arylcarbonyl, heterocycle, heterocyclealkyl, and R$_A$R$_B$Ncarbonyl;
R₂ is a member selected from the group consisting of arylalkyl, aryloxyalkyl, cycloalkylalkyl, heterocyclealkyl, heterocycleoxyalkyl, heterocycleoxyalkoxyalkyl, R₇L₂R₆—;

R₃ is a member selected from the group consisting of hydrogen, alkyl, hydroxy, cyano, halo, haloalkoxy, $R_AR_BN$—, and alkylcarbonylNH—;

R₄, and R₅ are each independently a member selected from the group consisting of hydrogen, alkyl, alkoxy, hydroxy, cyano, halo, haloalkoxy, $R_AR_BN$—, and alkylcarbonylNH—;

$R_A$ and $R_B$ are each independently a member selected from the group consisting of hydrogen, alkyl, aryl and heterocycle R₆ and R₇ are each independently a member selected from the group consisting of aryl, cycloalkyl and heterocycle;

L₂ is —(CH₂)ₘX(CH₂)ₙ—;

X is a member selected from the group consisting of —C(O)—, —O—, —S—, —S(O)—, —S(O)— or is a covalent bond;

m is 0, 1, 2, 3 or 4;

n is 0, 1, 2, 3 or 4;

provided that if any of R₃, R₄ or R₅ is alkyl or alkoxy, then R₁ must be other than hydrogen.

11. The compound according to claim 10, that is a member selected from the group consisting of 8-(((1S)-2-methyl-1-phenylpropyl)oxy)quinolin-2-amine;
8-(1-benzylpropoxy)quinolin-2-amine;
8-(1-(4-fluorophenyl)ethoxy)quinolin-2-amine;
8-(1-methyl-2-phenylethoxy)quinolin-2-amine;
8-(2-(1-naphthyl)ethoxy)quinolin-2-amine;
8-(benzyloxy)quinolin-2-amine;
8-((3-(trifluoromethyl)benzyl)oxy)quinolin-2-amine;
8-((2,4-dimethylbenzyl)oxy)quinolin-2-amine;
8-(((1R)-1-phenylethyl)oxy)quinolin-2-amine;
8-(1-(4-(trifluoromethyl)phenyl)ethoxy)quinolin-2-amine;
8-((4-(((2-aminoquinolin-8-yl)oxy)methyl)benzyl)oxy)-quinolin-2-amine;
8-(3-phenoxypropoxy)quinolin-2-amine;
8-(3-(3,5-dichlorophenoxy)propoxy)quinolin-2-amine;
8-(4-(3,5-dichlorophenoxy)-1-methylbutoxy)quinolin-2-amine;
8-(4-(2-methoxyphenoxy)-1-methylbutoxy)quinolin-2-amine;
N-(4-((4-((2-aminoquinolin-8-yl)oxy)pentyl)oxy)phenyl) acetamide;
methyl 3-((4-((2-aminoquinolin-8-yl)oxy)pentyl)oxy) berizoate;
8-(1-methyl-4-(3,4,5-trimethylphenoxy)butoxy)quinolin-2-amine;
methyl O-(4-((2-aminoquinolin-8-yl)oxy)pentyl)-L-tyrosinate;
8-(1-methyl-4-(2-naphthyloxy)butoxy)quinolin-2-amine;
1-(4-((4-((2-aminoquinolin-8-yl)oxy)pentyl)oxy)-3-methylphenyl)ethanone;
8-(1-methyl-4-(4-propylphenoxy)butoxy)quinolin-2-amine;
8-(4-(3-isopropylphenoxy)-1-methylbutoxy)quinolin-2-amine;
8-(4-(4-chloro-3-fluorophenoxy)-1-methylbutoxy)quinolin-2-amine;
2-((4-((2-aminoquinolin-8-yl)oxy)pentyl)oxy)benzonitrile;
2-((4-((2-aminoquinolin-8-yl)oxy)pentyl)oxy)benzamide;
8-(1-methyl-4-(2-methyl-5-nitrophenoxy)butoxy)quinolin-2-amine;
8-(4-((5-amino-1-naphthyl)oxy)-1-methylbutoxy)quinolin-2-amine;
8-(4-(3-anilinophenoxy)-1-methylbutoxy)quinolin-2-amine;
8-(4-(2-chloro-4-methoxyphenoxy)-1-methylbutoxy) quinolin-2-amine;
8-(4-((4-methoxy-1-naphthyl)oxy)-1-methylbutoxy) quinolin-2-amine;
methyl (4-((4-((2-aminoquinolin-8-yl)oxy)pentyl)oxy) phenyl)acetate;
ethyl 2-((4-((2-aminoquinolin-8-yl)oxy)pentyl)oxy)-5-methylbenzoate;
8-(4-(4-bromo-2-fluorophenoxy)-1-methylbutoxy)quinolin-2-amine;
N-(3-((4-((2-aminoquinolin-8-yl)oxy)pentyl)oxy)phenyl) urea;
4-(4-((4-((2-aminoquinolin-8-yl)oxy)pentyl)oxy)phenyl) butan-2-one;
ethyl 2-((4-((2-aminoquinolin-8-yl)oxy)pentyl)oxy)benzoate;
methyl 2-((4-((2-aminoquinolin-8-yl)oxy)pentyl)oxy)-5-methoxybenzoate;
8-(4-(4-amino-2-chlorophenoxy)-1-methylbutoxy)quinolin-2-amine;
1-(4-((4-((2-aminoquinolin-8-yl)oxy)pentyl)oxy)phenyl) propan-1-one;
8-(4-(3-(diethylamino)phenoxy)-1-methylbutoxy)quinolin-2-amine;
8-(4-(1,1'-biphenyl-3-yloxy)-1-methylbutoxy)quinolin-2-amine;
8-(4-(2-fluoro-5-methylphenoxy)-1-methylbutoxy)quinolin-2-amine;
8-(4-(2-ethoxy-5-((1E)-prop-1-enyl)phenoxy)-1-methylbutoxy)quinolin-2-amine;
methyl 2-((4-((2-aminoquinolin-8-yl)oxy)pentyl)oxy)-4-methoxybenzoate;
8-(4-(2-benzylphenoxy)-1-methylbutoxy)quinolin-2-amine;
8-(4-(2-fluoro-4-nitrophenoxy)-1-methylbutoxy)quinolin-2-amine;
5-acetyl-2-((4-((2-aminoquinolin-8-yl)oxy)pentyl)oxy) benzamide;
8-(4-(2,3-dihydro-1H-inden-5-yloxy)-1-methylbutoxy) quinolin-2-amine;
8-(4-(1H-imidazol-1-yl)phenoxy)-1-methylbutoxy) quinolin-2-amine;
8-(4-(2-isoxazol-5-ylphenoxy)-1-methylbutoxy)quinolin-2-amine;
8-(4-(2-methoxy-4-propylphenoxy)-1-methylbutoxy) quinolin-2-amine;
8-(4-(2-chloro-3-(trifluoromethyl)phenoxy)-1-methylbutoxy)quinolin-2-amine;
8-(1-methyl-4-(2-methylphenoxy)butoxy)quinolin-2-amine;
8-(1-methyl-4-(3-methylphenoxy)butoxy)quinolin-2-amine;
8-(1-methyl-4-(4-methylphenoxy)butoxy)quinolin-2-amine;
8-(4-(2-chloro-5-methylphenoxy)-1-methylbutoxy) quinolin-2-amine;
4-((4-((2-aminoquinolin-8-yl)oxy)pentyl)oxy)phenol;
8-(4-(3-methoxyphenoxy)-1-methylbutoxy)quinolin-2-amine;
8-(4-(4-methoxyphenoxy)-1-methylbutoxy)quinolin-2-amine;
8-(4-(2-fluorophenoxy)-1-methylbutoxy)quinolin-2-amine;

8-(4-(3-fluorophenoxy)-1-methylbutoxy)quinolin-2-amine;
8-(4-(4-fluorophenoxy)-1-methylbutoxy)quinolin-2-amine;
8-(4-(2-chlorophenoxy)-1-methylbutoxy)quinolin-2-amine;
8-(4-(3-chlorophenoxy)-1-methylbutoxy)quinolin-2-amine;
8-(4-(4-chlorophenoxy)-1-methylbutoxy)quinolin-2-amine;
8-(4-(2-bromophenoxy)-1-methylbutoxy)quinolin-2-amine;
8-(4-(3-bromophenoxy)-1-methylbutoxy)quinolin-2-amine;
8-(4-(4-bromophenoxy)-1-methylbutoxy)quinolin-2-amine;
3-((4-((2-aminoquinolin-8-yl)oxy)pentyl)oxy)benzonitrile;
4-((4-((2-aminoquinolin-8-yl)oxy)pentyl)oxy)benzonitrile;
8-(1-methyl-4-(3-(trifluoromethyl)phenoxy)butoxy)quinolin-2-amine;
8-(1-methyl-4-(4-(trifluoromethyl)phenoxy)butoxy)quinolin-2-amine;
8-(1-methyl-4-(3-(trifluoromethoxy)phenoxy)butoxy)quinolin-2-amine;
8-(4-(2,3-dimethylphenoxy)-1-methylbutoxy)quinolin-2-amine;
8-(4-(2,4-dimethylphenoxy)-1-methylbutoxy)quinolin-2-amine;
8-(4-(2,5-dimethylphenoxy)-1-methylbutoxy)quinolin-2-amine;
8-(4-(3,4-dimethylphenoxy)-1-methylbutoxy)quinolin-2-amine;
8-(4-(3,5-dimethylphenoxy)-1-methylbutoxy)quinolin-2-amine;
8-(4-(2,3-dichlorophenoxy)-1-methylbutoxy)quinolin-2-amine;
8-(4-(2,4-dichlorophenoxy)-1-methylbutoxy)quinolin-2-amine;
8-(4-(2,5-dichlorophenoxy)-1-methylbutoxy)quinolin-2-amine;
8-(4-(3-isopropyl-5-methylphenoxy)-1-methylbutoxy)quinolin-2-amine;
8-(4-(3,4-dichlorophenoxy)-1-methylbutoxy)quinolin-2-amine;
8-(4-(2-chloro-4-methylphenoxy)-1-methylbutoxy)quinolin-2-amine;
8-(4-(2-(benzyloxy)phenoxy)-1-methylbutoxy)quinolin-2-amine;
8-(cyclobutylmethoxy)quinolin-2-amine;
8-(2-cyclopropylethoxy)quinolin-2-amine;
8-(cyclopentylmethoxy)quinolin-2-amine;
8-(cyclohexylmethoxy)quinolin-2-amine;
8-(2-cyclohexylethoxy)quinolin-2-amine;
8-((1S,4R)-bicyclo[2.2.1]hept-2-ylmethoxy)quinolin-2-amine;
8-(1-cyclohexylpropoxy)quinolin-2-amine;
8-(((1R,2R)-2-methylcyclohexyl)oxy)quinolin-2-amine;
8-(1-cyclohexylethoxy)quinolin-2-amine;
8-(tetrahydrofuran-3-ylmethoxy)quinolin-2-amine;
8-(2-(1-methylpyrrolidin-2-yl)ethoxy)quinolin-2-amine;
8-(3-((2-methylquinolin-8-yl)oxy)propoxy)quinolin-2-amine;
8-(3-(quinolin-8-yloxy)propoxy)quinolin-2-amine;
8-(3-((2-aminoquinolin-8-yl)oxy)propoxy)quinolin-2-ol;
6-(3-((2-aminoquinolin-8-yl)oxy)propoxy)quinolin-2-ol;
4-(3-((2-aminoquinolin-8-yl)oxy)propoxy)quinolin-2-amine;
8-(1-methyl-4-((2-methylquinolin-8-yl)oxy)butoxy)quinolin-2-amine;
8-(4-((2-aminoquinolin-8-yl)oxy)-1-methylbutoxy)quinolin-2-amine;
8-(1-methyl-4-(quinolin-7-yloxy)butoxy)quinolin-2-amine;
8-(4-(isoquinolin-5-yloxy)-1-methylbutoxy)quinolin-2-amine;
8-(4-(dibenzo[b,d]furan-2-yloxy)-1-methylbutoxy)quinolin-2-amine;
8-(4-((2,2-dimethyl-2,3-dihydro-1-benzofuran-7-yl)oxy)-1-methylbutoxy)quinolin-2-amine;
6-((4-((2-aminoquinolin-8-yl)oxy)pentyl)oxy)-1,3-benzoxathiol-2-one;
8-(4-(1,3-benzodioxol-5-yloxy)-1-methylbutoxy)quinolin-2-amine;
N-((5-(2-(trifluoromethyl)phenyl)-2-furyl)methyl)-8-(1,3,3-trimethylbutoxy)quinolin-2-amine;
N-((5-(2-nitrophenyl)-2-furyl)methyl)-8-(1,3,3-trimethylbutoxy)quinolin-2-amine;
N-((5-(2-chlorophenyl)-2-furyl)methyl)-8-(1,3,3-trimethylbutoxy)quinolin-2-amine;
8-((5-((2-aminoquinolin-8-yl)oxy)pentyl)oxy)-quinolin-2-amine;
8-(3-((2-aminoquinolin-8-yl)oxy)butoxy)quinolin-2-amine;
8-(3-((2-aminoquinolin-8-yl)oxy)propoxy)-N-methylquinolin-2-amine; and
8-(2-(2-((2-aminoquinolin-8-yl)oxy)ethoxy)ethoxy)-quinolin-2-amine.

12. A compound selected from the group consisting of
8-isopropoxyquinolin-2-amine;
8-sec-butoxyquinolin-2-amine;
8-(1-methylbutoxy)quinolin-2-amine;
8-(1,2-dimethylpropoxy)quinolin-2-amine;
8-(1-ethylpropoxy)quinolin-2-amine;
8-ethoxyquinolin-2-amine;
8-propoxyquinolin-2-amine;
8-butoxyquinolin-2-amine;
8-isobutoxyquinolin-2-amine;
8-(pentyloxy)quinolin-2-amine;
8-(2-methylbutoxy)quinolin-2-amine;
8-(3-methylbutoxy)quinolin-2-amine;
8-(((1R)-1-methylpropyl)oxy)quinolin-2-amine;
8-(((1S)-1,2-dimethylpropyl)oxy)quinolin-2-amine;
8-(((1R)-1,2-dimethylpropyl)oxy)quinolin-2-amine;
8-(((1S)-1-methylpropyl)oxy)quinolin-2-amine; 8-((1-isopropylbut-3-enyl)oxy)quinolin-2-amine;
8-((1,5-dimethylhex-4-enyl)oxy)quinolin-2-amine;
8-((2E)-but-2-enyloxy)quinolin-2-amine; 8-hexylquinolin-2-amine;
8-(1-methylpentyl)quinolin-2-amine;
8-(1-ethylbutyl)quinolin-2-amine;
8-(1-ethylpentyl)quinolin-2-amine; 3-((2-aminoquinolin-8-yl)oxy)propan-1-ol; and
4-((2-aminoquinolin-8-yl)oxy)pentan-1-ol.

13. A method of treating obesity, by antagonizing the MCH receptor comprising administering a therapeutically effective amount of a compound of formula (I) of claim 1.

14. A pharmaceutical composition comprising a therapeutically effective amount of a compound of formula (I) of claim 1 in combination with a pharmaceutically suitable carrier.

* * * * *